US008748389B2

(12) United States Patent
Warenius et al.

(10) Patent No.: US 8,748,389 B2
(45) Date of Patent: Jun. 10, 2014

(54) TREATING CANCER

(75) Inventors: Hilmar Meek Warenius, Heswall (GB);
Jonathan Essex, Alresford (GB);
Jeremy Kilburn, Eastleigh (GB)

(73) Assignee: Theryte Limited, Liverpool (GB)

( * ) Notice: Subject to any disclaimer, the term of this patent is extended or adjusted under 35 U.S.C. 154(b) by 1858 days.

(21) Appl. No.: 11/570,743

(22) PCT Filed: Jun. 14, 2005

(86) PCT No.: PCT/GB2005/002320
§ 371 (c)(1),
(2), (4) Date: Mar. 24, 2008

(87) PCT Pub. No.: WO2005/123760
PCT Pub. Date: Dec. 29, 2005

(65) Prior Publication Data
US 2008/0247999 A1     Oct. 9, 2008

(30) Foreign Application Priority Data

Jun. 15, 2004   (GB) .................................. 0413346.8

(51) Int. Cl.
*A61K 38/08*   (2006.01)
*A61K 38/17*   (2006.01)
*C07K 7/06*    (2006.01)
*C07K 14/47*   (2006.01)

(52) U.S. Cl.
USPC ......... 514/19.3; 514/1.2; 514/21.4; 514/21.6; 530/324; 530/326; 530/328

(58) Field of Classification Search
None
See application file for complete search history.

(56) References Cited

U.S. PATENT DOCUMENTS

| | | | |
|---|---|---|---|
| 5,962,316 A * | 10/1999 | Beach et al. | 435/325 |
| 6,149,906 A * | 11/2000 | Mosca | 424/93.7 |
| 6,184,205 B1 | 2/2001 | Sparks et al. | |
| 6,344,436 B1 * | 2/2002 | Smith et al. | 514/7.4 |
| 6,653,450 B1 | 11/2003 | Berg et al. | |
| 2004/0171809 A1 * | 9/2004 | Korsmeyer et al. | 530/350 |
| 2005/0250683 A9 * | 11/2005 | Rozema et al. | 514/12 |

FOREIGN PATENT DOCUMENTS

| | | |
|---|---|---|
| JP | 01224398 A2 | 9/1989 |
| JP | 09511910 A | 12/1997 |
| WO | 9528169 A1 | 10/1995 |
| WO | WO 95/28169 A1 | 10/1995 |
| WO | WO 99/47661 A2 | 9/1999 |
| WO | WO 99/47661 A3 | 9/1999 |
| WO | WO 03/044169 A2 | 5/2003 |
| WO | WO 03/044169 A3 | 5/2003 |
| WO | WO 03/081239 A2 | 10/2003 |
| WO | WO 03/081239 A3 | 10/2003 |
| WO | WO 2004/011650 A2 | 2/2004 |
| WO | WO 2004/011650 A3 | 2/2004 |

OTHER PUBLICATIONS

Swart et al. Studies on the High-Sulphur Proteins of Reduced Merino Wool. Biochemical Journal. 1973, vol. 133, pp. 641-654.*
Tok et al. Binding of a Cyclic BIV beta-Tat Peptide with its TAR RNA Construct. Bioorganic & Medicinal Chemistry Letters. 2001, vol. 11, pp. 43-46.*
Lin et al. A Latent Inhibitor of Fibrin Polymerization with Ancillary Anticoagulant Activity. Thrombosis Research. 2000, vol. 97, pp. 375-378.*
Yang et al. Gly-Pro-Arg Confers Stability Similar to Gly-Pro-Hyp in the Collagen Triple-Helix of Host-Guest Peptides. The Journal of Biological Chemistry. Nov. 14, 1997, vol. 272, No. 46, pp. 28837-28840.*
Matsubara, Hiroko. Office Action. Japanese Application No. JP2007-516025. Drafting Date: Feb. 17, 2011.
Mutoh et al., 1999, "A p21 Waf1/Cip1 Carboxyl-terminal Peptide Exhibited Cyclin-dependent Kinase-inhibitory Activity and Cytotoxicity When Introduced into Human Cells," *Cancer Research*, 59(14):3480-3488.
Milanesa, et al., 2000, "Methylglyoxal-Induced Apoptosis in Human Prostate Carcinoma: Potential Modality for Prostate Cancer Treatment," *European Urology*, 37(6):728-734.
International Search Report from PCT/GB2005/002320 dated Mar. 22, 2006.

\* cited by examiner

*Primary Examiner* — Jeffrey E Russel
(74) *Attorney, Agent, or Firm* — Gavrilovich, Dodd & Lindsey LLP

(57) ABSTRACT

The present invention provides a peptide comprising an amino acid sequence that is part of the amino acid sequence of CDK4 protein, or homologous to part of the amino acid sequence of CDK4 protein, which peptide is cytotoxic to, and/or inhibiting to the growth of, a cancer cell and/or stimulating to the growth of a non-cancerous cell and/or a control cell. Methods of identifying such peptides and medical uses of such peptides are also disclosed.

19 Claims, 22 Drawing Sheets

| | Cyclin B | Cyclin D1 | CDK1 | CDK4 | CDK2 | C-raf-1 | C-myc-1 | pan ras | pan P53 | Topo IIa | Actin | Bcl2 | Mos | GSH | Bax | P27Kip1 | p21 |
|---|---|---|---|---|---|---|---|---|---|---|---|---|---|---|---|---|---|
| Cyclin B | | r = 0.071 p = 0.794 | r = 0.379 p = 0.147 | r = 0.468 p = 0.067 | r = 0.471 p = 0.089 | r = 0.368 p = 0.161 | r = 0.164 p = 0.545 | r = 0.097 p = 0.721 | r = 0.267 p = 0.318 | r = 0.171 p = 0.526 | r = 0.211 p = 0.432 | r = 0.146 p = 0.590 | r = 0.008 p = 0.979 | r = 0.416 p = 0.123 | r = 0.254 p = 0.344 | r = 0.031 p = 0.928 | r = 0.505 p = 0.248 |
| Cyclin D1 | r = 0.071 p = 0.794 | | r = 0.030 p = 0.902 | r = 0.274 p = 0.257 | r = 0.144 p = 0.594 | r = 0.160 p = 0.513 | r = 0.351 p = 0.154 | r = 0.354 p = 0.150 | r = 0.298 p = 0.230 | r = 0.084 p = 0.526 | r = 0.298 p = 0.432 | r = 0.054 p = 0.828 | r = 0.243 p = 0.348 | r = 0.251 p = 0.331 | r = 0.165 p = 0.513 | r = 0.320 p = 0.311 | r = 0.273 p = 0.514 |
| CDK1 | r = 0.379 p = 0.147 | r = 0.030 p = 0.902 | | r = 0.872 p = 0.0001 | r = 0.530 p = 0.029 | r = 0.194 p = 0.414 | r = 0.353 p = 0.138 | r = 0.264 p = 0.274 | r = 0.102 p = 0.679 | r = 0.012 p = 0.960 | r = 0.184 p = 0.452 | r = 0.545 p = 0.013 | r = 0.016 p = 0.951 | r = 0.034 p = 0.895 | r = 0.173 p = 0.480 | r = 0.592 p = 0.037 | r = 0.484 p = 0.224 |
| CDK4 | r = 0.468 p = 0.067 | r = 0.274 p = 0.257 | r = 0.872 p = 0.0001 | | r = 0.627 p = 0.007 | r = 0.118 p = 0.620 | r = 0.393 p = 0.096 | r = 0.197 p = 0.418 | r = 0.020 p = 0.935 | r = 0.118 p = 0.630 | r = 0.216 p = 0.375 | r = 0.500 p = 0.030 | r = 0.009 p = 0.973 | r = 0.079 p = 0.756 | r = 0.155 p = 0.528 | r = 0.354 p = 0.235 | r = 0.508 p = 0.199 |
| CDK2 | r = 0.471 p = 0.089 | r = 0.144 p = 0.594 | r = 0.530 p = 0.029 | r = 0.627 p = 0.007 | | r = 0.152 p = 0.561 | r = 0.134 p = 0.609 | r = 0.097 p = 0.712 | r = 0.062 p = 0.813 | r = 0.032 p = 0.904 | r = 0.002 p = 0.993 | r = 0.352 p = 0.166 | r = 0.123 p = 0.650 | r = 0.403 p = 0.122 | r = 0.110 p = 0.684 | r = 0.288 p = 0.364 | r = 0.033 p = 0.944 |
| C-raf-1 | r = 0.368 p = 0.161 | r = 0.160 p = 0.513 | r = 0.194 p = 0.414 | r = 0.118 p = 0.620 | r = 0.152 p = 0.561 | | r = 0.155 p = 0.525 | r = 0.115 p = 0.641 | r = 0.058 p = 0.815 | r = 0.198 p = 0.416 | r = 0.468 p = 0.044 | r = 0.224 p = 0.343 | r = 0.365 p = 0.136 | r = 0.250 p = 0.317 | r = 0.275 p = 0.255 | r = 0.223 p = 0.465 | r = 0.154 p = 0.717 |
| C-myc-1 | r = 0.164 p = 0.545 | r = 0.351 p = 0.154 | r = 0.353 p = 0.138 | r = 0.393 p = 0.096 | r = 0.134 p = 0.609 | r = 0.155 p = 0.525 | | r = 0.002 p = 0.994 | r = 0.019 p = 0.937 | r = 0.013 p = 0.957 | r = 0.158 p = 0.517 | r = 0.246 p = 0.310 | r = 0.402 p = 0.098 | r = 0.431 p = 0.074 | r = 0.181 p = 0.472 | r = 0.401 p = 0.174 | r = 0.072 p = 0.866 |
| pan ras | r = 0.097 p = 0.721 | r = 0.354 p = 0.150 | r = 0.264 p = 0.274 | r = 0.197 p = 0.418 | r = 0.097 p = 0.712 | r = 0.115 p = 0.641 | r = 0.002 p = 0.994 | | r = 0.044 p = 0.859 | r = 0.272 p = 0.261 | r = 0.044 p = 0.931 | r = 0.183 p = 0.454 | r = 0.083 p = 0.743 | r = 0.327 p = 0.185 | r = 0.083 p = 0.744 | r = 0.390 p = 0.187 | r = 0.431 p = 0.287 |
| pan P53 | r = 0.267 p = 0.318 | r = 0.298 p = 0.230 | r = 0.102 p = 0.679 | r = 0.020 p = 0.935 | r = 0.062 p = 0.813 | r = 0.058 p = 0.815 | r = 0.019 p = 0.937 | r = 0.044 p = 0.859 | | r = 0.112 p = 0.648 | r = 0.021 p = 0.931 | r = 0.089 p = 0.717 | r = 0.094 p = 0.711 | r = 0.184 p = 0.464 | r = 0.350 p = 0.155 | r = 0.034 p = 0.911 | r = 0.463 p = 0.248 |
| Topo IIa | r = 0.171 p = 0.526 | r = 0.027 p = 0.916 | r = 0.012 p = 0.960 | r = 0.118 p = 0.630 | r = 0.032 p = 0.904 | r = 0.198 p = 0.416 | r = 0.013 p = 0.957 | r = 0.272 p = 0.261 | r = 0.112 p = 0.648 | | r = 0.474 p = 0.040 | r = 0.086 p = 0.725 | r = 0.227 p = 0.364 | r = 0.078 p = 0.759 | r = 0.031 p = 0.903 | r = 0.246 p = 0.419 | r = 0.375 p = 0.360 |
| Actin | r = 0.211 p = 0.432 | r = 0.298 p = 0.230 | r = 0.184 p = 0.452 | r = 0.216 p = 0.375 | r = 0.002 p = 0.993 | r = 0.468 p = 0.044 | r = 0.158 p = 0.517 | r = 0.021 p = 0.931 | r = 0.171 p = 0.484 | r = 0.474 p = 0.040 | | r = 0.067 p = 0.784 | r = 0.702 p = 0.001 | r = 0.141 p = 0.578 | r = 0.036 p = 0.886 | r = 0.242 p = 0.427 | r = 0.050 p = 0.907 |
| Bcl2 | r = 0.146 p = 0.590 | r = 0.054 p = 0.828 | r = 0.545 p = 0.013 | r = 0.500 p = 0.030 | r = 0.352 p = 0.166 | r = 0.224 p = 0.343 | r = 0.246 p = 0.310 | r = 0.183 p = 0.454 | r = 0.089 p = 0.717 | r = 0.086 p = 0.725 | r = 0.067 p = 0.784 | | r = 0.120 p = 0.634 | r = 0.083 p = 0.745 | r = 0.585 p = 0.009 | r = 0.398 p = 0.178 | r = 0.725 p = 0.042 |
| Mos | r = 0.008 p = 0.979 | r = 0.243 p = 0.348 | r = 0.016 p = 0.951 | r = 0.009 p = 0.973 | r = 0.123 p = 0.650 | r = 0.365 p = 0.136 | r = 0.402 p = 0.098 | r = 0.083 p = 0.743 | r = 0.094 p = 0.711 | r = 0.227 p = 0.364 | r = 0.702 p = 0.001 | r = 0.120 p = 0.634 | | r = 0.087 p = 0.739 | r = 0.241 p = 0.352 | r = 0.311 p = 0.302 | r = 0.296 p = 0.477 |
| GSH | r = 0.416 p = 0.123 | r = 0.251 p = 0.331 | r = 0.034 p = 0.895 | r = 0.079 p = 0.756 | r = 0.403 p = 0.122 | r = 0.250 p = 0.317 | r = 0.431 p = 0.074 | r = 0.327 p = 0.185 | r = 0.184 p = 0.464 | r = 0.078 p = 0.759 | r = 0.141 p = 0.578 | r = 0.083 p = 0.745 | r = 0.087 p = 0.739 | | r = 0.171 p = 0.523 | r = 0.113 p = 0.712 | r = 0.274 p = 0.553 |
| Bax | r = 0.254 p = 0.344 | r = 0.165 p = 0.513 | r = 0.173 p = 0.480 | r = 0.155 p = 0.528 | r = 0.110 p = 0.684 | r = 0.275 p = 0.255 | r = 0.181 p = 0.472 | r = 0.083 p = 0.744 | r = 0.350 p = 0.155 | r = 0.031 p = 0.903 | r = 0.036 p = 0.886 | r = 0.585 p = 0.009 | r = 0.241 p = 0.352 | r = 0.171 p = 0.523 | | r = 0.116 p = 0.706 | r = 0.373 p = 0.362 |
| P27Kip1 | r = 0.031 p = 0.928 | r = 0.320 p = 0.311 | r = 0.582 p = 0.037 | r = 0.354 p = 0.235 | r = 0.288 p = 0.364 | r = 0.223 p = 0.465 | r = 0.401 p = 0.174 | r = 0.390 p = 0.187 | r = 0.034 p = 0.911 | r = 0.246 p = 0.419 | r = 0.242 p = 0.427 | r = 0.398 p = 0.178 | r = 0.311 p = 0.302 | r = 0.113 p = 0.712 | r = 0.116 p = 0.706 | | r = 0.292 p = 0.575 |
| P21 | r = 0.505 p = 0.248 | r = 0.273 p = 0.514 | r = 0.484 p = 0.224 | r = 0.508 p = 0.199 | r = 0.033 p = 0.944 | r = 0.154 p = 0.717 | r = 0.072 p = 0.866 | r = 0.431 p = 0.287 | r = 0.463 p = 0.248 | r = 0.375 p = 0.360 | r = 0.050 p = 0.907 | r = 0.725 p = 0.042 | r = 0.296 p = 0.477 | r = 0.274 p = 0.553 | r = 0.373 p = 0.362 | r = 0.292 p = 0.575 | |

Figure 4

| | Cyclin B | Cyclin D1 | CDK1 | CDK4 | CDK2 | C-raf-1 | C-myc-1 | pan ras | pan P53 | Topo IIa | Actin | Bcl2 | Mos | GSH | Bax | P27Kip1 | p21 |
|---|---|---|---|---|---|---|---|---|---|---|---|---|---|---|---|---|---|
| Cyclin B | | r = 0.185<br>p = 0.691 | r = 0.253<br>p = 0.584 | r = 0.676<br>p = 0.096 | r = 0.218<br>p = 0.638 | r = 0.351<br>p = 0.441 | r = 0.206<br>p = 0.658 | r = 0.225<br>p = 0.628 | r = 0.009<br>p = 0.985 | r = 0.499<br>p = 0.254 | r = 0.038<br>p = 0.935 | r = 0.231<br>p = 0.618 | r = 0.556<br>p = 0.195 | r = 0.696<br>p = 0.125 | r = 0.877<br>p = 0.010 | r = 0.055<br>p = 0.945 | r = 0.238<br>p = 0.650 |
| Cyclin D1 | r = 0.185<br>p = 0.691 | | r = 0.402<br>p = 0.323 | r = 0.297<br>p = 0.475 | r = 0.394<br>p = 0.335 | r = 0.397<br>p = 0.331 | r = 0.168<br>p = 0.691 | r = 0.662<br>p = 0.074 | r = 0.704<br>p = 0.051 | r = 0.045<br>p = 0.916 | r = 0.166<br>p = 0.695 | r = 0.344<br>p = 0.404 | r = 0.384<br>p = 0.348 | r = 0.397<br>p = 0.378 | r = 0.070<br>p = 0.869 | r = 0.247<br>p = 0.689 | r = 0.262<br>p = 0.571 |
| CDK1 | r = 0.253<br>p = 0.584 | r = 0.402<br>p = 0.323 | | r = 0.791<br>p = 0.019 | r = 0.467<br>p = 0.243 | r = 0.293<br>p = 0.482 | r = 0.496<br>p = 0.211 | r = 0.466<br>p = 0.245 | r = 0.516<br>p = 0.191 | r = 0.685<br>p = 0.061 | r = 0.526<br>p = 0.181 | r = 0.588<br>p = 0.125 | r = 0.147<br>p = 0.728 | r = 0.082<br>p = 0.861 | r = 0.027<br>p = 0.950 | r = 0.834<br>p = 0.079 | r = 0.211<br>p = 0.649 |
| CDK4 | r = 0.676<br>p = 0.096 | r = 0.297<br>p = 0.475 | r = 0.791<br>p = 0.019 | | r = 0.346<br>p = 0.402 | r = 0.342<br>p = 0.407 | r = 0.108<br>p = 0.799 | r = 0.338<br>p = 0.412 | r = 0.489<br>p = 0.219 | r = 0.631<br>p = 0.094 | r = 0.444<br>p = 0.270 | r = 0.360<br>p = 0.381 | r = 0.181<br>p = 0.669 | r = 0.386<br>p = 0.392 | r = 0.326<br>p = 0.431 | r = 0.716<br>p = 0.174 | r = 0.116<br>p = 0.805 |
| CDK2 | r = 0.218<br>p = 0.638 | r = 0.394<br>p = 0.335 | r = 0.467<br>p = 0.243 | r = 0.346<br>p = 0.402 | | r = 0.095<br>p = 0.823 | r = 0.562<br>p = 0.148 | r = 0.078<br>p = 0.854 | r = 0.348<br>p = 0.398 | r = 0.058<br>p = 0.891 | r = 0.204<br>p = 0.628 | r = 0.351<br>p = 0.394 | r = 0.005<br>p = 0.990 | r = 0.584<br>p = 0.169 | r = 0.029<br>p = 0.946 | r = 0.024<br>p = 0.970 | r = 0.033<br>p = 0.944 |
| C-raf-1 | r = 0.351<br>p = 0.441 | r = 0.397<br>p = 0.331 | r = 0.293<br>p = 0.482 | r = 0.342<br>p = 0.407 | r = 0.095<br>p = 0.823 | | r = 0.263<br>p = 0.529 | r = 0.280<br>p = 0.503 | r = 0.710<br>p = 0.049 | r = 0.002<br>p = 0.996 | r = 0.468<br>p = 0.242 | r = 0.478<br>p = 0.231 | r = 0.473<br>p = 0.237 | r = 0.408<br>p = 0.364 | r = 0.458<br>p = 0.254 | r = 0.547<br>p = 0.341 | r = 0.475<br>p = 0.281 |
| C-myc-1 | r = 0.206<br>p = 0.658 | r = 0.168<br>p = 0.691 | r = 0.496<br>p = 0.211 | r = 0.108<br>p = 0.799 | r = 0.562<br>p = 0.148 | r = 0.263<br>p = 0.529 | | r = 0.359<br>p = 0.382 | r = 0.056<br>p = 0.895 | r = 0.063<br>p = 0.882 | r = 0.108<br>p = 0.799 | r = 0.395<br>p = 0.333 | r = 0.085<br>p = 0.842 | r = 0.101<br>p = 0.829 | r = 0.367<br>p = 0.371 | r = 0.288<br>p = 0.639 | r = 0.288<br>p = 0.531 |
| pan ras | r = 0.225<br>p = 0.628 | r = 0.662<br>p = 0.074 | r = 0.466<br>p = 0.245 | r = 0.338<br>p = 0.412 | r = 0.078<br>p = 0.854 | r = 0.280<br>p = 0.503 | r = 0.359<br>p = 0.382 | | r = 0.246<br>p = 0.557 | r = 0.611<br>p = 0.108 | r = 0.521<br>p = 0.186 | r = 0.219<br>p = 0.603 | r = 0.389<br>p = 0.341 | r = 0.226<br>p = 0.627 | r = 0.229<br>p = 0.586 | r = 0.936<br>p = 0.020 | r = 0.779<br>p = 0.039 |
| pan P53 | r = 0.009<br>p = 0.985 | r = 0.704<br>p = 0.051 | r = 0.516<br>p = 0.191 | r = 0.489<br>p = 0.219 | r = 0.348<br>p = 0.398 | r = 0.710<br>p = 0.049 | r = 0.056<br>p = 0.895 | r = 0.246<br>p = 0.557 | | r = 0.028<br>p = 0.947 | r = 0.439<br>p = 0.276 | r = 0.332<br>p = 0.422 | r = 0.456<br>p = 0.256 | r = 0.685<br>p = 0.090 | r = 0.145<br>p = 0.732 | r = 0.243<br>p = 0.694 | r = 0.069<br>p = 0.884 |
| Topo IIa | r = 0.499<br>p = 0.254 | r = 0.045<br>p = 0.916 | r = 0.685<br>p = 0.061 | r = 0.631<br>p = 0.094 | r = 0.058<br>p = 0.891 | r = 0.002<br>p = 0.996 | r = 0.063<br>p = 0.882 | r = 0.611<br>p = 0.108 | r = 0.028<br>p = 0.947 | | r = 0.736<br>p = 0.037 | r = 0.016<br>p = 0.970 | r = 0.112<br>p = 0.791 | r = 0.275<br>p = 0.551 | r = 0.419<br>p = 0.302 | r = 0.680<br>p = 0.206 | r = 0.185<br>p = 0.691 |
| Actin | r = 0.038<br>p = 0.935 | r = 0.166<br>p = 0.695 | r = 0.526<br>p = 0.181 | r = 0.444<br>p = 0.270 | r = 0.204<br>p = 0.628 | r = 0.468<br>p = 0.242 | r = 0.108<br>p = 0.799 | r = 0.521<br>p = 0.186 | r = 0.439<br>p = 0.276 | r = 0.736<br>p = 0.037 | | r = 0.086<br>p = 0.840 | r = 0.626<br>p = 0.097 | r = 0.034<br>p = 0.942 | r = 0.129<br>p = 0.761 | r = 0.609<br>p = 0.276 | r = 0.120<br>p = 0.814 |
| Bcl2 | r = 0.231<br>p = 0.618 | r = 0.344<br>p = 0.404 | r = 0.588<br>p = 0.125 | r = 0.360<br>p = 0.381 | r = 0.351<br>p = 0.394 | r = 0.478<br>p = 0.231 | r = 0.395<br>p = 0.333 | r = 0.219<br>p = 0.603 | r = 0.332<br>p = 0.422 | r = 0.016<br>p = 0.970 | r = 0.086<br>p = 0.840 | | r = 0.037<br>p = 0.931 | r = 0.070<br>p = 0.882 | r = 0.633<br>p = 0.092 | r = 0.885<br>p = 0.046 | r = 0.671<br>p = 0.100 |
| Mos | r = 0.556<br>p = 0.195 | r = 0.384<br>p = 0.348 | r = 0.147<br>p = 0.728 | r = 0.181<br>p = 0.669 | r = 0.005<br>p = 0.990 | r = 0.473<br>p = 0.237 | r = 0.085<br>p = 0.842 | r = 0.389<br>p = 0.341 | r = 0.456<br>p = 0.256 | r = 0.112<br>p = 0.791 | r = 0.626<br>p = 0.097 | r = 0.037<br>p = 0.931 | | r = 0.105<br>p = 0.823 | r = 0.282<br>p = 0.498 | r = 0.085<br>p = 0.892 | r = 0.227<br>p = 0.624 |
| GSH | r = 0.696<br>p = 0.125 | r = 0.397<br>p = 0.378 | r = 0.082<br>p = 0.861 | r = 0.386<br>p = 0.392 | r = 0.584<br>p = 0.169 | r = 0.408<br>p = 0.364 | r = 0.101<br>p = 0.829 | r = 0.226<br>p = 0.627 | r = 0.685<br>p = 0.090 | r = 0.275<br>p = 0.551 | r = 0.034<br>p = 0.942 | r = 0.070<br>p = 0.882 | r = 0.105<br>p = 0.823 | | r = 0.202<br>p = 0.664 | r = 0.278<br>p = 0.651 | r = 0.323<br>p = 0.533 |
| Bax | r = 0.877<br>p = 0.010 | r = 0.070<br>p = 0.869 | r = 0.027<br>p = 0.950 | r = 0.326<br>p = 0.431 | r = 0.029<br>p = 0.946 | r = 0.458<br>p = 0.254 | r = 0.367<br>p = 0.371 | r = 0.229<br>p = 0.586 | r = 0.145<br>p = 0.732 | r = 0.419<br>p = 0.302 | r = 0.129<br>p = 0.761 | r = 0.633<br>p = 0.092 | r = 0.282<br>p = 0.498 | r = 0.202<br>p = 0.664 | | r = 0.360<br>p = 0.551 | r = 0.435<br>p = 0.330 |
| P27Kip1 | r = 0.055<br>p = 0.945 | r = 0.247<br>p = 0.689 | r = 0.834<br>p = 0.079 | r = 0.716<br>p = 0.174 | r = 0.024<br>p = 0.970 | r = 0.547<br>p = 0.341 | r = 0.288<br>p = 0.639 | r = 0.936<br>p = 0.020 | r = 0.243<br>p = 0.694 | r = 0.680<br>p = 0.206 | r = 0.609<br>p = 0.276 | r = 0.885<br>p = 0.046 | r = 0.085<br>p = 0.892 | r = 0.278<br>p = 0.651 | r = 0.360<br>p = 0.551 | | r = 0.932<br>p = 0.021 |
| P21 | r = 0.238<br>p = 0.650 | r = 0.262<br>p = 0.571 | r = 0.211<br>p = 0.649 | r = 0.116<br>p = 0.805 | r = 0.033<br>p = 0.944 | r = 0.475<br>p = 0.281 | r = 0.288<br>p = 0.531 | r = 0.779<br>p = 0.039 | r = 0.069<br>p = 0.884 | r = 0.185<br>p = 0.691 | r = 0.110<br>p = 0.814 | r = 0.671<br>p = 0.099 | r = 0.227<br>p = 0.624 | r = 0.323<br>p = 0.533 | r = 0.435<br>p = 0.330 | r = 0.932<br>p = 0.021 | |

Figure 5

| | Cyclin B | Cyclin D1 | CDK1 | CDK4 | CDK2 | C-raf-1 | C-myc-1 | pan ras | pan P53 | Topo IIa | Actin | Bcl2 | Mos | GSH | Bax | P27Kip1 | p21 |
|---|---|---|---|---|---|---|---|---|---|---|---|---|---|---|---|---|---|
| Cyclin B | | | r = 0.414<br>p = 0.489 | r = 0.421<br>p = 0.480 | r = 0.567<br>p = 0.433 | r = 0.483<br>p = 0.410 | r = 0.035<br>p = 0.956 | r = 0.330<br>p = 0.588 | r = 0.431<br>p = 0.469 | r = 0.776<br>p = 0.123 | r = 0.546<br>p = 0.341 | r = 0.422<br>p = 0.479 | r = 0.615<br>p = 0.270 | r = 0.128<br>p = 0.838 | r = 0.506<br>p = 0.385 | r = 0.498<br>p = 0.393 | |
| Cyclin D1 | r = 0.438<br>p = 0.461 | | r = 0.872<br>p = 0.023 | r = 0.853<br>p = 0.027 | r = 0.967<br>p = 0.033 | r = 0.087<br>p = 0.870 | r = 0.877<br>p = 0.051 | r = 0.158<br>p = 0.800 | r = 0.084<br>p = 0.893 | r = 0.589<br>p = 0.296 | r = 0.684<br>p = 0.203 | r = 0.824<br>p = 0.086 | r = 0.811<br>p = 0.096 | r = 0.366<br>p = 0.545 | r = 0.445<br>p = 0.377 | r = 0.724<br>p = 0.167 | |
| CDK1 | r = 0.414<br>p = 0.489 | r = 0.872<br>p = 0.023 | | r = 0.993<br>p = 0.0001 | r = 0.933<br>p = 0.067 | r = 0.220<br>p = 0.675 | r = 0.879<br>p = 0.050 | r = 0.237<br>p = 0.702 | r = 0.101<br>p = 0.872 | r = 0.652<br>p = 0.234 | r = 0.308<br>p = 0.614 | r = 0.922<br>p = 0.026 | r = 0.562<br>p = 0.304 | r = 0.701<br>p = 0.187 | r = 0.370<br>p = 0.470 | r = 0.950<br>p = 0.013 | |
| CDK4 | r = 0.421<br>p = 0.480 | r = 0.863<br>p = 0.027 | r = 0.993<br>p = 0.0001 | | r = 0.895<br>p = 0.105 | r = 0.197<br>p = 0.709 | r = 0.845<br>p = 0.072 | r = 0.297<br>p = 0.627 | r = 0.006<br>p = 0.993 | r = 0.714<br>p = 0.175 | r = 0.298<br>p = 0.628 | r = 0.961<br>p = 0.009 | r = 0.522<br>p = 0.367 | r = 0.730<br>p = 0.161 | r = 0.395<br>p = 0.438 | r = 0.955<br>p = 0.011 | |
| CDK2 | r = 0.567<br>p = 0.433 | r = 0.967<br>p = 0.033 | r = 0.933<br>p = 0.067 | r = 0.895<br>p = 0.105 | | r = 0.460<br>p = 0.540 | r = 0.985<br>p = 0.015 | r = 0.010<br>p = 0.990 | r = 0.503<br>p = 0.497 | r = 0.102<br>p = 0.898 | r = 0.390<br>p = 0.610 | r = 0.757<br>p = 0.243 | r = 0.613<br>p = 0.387 | r = 0.423<br>p = 0.527 | r = 0.887<br>p = 0.113 | r = 0.704<br>p = 0.296 | |
| C-raf-1 | r = 0.483<br>p = 0.410 | r = 0.087<br>p = 0.870 | r = 0.220<br>p = 0.675 | r = 0.197<br>p = 0.709 | r = 0.460<br>p = 0.540 | | r = 0.065<br>p = 0.917 | r = 0.232<br>p = 0.708 | r = 0.127<br>p = 0.839 | r = 0.225<br>p = 0.716 | r = 0.385<br>p = 0.522 | r = 0.082<br>p = 0.896 | r = 0.054<br>p = 0.931 | r = 0.256<br>p = 0.678 | r = 0.617<br>p = 0.140 | r = 0.493<br>p = 0.398 | |
| C-myc-1 | r = 0.035<br>p = 0.956 | r = 0.877<br>p = 0.051 | r = 0.879<br>p = 0.050 | r = 0.845<br>p = 0.072 | r = 0.985<br>p = 0.015 | r = 0.065<br>p = 0.917 | | r = 0.114<br>p = 0.855 | r = 0.423<br>p = 0.478 | r = 0.276<br>p = 0.653 | r = 0.320<br>p = 0.599 | r = 0.738<br>p = 0.155 | r = 0.580<br>p = 0.306 | r = 0.614<br>p = 0.271 | r = 0.760<br>p = 0.136 | r = 0.711<br>p = 0.179 | |
| pan ras | r = 0.330<br>p = 0.588 | r = 0.158<br>p = 0.800 | r = 0.237<br>p = 0.702 | r = 0.297<br>p = 0.627 | r = 0.010<br>p = 0.990 | r = 0.232<br>p = 0.708 | r = 0.114<br>p = 0.855 | | r = 0.148<br>p = 0.812 | r = 0.164<br>p = 0.792 | r = 0.599<br>p = 0.164 | r = 0.360<br>p = 0.552 | r = 0.661<br>p = 0.234 | r = 0.844<br>p = 0.072 | r = 0.421<br>p = 0.480 | r = 0.396<br>p = 0.509 | |
| pan P53 | r = 0.431<br>p = 0.469 | r = 0.084<br>p = 0.893 | r = 0.101<br>p = 0.872 | r = 0.006<br>p = 0.993 | r = 0.503<br>p = 0.497 | r = 0.127<br>p = 0.839 | r = 0.423<br>p = 0.478 | r = 0.148<br>p = 0.812 | | r = 0.661<br>p = 0.225 | r = 0.200<br>p = 0.747 | r = 0.255<br>p = 0.679 | r = 0.222<br>p = 0.720 | r = 0.074<br>p = 0.905 | r = 0.264<br>p = 0.667 | r = 0.12<br>p = 0.985 | |
| Topo IIa | r = 0.776<br>p = 0.123 | r = 0.589<br>p = 0.296 | r = 0.652<br>p = 0.234 | r = 0.714<br>p = 0.175 | r = 0.102<br>p = 0.898 | r = 0.225<br>p = 0.716 | r = 0.276<br>p = 0.653 | r = 0.164<br>p = 0.792 | r = 0.661<br>p = 0.225 | | r = 0.430<br>p = 0.470 | r = 0.822<br>p = 0.088 | r = 0.364<br>p = 0.547 | r = 0.357<br>p = 0.556 | r = 0.006<br>p = 0.992 | r = 0.720<br>p = 0.171 | |
| Actin | r = 0.546<br>p = 0.341 | r = 0.684<br>p = 0.203 | r = 0.308<br>p = 0.614 | r = 0.298<br>p = 0.626 | r = 0.390<br>p = 0.610 | r = 0.385<br>p = 0.522 | r = 0.321<br>p = 0.599 | r = 0.727<br>p = 0.164 | r = 0.200<br>p = 0.747 | r = 0.430<br>p = 0.470 | | r = 0.331<br>p = 0.587 | r = 0.825<br>p = 0.090 | r = 0.389<br>p = 0.517 | r = 0.011<br>p = 0.986 | r = 0.108<br>p = 0.863 | |
| Bcl2 | r = 0.422<br>p = 0.479 | r = 0.824<br>p = 0.066 | r = 0.922<br>p = 0.026 | r = 0.961<br>p = 0.009 | r = 0.757<br>p = 0.243 | r = 0.082<br>p = 0.898 | r = 0.738<br>p = 0.155 | r = 0.360<br>p = 0.552 | r = 0.255<br>p = 0.679 | r = 0.822<br>p = 0.088 | r = 0.331<br>p = 0.587 | | r = 0.404<br>p = 0.500 | r = 0.715<br>p = 0.174 | r = 0.532<br>p = 0.356 | r = 0.893<br>p = 0.042 | |
| Mos | r = 0.615<br>p = 0.270 | r = 0.811<br>p = 0.096 | r = 0.582<br>p = 0.304 | r = 0.522<br>p = 0.367 | r = 0.613<br>p = 0.387 | r = 0.054<br>p = 0.931 | r = 0.580<br>p = 0.306 | r = 0.651<br>p = 0.234 | r = 0.222<br>p = 0.720 | r = 0.364<br>p = 0.547 | r = 0.825<br>p = 0.085 | r = 0.404<br>p = 0.500 | | r = 0.159<br>p = 0.798 | r = 0.013<br>p = 0.983 | r = 0.420<br>p = 0.481 | |
| GSH | r = 0.128<br>p = 0.838 | r = 0.366<br>p = 0.545 | r = 0.701<br>p = 0.187 | r = 0.730<br>p = 0.161 | r = 0.473<br>p = 0.527 | r = 0.256<br>p = 0.678 | r = 0.614<br>p = 0.271 | r = 0.844<br>p = 0.072 | r = 0.074<br>p = 0.905 | r = 0.357<br>p = 0.556 | r = 0.389<br>p = 0.517 | r = 0.715<br>p = 0.174 | r = 0.159<br>p = 0.798 | | r = 0.659<br>p = 0.227 | r = 0.763<br>p = 0.134 | |
| Bax | r = 0.506<br>p = 0.385 | r = 0.445<br>p = 0.377 | r = 0.370<br>p = 0.470 | r = 0.395<br>p = 0.438 | r = 0.887<br>p = 0.113 | r = 0.617<br>p = 0.140 | r = 0.760<br>p = 0.136 | r = 0.421<br>p = 0.480 | r = 0.264<br>p = 0.667 | r = 0.006<br>p = 0.992 | r = 0.011<br>p = 0.986 | r = 0.532<br>p = 0.356 | r = 0.013<br>p = 0.983 | r = 0.659<br>p = 0.227 | | r = 0.332<br>p = 0.586 | |
| P27Kip1 | r = 0.498<br>p = 0.393 | r = 0.724<br>p = 0.167 | r = 0.950<br>p = 0.013 | r = 0.955<br>p = 0.011 | r = 0.704<br>p = 0.296 | r = 0.493<br>p = 0.398 | r = 0.711<br>p = 0.179 | r = 0.396<br>p = 0.509 | r = 0.12<br>p = 0.985 | r = 0.720<br>p = 0.171 | r = 0.108<br>p = 0.863 | r = 0.893<br>p = 0.042 | r = 0.420<br>p = 0.481 | r = 0.763<br>p = 0.134 | r = 0.332<br>p = 0.586 | | |
| p21 | | | | | | | | | | | | | | | | | |

Figure 13A
RT112 Human Bladder Cancer- Treated
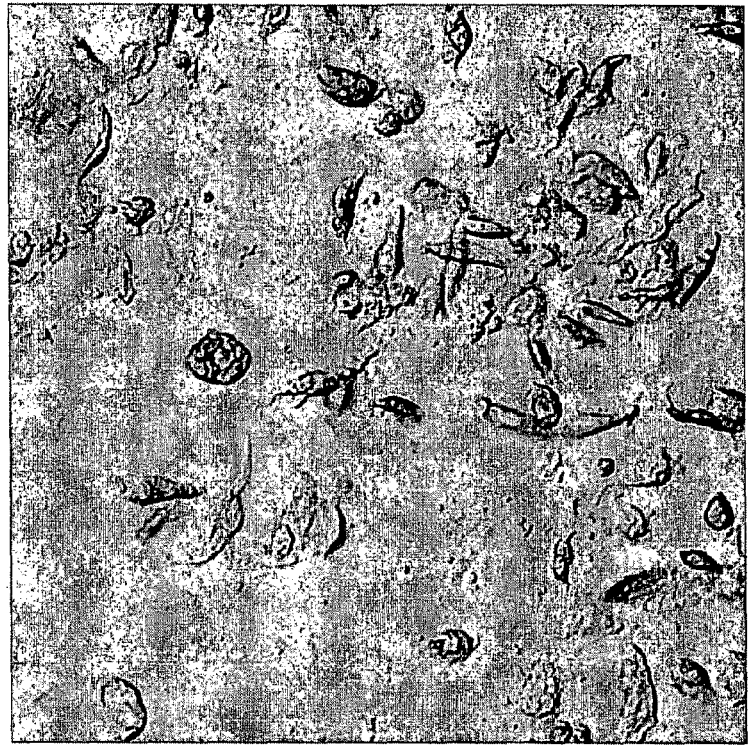
Control
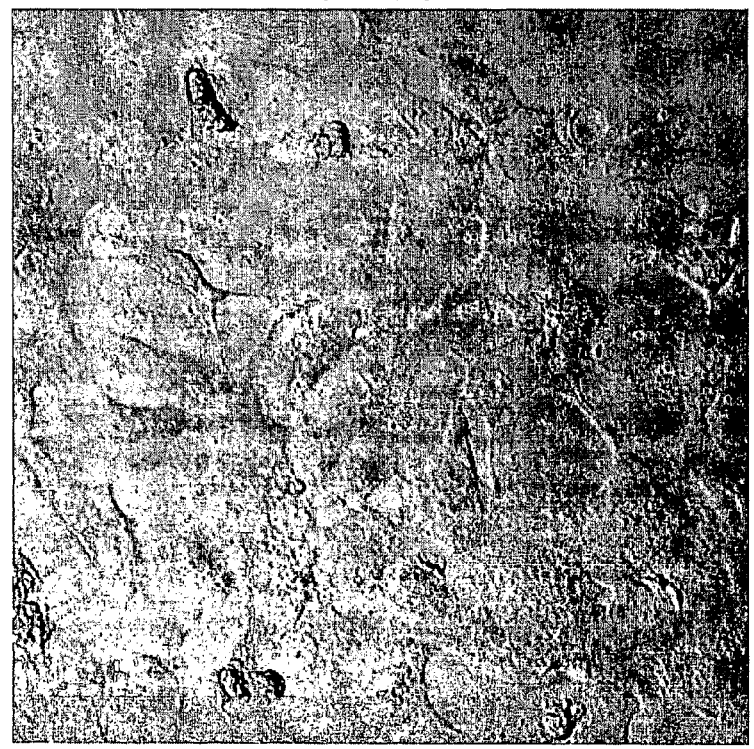

Figure 13B
HT29 Human Colon Cancer - Treated
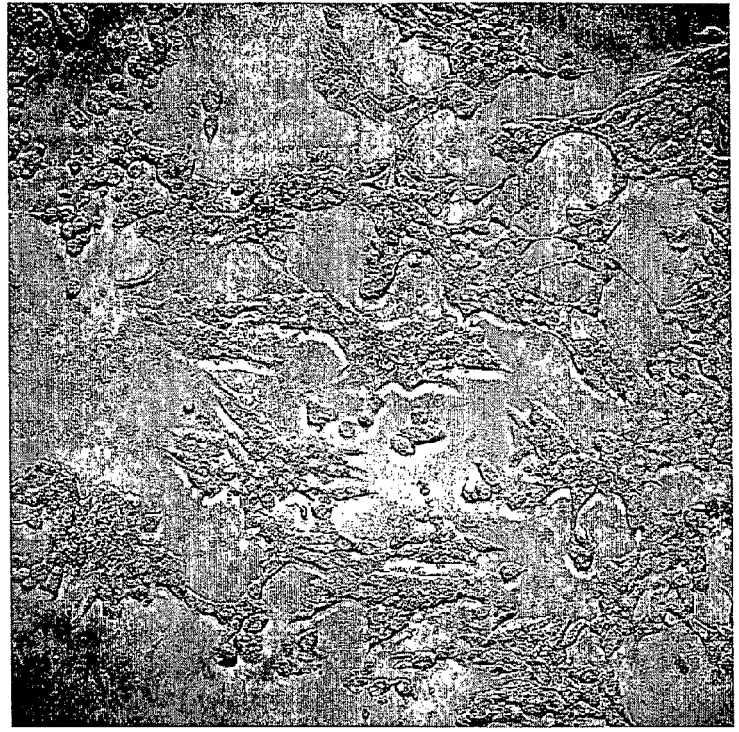
Control
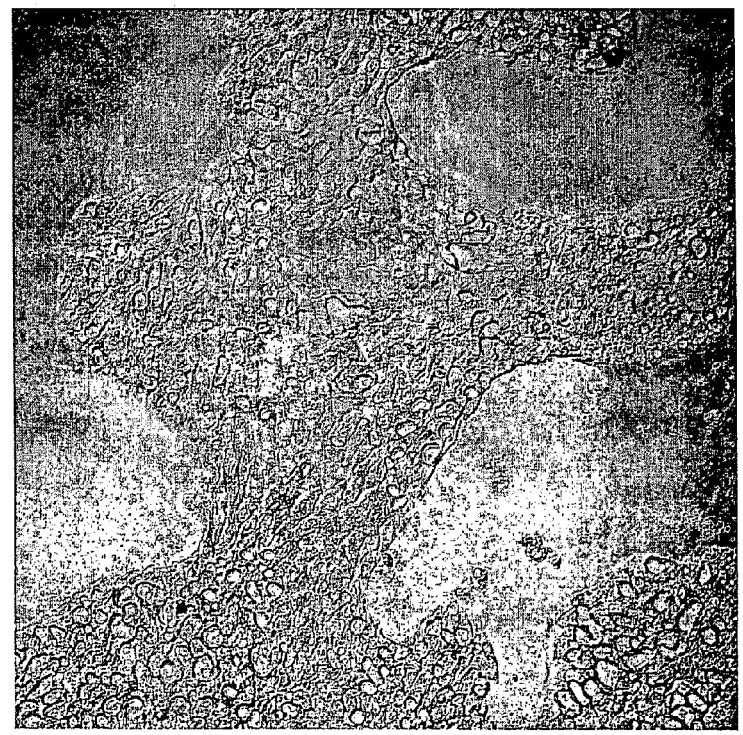

Figure 14
Normal Fibroblast plus CDK4 decapeptide
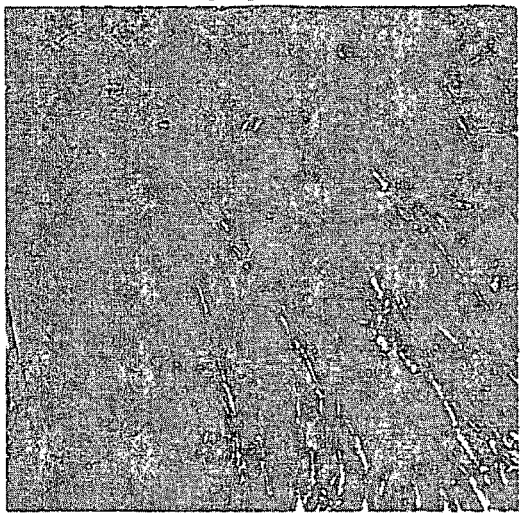
Normal Fibroblast plus nonsense control
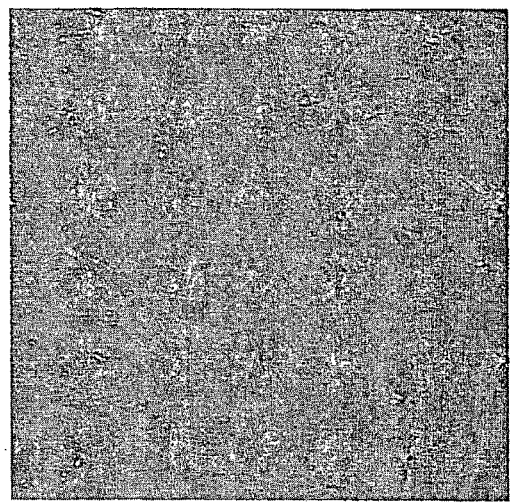
MGHU-1 Bladder cancer plus CDK4 decapeptide
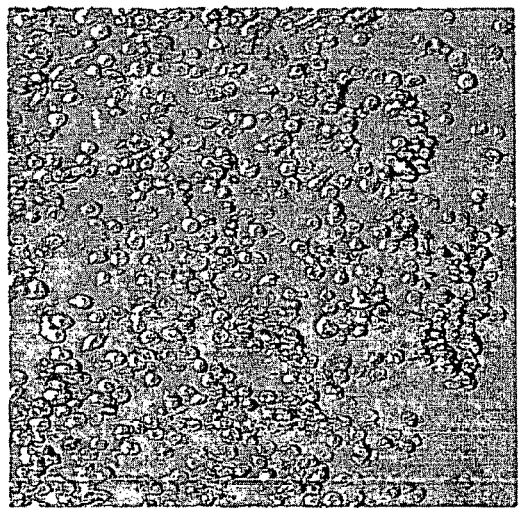
MGHU-1 Bladder cancer plus nonsense control
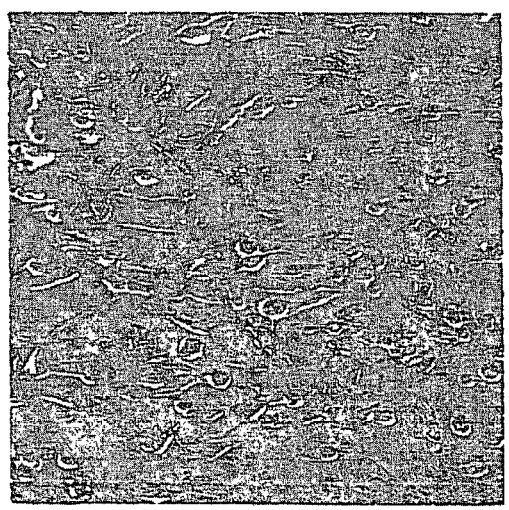

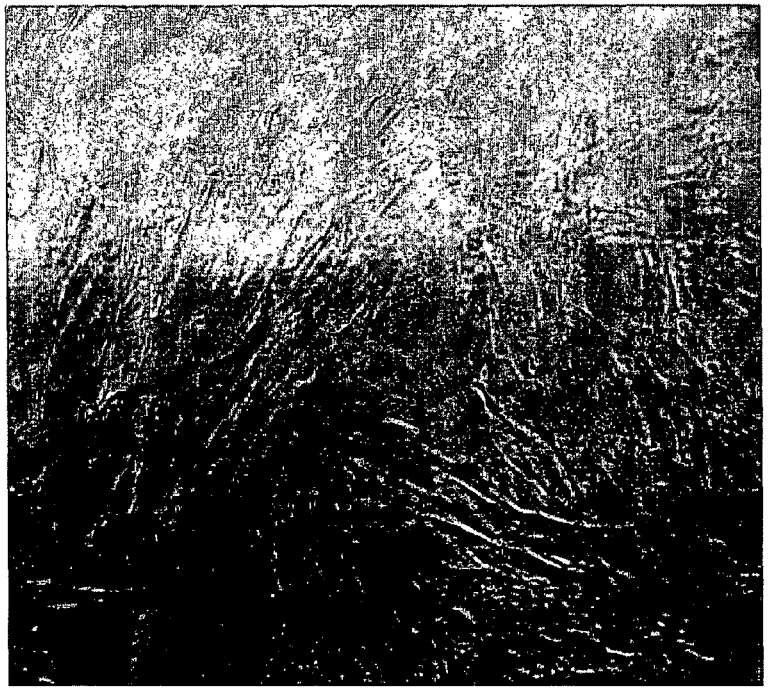
Figure 18

Figure 19
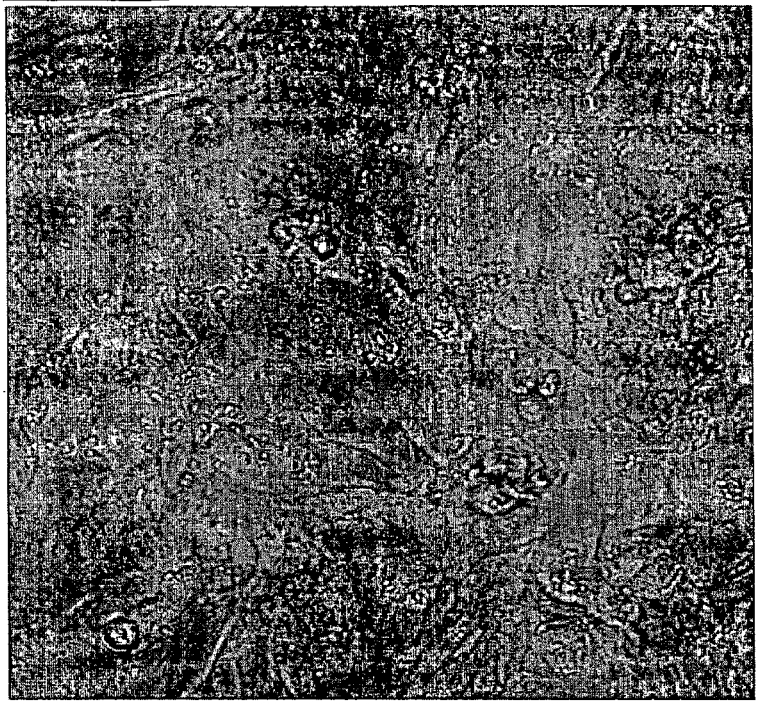
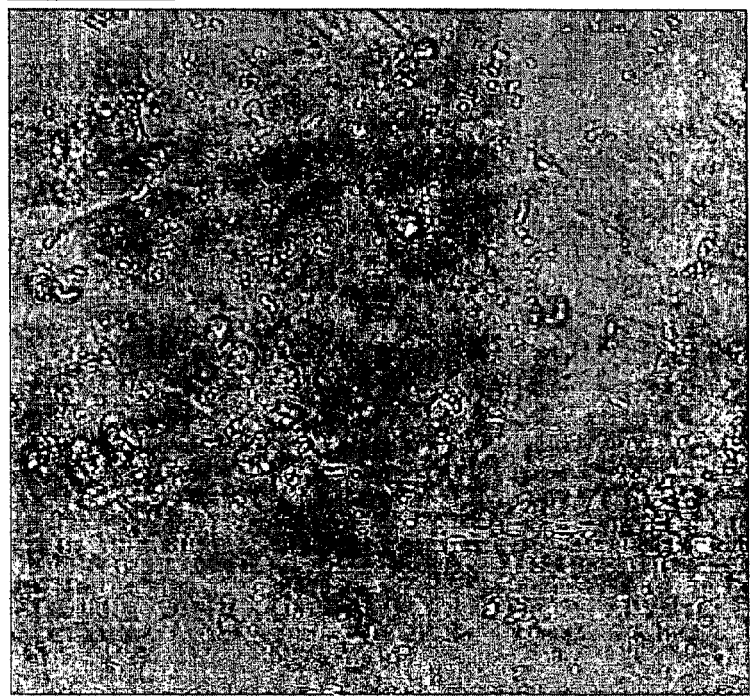

TREATING CANCER

FIELD OF THE INVENTION

The present invention relates to peptides and peptide mimetics that are cytotoxic to, and/or inhibiting to the growth of, a cancer cell and/or stimulating to the growth of a non-cancerous cell and/or a control cell. The present invention also relates to medical uses of such peptides and peptide mimetics.

BACKGROUND TO THE INVENTION

Although chemotherapy has been responsible for curing many people of cancer, there still remain a large number of patients whose tumours either show little response to treatment, or respond initially only to recur later. For these patients the current treatments are clearly inadequate.

It is thought that certain tumours are unresponsive to conventional chemotherapy because the cells of these tumours have a pattern of gene expression that renders them insensitive to chemotherapeutic agents. Similarly, it is thought that tumours often respond initially to chemotherapy, but subsequently become resistant because the cells of the tumour exhibit tumour heterogeneity and genetic instability. Tumour heterogeneity describes the situation where different cells in the tumour have different patterns of gene expression with some cells being resistant to a chemotherapeutic agent, whilst other cells are sensitive to this agent. Treating such a tumour with this chemotherapeutic agent therefore kills the sensitive cells, resulting in tumour shrinkage, but fails to kill the resistant cells, which continue dividing to produce a cancer that is wholly drug resistant.

In addition most conventional chemotherapeutic agents developed up to the present time generally inhibit the growth of important normal cells, for example: a) chemotherapeutic inhibition of the progenitor cells of the haemopoietic system resulting in a fall of red blood cells, white blood cells and platelets causing anaemia, susceptibility to infection and spontaneous bleeding b) inhibition of replacement of normal cells in the bowel causing diarrhea or c) inhibition of replacement of squamous cells lining the mouth, nose and throat etc.

Genetic instability is found in the majority of cancers. It results in the tumour cells acquiring new mutations. Certain of these mutations may confer drug resistance to the cells in which they occur. These drug resistant cells survive chemotherapy and divide to produce a cancer that is drug resistant.

There is thus a need for anticancer agents which are effective against all cancer cells, which are not affected by tumour heterogeneity and genetic instability and which do not inhibit growth of normal (non-cancerous) cells or which may even promote normal non-cancerous cell growth.

WO 03/081239, which is hereby incorporated in its entirety by reference, identifies gene products, termed critical normal gene products, which are required for cancer cell survival and proliferation. Because critical normal gene products are required for cancer cell survival and proliferation, they must be present and functioning in every tumour cell and therefore provide a consistent anti-cancer drug target that is unaffected by tumour heterogeneity and genetic instability. WO 03/081239 teaches that agents that disrupt critical normal gene products provide effective anti-cancer agents. Although generic methods for disrupting critical normal gene products were disclosed, WO 03/081239 did not disclose any agent that could successfully treat cancer.

Critical normal gene products should also, by definition, not disrupt the function of normal cells. Thus, conventional chemotherapy in the clinic is non-selective and thus consistently damages normal non-cancerous cells and is only effective against non-resistant cancer cells.

An ideal anticancer agent would inhibit the growth of most, if not all, types of cancer cell growth but have no effect on, or even stimulate, normal non-cancerous cell growth.

WO 03/081239 identified CDK4 protein as a critical normal gene product that is present in most (if not all) cancers.

CDK4 protein is known to regulate entry into S phase of the cell cycle by initiating the events needed for the cell to enter S phase. More particularly, activated CDK4 phosphorylates pRb and related proteins p107 and p130. In their hypophosphorylated state these proteins bind E2F transcription factors. However, upon phosphorylation, the E2F transcription factors are released as heterodimers with the proteins DP-1/DP-2. The E2F/DP heterodimers then bind to DNA and activate factors required for DNA synthesis (an activity that takes place during S phase). In addition, free E2F protein upregulates genes controlling cell division such as cyclin E, cyclin A, CDK1 and E2Fs, thereby progressing the cell cycle.

CDK4 protein is only activated when conditions for entry into S phase are suitable and positive signal transduction pathways relaying signals from cell surface receptors such as the Ras/Raf/Erk pathway have been demonstrated to affect CDK4 activation. CDK4 protein is activated by phosphorylation of threonine 164 but inhibited by phosphorylation of tyrosine 17.

To enable it to perform its role, CDK4 protein is known to have many functions including binding cyclin D1, phosphorylating pRb, binding to CDK inhibitors such as p21, p27, p16, binding to cyclin activating kinase and interacting with the enzymes responsible for phosphorylating and dephosphorylating tyrosine 17.

Because of its role in promoting cell division, several studies have investigated the role of CDK4 protein in cancer.

Knockout mice lacking CDK4 protein do not develop cancer following induction with a classical system of initiator (DMBA) followed by promoter (TBA i.e. phorbol ester) (Robles et al. (1998) Genes Dev. 12: 2469; Rodriguez-Puebla et al. (2002) Am. J. Path. 161: 405). No other knockout (including a cyclin D1 knockout) has such a marked effect on cancer development.

However, the CDK4 protein is typically over-expressed in cancer cells. In addition, transgenic mice overexpressing CDK4 protein are more readily induced to develop cancer using the carcinogenesis induction system mentioned above (Robles et al. (1998) Genes Dev. 12: 2469; Rodriguez-Puebla et al. (2002) Am. J. Path. 161: 405).

Moreover, transfection of normal CDK4 has been shown to cause extension of proliferative lifespan in normal human fibroblasts (Morris et al. (2002) Oncogene 21, 4277)

In view of the apparent importance of CDK4 protein in cancer, it has been proposed to be an anticancer target. However, drugs that inhibit CDK4 kinase activity (such as flavopiridol) have very little clinical effect in phase II studies.

SUMMARY OF THE INVENTION

The present invention improves on the prior art by providing effective anti cancer agents that target the CDK4 protein.

More particularly, the invention provides a peptide comprising an amino acid sequence that is part of the amino acid sequence of a CDK4 protein, or homologous to part of the amino acid sequence of CDK4 protein, which peptide is cytotoxic to, and/or inhibiting to the growth of, a cancer cell and/or stimulating to the growth of non-cancerous cells and/or control cells. In a preferred embodiment of the present invention the peptide is non-inhibitory to the growth of non-cancerous cells and/or control cells. Preferably, the CDK4 protein is human CDK4 protein.

The term peptide is well known in the art and refers to a molecule comprising a linear sequence of amino acid residues. Proteins, such as the CDK4 protein, also comprise linear sequences of amino acid residues. The peptide of the present invention may therefore comprise a part of the amino acid sequence of CDK4 protein. That is to say, the peptide comprises a fragment of the CDK4 protein.

In one embodiment, the peptide comprises shorter linear sequences within the unique partially hydrophobic region located externally in the c-terminal portion of the CDK4 molecule (vide infra) and cyclic peptides derived from these same sequences which inhibit the growth of human cancer cells. Preferably, this peptide is non-inhibitory to the growth of non-cancerous cells and/or control cells. Optionally, this peptide stimulates the growth of non-cancerous cells and/or control cells.

In a preferred embodiment, the peptide comprises the amino acid sequence set out in SEQ ID NO:1. In a particularly preferred embodiment, the peptide consists of the amino acid set out in SEQ ID NO:1.

Alternatively, the peptide may comprise an amino acid sequence that is homologous to a part of the amino acid sequence of CDK4 protein. In a preferred embodiment, the peptide comprises the amino acid sequence set out in SEQ ID NO:2. In a particularly preferred embodiment, the peptide consists of the amino acid sequence set out in SEQ ID NO:2.

In one embodiment, the peptide comprises an amino acid sequence having the general formula ZRGXRZ (SEQ ID NO:32), wherein R is arginine, G is glycine, Z may be present or absent and at least one Z is present, X and Z are proline or threonine and at least one of X and/or Z is proline. In a preferred embodiment X and Z are proline. It is preferred that the peptide comprises an amino acid sequence selected from PRGPRP (SEQ ID NO: 5), PRGPR (SEQ ID NO: 6), RGPRP (SEQ ID NO: 7), RGPR (SEQ ID NO: 8), TRGPRP (SEQ ID NO: 9), TRGTRP (SEQ ID NO: 10), TRGTRT (SEQ ID NO: 11), PRGTRP (SEQ ID NO: 12), PRGPRT (SEQ ID NO: 13), PRGTRT (SEQ ID NO: 14), TPPRGPRP (SEQ ID NO: 15) and PPRGPRP (SEQ ID NO: 16). The peptide may also consist of these amino acid sequences. These peptides are particularly preferred because they are cytotoxic to cancer cells tested and some were also selectively cytotoxic to cancer cells and non-inhibitory to the growth of non-cancerous cells tested.

In one embodiment, the peptide comprises an amino acid sequence having the general formula PRXXRP (SEQ ID NO:33), wherein P is proline, R is arginine and X is any amino acid or an amino acid mimetic. An amino acid mimetic is an organic molecule exhibiting similar properties to a natural amino acid. It is particularly preferred that the peptide comprises an amino acid sequence selected from PPRGPRP (SEQ ID NO:16), PRGPRP (SEQ ID NO: 5), PPRXPRP (SEQ ID NO:34), PRXPRP (SEQ ID NO:35), PPRGXRP (SEQ ID NO:36), PRGXPRP (SEQ ID NO:37), PPRXXRP (SEQ ID NO:38) and PRXXRP (SEQ ID NO:39). The peptide may also consist of these amino acid sequences.

These peptides having high proline and arginine density exhibit improved potency, possibly because of improved cell uptake and closer target specificity.

In one embodiment, the peptide is linear or cyclic and comprises:
n amino acid sequences having the general formula [(ZRGXRZ)V] (SEQ ID NO:40), wherein R is arginine, G is glycine, Z may be present or absent and at least one Z is present, X and Z are proline or threonine and at least one of X and/or Z is proline, V is valine and may be present or absent and n is an integer from 1-10;
and m further amino acid sequences, each further sequence independently having z amino acids, wherein m is an integer from 0-10 and z is an integer from 1-20.

When m is 1 or more, the further sequence(s) may be arranged randomly with the n amino acid sequences having the general formula [(ZRGXRY) Z] (SEQ ID NO:40). Alternatively, the further sequence(s) may be arranged alternately with each amino acid sequence having the general formula [(ZRGXRZ)V] (SEQ ID NO:40). In another alternative, the further sequence(s) may be arranged so that the n amino acid sequences having the general formula [(ZRGXRZ)V] (SEQ ID NO:40) are directly adjacent in sequence to one another and the m further amino acid sequences of z amino acids are directly adjacent in sequence to one another. In a preferred embodiment X and Z are proline.

In the further amino acid sequence(s) each of the z amino acids in the sequence may be any amino acid. However, preferably the amino acids of these further sequence(s) are selected from glycine, alanine, valine, phenylalanine, proline and glutamine. Preferably, the further amino acid sequences comprise hydrophobic amino acids.

In preferred embodiments n is 1, 2, 3, 4 or 5. In a more preferred embodiment n is 3.

It is also preferred that m is 1, 2, 3, 4 or 5. Most preferably, m is 1 or 2.

In preferred embodiments z is from 2-14, more preferably 2-11 and most preferably 2, 3, 4, 6 or 12. Particularly preferred further sequence(s) include GG, GGG, GGGG (SEQ ID NO:41), GGGGG (SEQ ID NO:42), GGGGGG (SEQ ID NO:43), AA, AAA, AAAA (SEQ ID NO:44), AAAAA (SEQ ID NO:45), AAAAAA (SEQ ID NO:46), VV, VVV, VVVV (SEQ ID NO:47), VVVVV (SEQ ID NO:48), VVVVVV (SEQ ID NO:49) or combination of these.

It is preferred that the peptide is cyclic.

In a preferred embodiment when the peptide comprises n amino acid sequences having the general formula [(ZRGXRZ)V] (SEQ ID NO:40) and m further amino acid sequences of z amino acids, the peptide comprises an amino acid sequence selected from the following:

SEQ ID NO: 18    [GGGGPRGPRPGGGAAA]

SEQ ID NO: 19    [GGGGPRGPRPGGGGPRGPRPVPRGPRPV]

SEQ ID NO: 20    [FPPRGPRPVQFPPRGPRPVQFPPRGPRPVQ]

SEQ ID NO: 21    [AAAGGPRGPRPGGGAAA]

SEQ ID NO: 22    [AAGGGPRGPRPGGGAA]

SEQ ID NO: 23    [AAAGGGPRGPRPGGGAAA]

SEQ ID NO: 24    [AVAGGGPRGPRPGGGAVA]

SEQ ID NO: 25    [GGGGGGPRGPRPGGGGGG]

SEQ ID NO: 26    [AAAAAAPRGPRPAAAAAA]

SEQ ID NO: 27    [AAAAPRGPRPAAAAVVVV]

SEQ ID NO: 28    [AAGPGPGPRGPRPGPGAA]

SEQ ID NO: 29    [AAGPGGPRGPRPGGPGAA]

SEQ ID NO: 30    [AAVPGGPRGPRPGGPGVAAV]

SEQ ID NO: 31    [GGPRGPRPGGPRGPRPGGPRGPRP]

It is particularly preferred that the amino acids sequences SEQ ID NOs:18-31 are cyclic amino acid sequences.

These peptides are particularly preferred because they comprise the sequence PRGPRP (SEQ ID NO:5), which has been shown to be cytotoxic to cancer cells tested and also selectively cytotoxic to cancer cells and non-inhibitory to the growth of non-cancerous cells tested. Further, these peptides are particular preferred because they are designed to penetrate cells more successfully by including hydrophobic (—CH3) groups. Still further, when these peptides are cyclic they are likely to penetrate cells more successfully. These peptides also provide the most effective balance between flexibility and conformational restraint of the PRGPRP (SEQ ID NO:5) sequence.

When m is 0 (ie no further amino acid sequence(s) are present) it is preferred that the peptide comprises the amino acid sequence PRGPRPVPRGPRPVPRGPRPV (SEQ ID NO: 17). The peptide may also consist of the amino acid sequence PRGPRPVPRGPRPVPRGPRPV (SEQ ID NO:17). In a more preferred embodiment, the peptide is a cyclic peptide comprising the amino acid sequence PRGPRPVPRGPRPVPRGPRPV (SEQ ID NO: 17). The cyclic peptide may also consist of the amino acid sequence PRGPRPVPRGPRPVPRGPRPV (SEQ ID NO:17).

In the context of this invention, the term homology means a percentage sequence identity. In other words, it refers to the percentage of amino acid residues that are identical in the CDK4 protein and peptide, on alignment of their amino acid sequences. Preferably, the percentage sequence identity is at least 50%. More preferably, the percentage sequence identity is at least 60%, 70%, 80% or 90%.

The term "part" indicates that the peptide does not contain the entire amino acid sequence of CDK4. Typically, the peptide comprises at least 5 amino acids that are identical or homologous to an amino acid sequence present in the CDK4 protein. Preferably, the peptide comprises at least 10 amino acids that are identical or homologous to an amino acid sequence present in the CDK4 protein.

The peptide of the present invention is cytotoxic to, or inhibiting to the growth of, a cancer cell and/or stimulating to the growth of a non-cancerous and/or control cell. In this context, a cancer cell is a cell taken from a primary tumour, a metastasis or other suspected site of cancer in a subject, or a cell line derived from a cancer. It is preferred that the peptide is more cytotoxic to, or more inhibiting to the growth of a cancer cell than a non-cancerous cell and/or a control cell. In a preferred embodiment of the present invention the peptide is non-inhibitory to the growth of non-cancerous cells and/or control cells.

In the context of this invention, non-cancerous cells are any normal (healthy) cells i.e. cells not affected by cancer and may be cells of any tissue of a patient. A control cell includes a normal non-cancerous cell used to measure cytotoxicity against and may be derived from the corresponding normal tissue of a patient, from any other normal tissue of a patient or from a primary cell culture. Thus, in many cases a non-cancerous cell and a control cell may be the same, both being a normal healthy cell. Typically, human fibroblasts or keratinocytes in short term primary culture are non-cancerous cells and used as control cells.

Cancer cells can be identified by measuring the expression levels of the CDK1 and CDK4 gene products, as disclosed in WO99/42821. A cell sample is cancerous if the ratio of the expression levels of the CDK1 and CDK4 proteins is in the range 0.6 to 1.6.

Optionally the peptide may comprise an amino acid sequence facilitating cellular uptake of the peptide. Such amino acid sequences are well known in the art. These include Penetratin™ (RQIKIWFQNRJRMKWKK (SEQ ID NO:50); Derossi et al. Trends Cell Biol. (1998) 8: 84-87). Certain variants of the Penetratin™ amino acid sequence are also known to be effective at facilitating cellular internalization as described in Christiaens et al. (European J. Biochemistry (2004) 271:1187). Other cellular internalization amino acid sequences include KKWKMRRNQFWVKVQRG (SEQ ID NO:51) (Kanovsky et al. Proc. Natl. Acad. Sci., USA (2001) 98: 12438-43), polyarginine (11 residues; Wu et al. (2003) Neurosci. Res. 47: 131-135) and LTVSPWY (SEQ ID NO:52) (Shadidi M. and Sioud M. Identification of novel carrier peptides for the specific delivery of therapeutics into cancer cells FASEB J 17 (2003) 256-258).

In one embodiment, the peptide consists of an amino acid sequence that is part of the amino acid sequence of CDK4 protein, or an amino acid sequence that is homologous to a part of the amino acid sequence of CDK4 protein, and optionally an amino acid sequence facilitating cellular uptake of the peptide.

The invention also provides peptide mimetics capable of functionally mimicking peptides according to the invention, which peptide mimetics are cytotoxic to, or inhibiting to the growth of a cancer cell. It is preferred that the peptide mimetic is more cytotoxic to, or more inhibiting to the growth of a cancer cell than a non-cancerous cell and/or a control cell. In a preferred embodiment the peptide mimetic is non-inhibitory to the growth of normal non-cancerous cells and/or control cells. Optionally, the peptide mimetic stimulates the growth of normal non-cancerous cells and/or control cells.

In a further aspect of the invention, medical uses of the peptides and peptide mimetics are provided. For example, the invention provides a pharmaceutical composition comprising a peptide or peptide mimetic as described above and a carrier, diluent or excipient known in the art. In a preferred embodiment, this pharmaceutical composition also comprises a p53 inhibitor. In an alternative preferred embodiment this pharmaceutical composition also comprises stem cells.

In the context of this invention, a p53 inhibitor is a factor capable of inhibiting production of p53 protein or inhibiting the activity of p53 protein. p53 inhibitors are well known in the art and include MDM2 protein, fragments of the MDM2 protein and pifithrin-α.

A method of manufacturing a pharmaceutical composition is also provided. The method comprises providing a peptide or peptide mimetic and manufacturing a pharmaceutical composition comprising this peptide/peptide mimetic. Where the pharmaceutical composition contains a p53 inhibitor, this is incorporated into the pharmaceutical composition during manufacture. Where the pharmaceutical composition contains stem cells, this is incorporated into the pharmaceutical composition during manufacture.

The invention also provides a method of treating a patient having a cancer, which method comprises treating the patient with this pharmaceutical composition. Where the cancer contains cells expressing wild type p53, it is preferred that the patient is treated with a pharmaceutical composition comprising a p53 inhibitor.

The pharmaceutical composition of the present invention is effective in treating cancers of various origins, including breast cancer, prostate cancer, colorectal cancer, bladder cancer, ovarian cancer, endometrial cancer, cervical cancer, head and neck cancer, stomach cancer, pancreatic cancer, oesophagus cancer, small cell lung cancer, non-small cell lung cancer, malignant melanomas, neuroblastomas, leukaemias, lymphomas, sarcomas and gliomas. As discussed above, cancer cells can be identified by the method of WO 99/42821. Cancer cells are for example cells in which the ratio of the expression levels of the CDK1 and CDK4 proteins is in the range 0.6 to 1.6.

The present invention also provides a peptide or peptide mimetic for use in medicine. In addition, it provides a combined preparation comprising the peptide or peptide mimetic and a p53 inhibitor for simultaneous separate or sequential use in medicine.

The invention also provides the use of a peptide/peptide mimetic in the manufacture of a medicament for the treatment of cancers, and the use of a peptide/peptide mimetic and p53 inhibitor in the manufacture of a combined preparation for simultaneous, separate or sequential use in the treatment of cancers, including those mentioned above. Again, if the cancer contains cells that express wild type p53, it is preferred that this is treated with a combined preparation comprising a p53 inhibitor.

Cancer cells expressing wild type p53 (i.e. p53 containing no mutations) can be identified by methods known in the art. For example, wild type p53 may be identified by DNA sequencing, or by immunochemistry using antibodies specifically distinguishing between mutant p53 protein and wild type p53 protein.

In degenerative disorders the cells comprising the particular tissue cells undergo cell death at an earlier time than similar cells in a normal healthy individual. It is known from Morris et al (Morris et al. (2002) Oncogene 21, 4277) that normal CDK4 may be capable of extending the survival of non-cancerous cells. It has been shown by the inventors of the present invention that the peptides of the present invention, particularly peptides having the amino acids sequence set out in SEQ ID NO:17, cause proliferation of normal non-cancerous cells. Therefore, peptides of the present invention are of benefit in the treatment of many degenerative disorders in which cells of particular tissues die earlier than they should in the affected individual.

Therefore, the present invention also provides a method of treating a patient having a degenerative disorder, which method comprises treating the patient with the pharmaceutical composition of the present invention. It is preferred that the patient is treated with the pharmaceutical composition further comprising stem cells.

This method of treatment of a degenerative disorder may be in combination with stem cell therapy or as an adjunct to improve the efficacy of stem cell therapy. At the present time stem cell therapy is widely believed to be able to cause improvement in disorders due to inappropriately early cell death. Stem cells are normal cells which have not fully differentiated or senesced and when implanted into tissues in which cell damage has occurred are capable of proliferating to replace the dead cells. Peptides of the present invention, particularly peptides having the amino acid sequence set out in SEQ ID NO: 17, and/or similar molecules stimulate the growth of stem cells and extend their mortality making them even more effective in replacing the damaged cells of degenerative disorders.

The pharmaceutical composition of the present invention is effective in treating degenerative disorders when the pharmaceutical composition comprises the peptide or peptide mimetics of the present invention which are capable of stimulating the growth of non-cancerous and/or control cells. This pharmaceutical composition is effective in treating degenerative disorders including alzheimer's disease, muscular dystrophy, macular degeneration, early onset diabetes due to loss of beta cells in the pancreas, traumatic spinal cord damage, motor neurone disease and cystic fibrosis.

In a preferred embodiment, the pharmaceutical composition of the present invention effective in treating degenerative disorders comprises the peptide of the present invention comprising n amino acid sequence(s) having the general formula [(ZRGXRZ)V] (SEQ ID NO:40), wherein R is arginine, G is glycine, Z may be present or absent and at least one Z is present, X and Z are proline or threonine and at least one of X and/or Z is proline, V is valine and may be absent or present and n is an integer from 1-10, more preferably the peptide is a cyclic peptide comprising the amino acid sequence PRG-PRPVPRGPRPVPRGPRPV (SEQ ID NO: 17), still more preferably the peptide is a cyclic peptide consisting of the amino acid sequence PRGPRPVPRGPRPVPRGPRPV (SEQ ID NO: 17).

The present invention provides a combined preparation comprising the peptide or peptide mimetic of the present invention which is capable of stimulating the growth of non-cancerous and/or control cells and stem cells for simultaneous separate or sequential use in medicine.

The invention also provides the use of the peptide or peptide mimetic of the present invention which is capable of stimulating the growth of non-cancerous and/or control cells in the manufacture of a medicament for the treatment of a degenerative disorder, The invention also provides the use of the peptide or peptide mimetic of the present invention which is capable of stimulating the growth of non-cancerous and/or control cells and stem cells in the manufacture of a combined preparation for simultaneous, separate or sequential use in the treatment of a degenerative disorder.

Those skilled in the art could determine suitable administration regimens for the peptide or peptide mimetic of the present invention. The precise administration regimen will depend upon the physicochemical properties of the peptide or peptide mimetic. For example, a prolonged administration of peptides having the amino acid sequences SEQ ID NO: 1 and SEQ ID NO:2 is required since experimental evidence indicates that cancer cells may need to be incubated in the presence of the peptide from one week up to three weeks for an effect on viability to be observed.

Peptides or peptide mimetics of the present invention may be identified by a screening method which comprises providing a peptide comprising an amino acid sequence that is part of the amino acid sequence of CDK4, or homologous to part of the amino acid sequence of CDK4, or a peptide mimetic capable of functionally mimicking such a peptide, followed by treating a cancer cell sample with the peptide or peptide mimetic and determining the cytotoxic effect of, and/or the growth inhibiting effect of this peptide or peptide mimetic on this sample. The method also involves a step of identifying a peptide or peptide mimetic that is effective in the treatment of cancer as a peptide or peptide mimetic that is cytotoxic to, or inhibiting to the growth of, the cancer cell sample. Optionally, a step of producing the identified peptide or peptide mimetic may follow.

In a preferred embodiment, the method further comprises treating a control cell sample with the peptide or peptide mimetic and determining the cytotoxic effect of, and/or the growth inhibiting effect of this peptide or peptide mimetic on this sample. A peptide or peptide mimetic that is effective in the treatment of cancer is a peptide or peptide mimetic that more cytotoxic to, or more inhibiting to the growth of, a cancer cell sample than a control cell sample.

In a preferred embodiment, the method also involves a step of treating a control cell sample with the peptide or peptide mimetic and determining whether the identified peptide or peptide mimetic is non-inhibitory to the growth of a control cell sample and optionally determining whether the identified peptide or peptide mimetic is stimulating to the growth of a control cell sample. A peptide or peptide mimetic that is advantageous in the treatment of cancer is a peptide or peptide mimetic that is non-inhibitory to the growth of a control cell sample and may also be stimulating to the growth of a control cell sample. A peptide or peptide mimetic that is advantageous in the treatment of degenerative disorders is a peptide or peptide mimetic that is stimulating to the growth of a control cell.

Cancer cells, control cells and non-cancerous cells have been defined above. Appropriate culture conditions for such cells are known in the art. Typically then, the step of treating a cancer cell sample and a control cell sample with the peptide or peptide mimetic and determining the cytotoxic effect of, and/or the growth inhibiting effect of these, simply comprises adding the test peptide or test peptide mimetic to the culture medium. Controls are preferably included. These may include adding no test peptide/peptide mimetic to samples of cells or adding a peptide/peptide mimetic known to have no affect on viability.

Methods of determining whether a peptide or peptide mimetic is cytotoxic or growth inhibiting to a cell sample are well known to those skilled in the art. These include inspection of treated and untreated cell samples using phase contrast microscopy, the MTT cytotoxicity assay (Roche Molecular Biochemicals, Indianopolis, Ill., USA), the propidium iodide staining assay (Do et al. Oncogene (2003) 22:1431-1444), cell death detection ELISA (Roche Molecular Biochemical, Indianopolis, Ill., USA), the caspase activity assay (Clontech, Palo Alto, Calif., USA) and the CytoTox96 non-radioactive cytotoxicity assay (Promega, Madison, Wis., USA).

BRIEF DESCRIPTION OF FIGURES

The invention will be further described by way of example only with reference to the following figures:

FIG. 1 shows the correlation in expression levels of 17 proteins whose normal role is the control of cell division, differentiation senescence and programmed cell death in normal human keratinocytes.

FIG. 2 shows the correlation in expression levels of 17 proteins whose normal role is the control of cell division, differentiation senescence and programmed cell death in 20 human cancer cell lines.

FIG. 4 shows the correlation in expression levels of 17 proteins whose normal role is the control of cell division, differentiation senescence and programmed cell death in 20 human cancer cell lines containing wild type p53 protein.

FIG. 5 shows the correlation in expression levels of 17 proteins whose normal role is the control of cell division, differentiation senescence and programmed cell death in 20 human cancer cell lines containing mutant p53 protein.

FIG. 13A shows RT112 cells that have been treated with a peptide having the amino acid sequence set out in SEQ ID NO:1, and RT112 cells that have been treated with a peptide having the amino acid sequence set out in SEQ ID NO:4. FIG. 13B shows HT29 cells that have been treated with a peptide having the amino acid sequence set out in SEQ ID NO:1, and HT29 cells that have been treated with a peptide having the amino acid sequence set out in SEQ ID NO:4.

FIG. 14 shows normal human fibroblasts and MGHU-1 cells following treatment with peptides having the amino acid sequences set out in SEQ ID NO: 1 and SEQ ID NO:4.

FIG. 17 shows the structure of a cyclic heptamer of SEQ ID NO:17.

FIG. 18 shows fibroblast cells that have been treated with a control (no peptide) after 10 days exposure and fibroblast cells that have been treated with a peptide having the amino acid sequence set out in SEQ ID NO: 17 after 10 days exposure.

FIG. 19 shows fibroblast cells that have been treated with a control (no peptide) after 20 days exposure and fibroblast cells that have been treated with a peptide having the amino acids sequence set out in SEQ ID NO 17 after 20 days exposure.

DETAILED DESCRIPTION OF THE INVENTION

Peptides can be synthesized according to standard methods. Alternatively, they may be produced by recombinant DNA technology and gene expression technology.

When the peptide comprises the Penetratin™ sequence, the peptide may be produced by cloning DNA encoding the peptide into a Transvector™ vector (Qbiogene Inc., Carlsbad, Calif., USA), transforming an *E. coli* strain having the T7 polymerase gene with the vector and expressing the peptide by induction with IPTG (Isopropyl-β-D-thiogalactoside; Roche Molecular Biochemicals, Indianopolis, Ill., USA). Transvector™ vectors may be used to produce fusion proteins comprising the Penetratin™ sequence.

Peptide mimetics of the peptides of the present invention may be designed and synthesized according to standard methods. Methods of modifying peptides to produce peptide mimetics are discussed in Kieber-Emmons et al. (Curr. Opin. Biotechnol. (1997) δ: 435-441) and Beeley (Trends Biotechnol. (1994) 12: 213-216).

Peptide mimetics include analogues of the peptides of the invention where the various amide bonds (CONH) have been replaced with alternative bonding patterns such as C—C (carbon to carbon single bonds), C=C (carbon to carbon double bonds), C≡C (carbon to carbon triple bonds), $SO_2NH$ (sulphonamides), NH.CO.NH (ureas), CO.O (esters), C(R'R")O or OC(R'R") (ethers), CH(R)CONH or CONHCH(R) (β-amino acids), NHCO (reverse peptides), wherein R is any stable substituent.

Peptide mimetics also include "peptoids" in which one or more amino acids are replaced by the 'peptoid' fragment $N(R^*)CH_2CO$, wherein R* is the side chain of the amino acid. In addition, peptide mimetics include peptides where the ends of the peptide sequence are linked through a spacer molecule to give a less flexible structure.

Peptide mimetics may also be molecules consisting of a rigid scaffold composed, for example, of aromatics, polyaromatics, heteroaromatics, cycloalkyl rings or cyclic amides, and substituents mimicking the side chain functionality found in the native peptide (ie guanidine, amide, alkyl) such that the relative arrangement of the side chain functionality in the bioactive conformation of the peptide is effectively mimicked by the relative arrangement of the side chain functionality in the small drug molecule.

The observations and theory that led to the inventor arriving at the present invention will now be briefly explained. The theory is not intended to be limiting.

Figure 1:
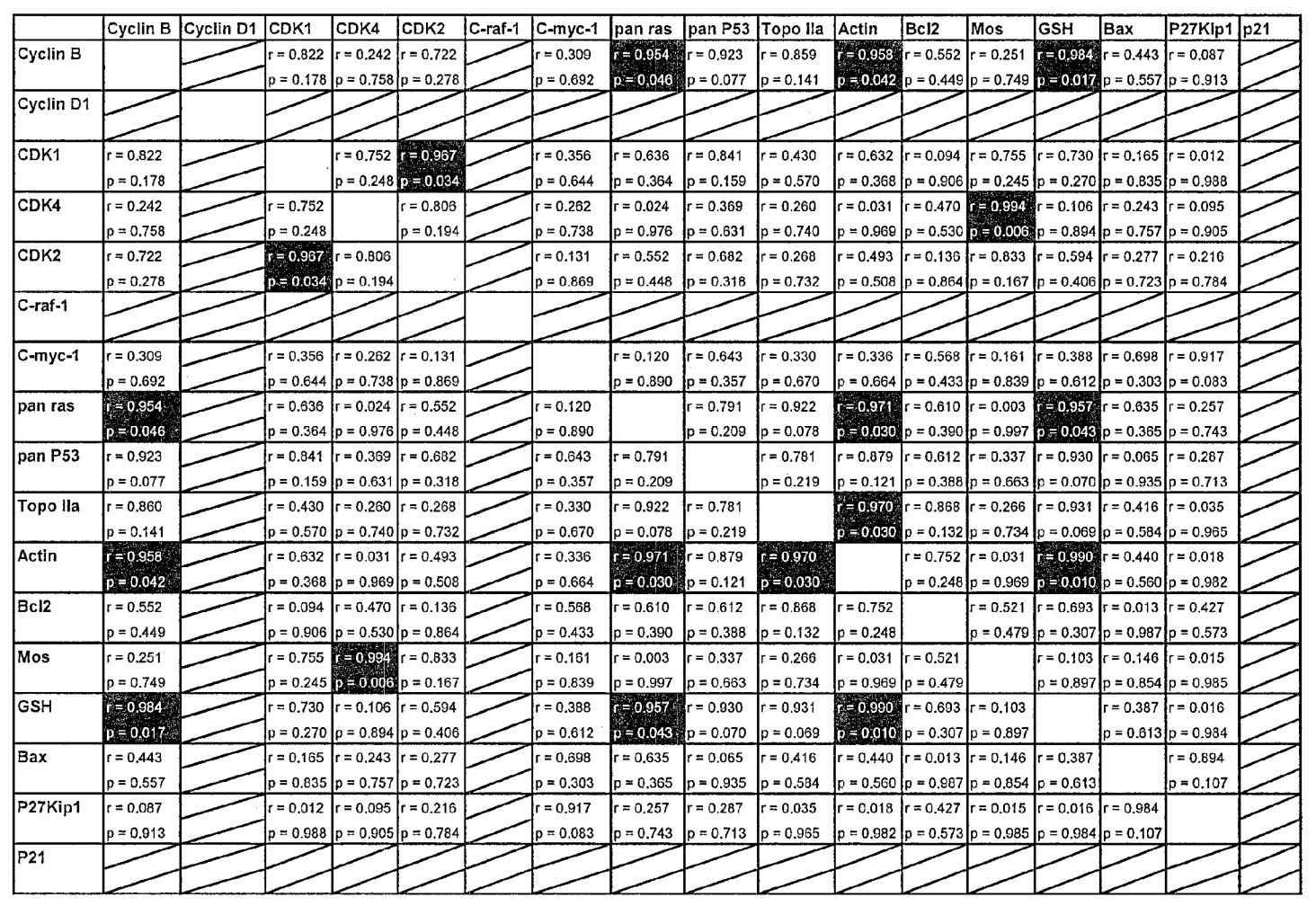
Figure 3:
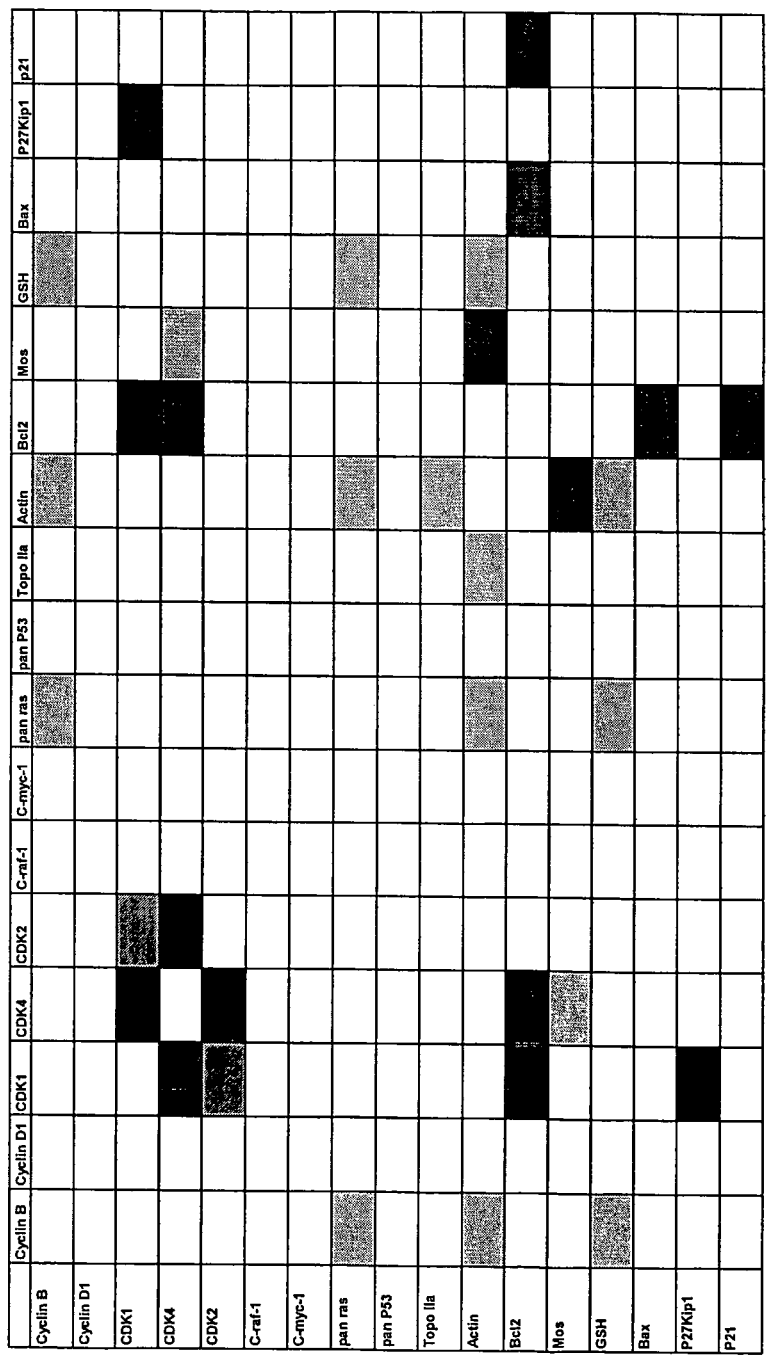
FIG. 3 is an overlay of FIGS. 1 and 2, showing that the pattern of gene expression in human cancer cells differs from the pattern of gene expression in normal human keratinocytes.

Each normal (non-cancerous) cell type has a complex pattern of interactive gene expression that permits appropriate cell survival and proliferation. Cancer cells have a different pattern of gene expression to normal (non-cancerous) cells. The inventor believes that each cancer cell comprises a unique emergent system derived from damage to the complex interactive system of normal (non-cancerous) cells. Cancer cell emergent systems are inherently unstable. Thus, in order to survive, cancer cells require readjustment of critical normal gene products to maintain stability. This stabilization is termed neostasis. This can be seen from FIGS. 1 and 2. FIG. 1 shows the correlation in expression levels of 17 proteins whose normal role is the control of cell division, differentiation, senescence and programmed cell death in normal human keratinocytes. Those pairs of proteins whose expression levels have a correlation coefficient of greater than 0.5 are highlighted. FIG. 2 shows the correlation of the expression levels of the same proteins in 20 human cancer cell lines. Again, those pairs of proteins whose expression levels have a correlation coefficient of greater than 0.5 are highlighted. FIG. 3 is overlay of FIGS. 1 and 2. It shows that the expression levels of different pairs of proteins are correlated in normal human keratinocytes and human cancer cells, confirming that normal human keratinocytes have a different pattern of gene expression to human cancer cells.

FIG. 4 shows the correlation of expression levels of the same proteins in 20 human cancer cell lines containing wild type p53 protein, and FIG. 5 shows the correlation of the expression levels of these proteins in 20 human cancer cell lines containing mutant p53 protein. Again, by comparison of those pairs of proteins whose levels are correlated in p53 mutant and wild type cancers, it can be seen that the patterns of gene expression are different. Thus, the patterns of gene expression are different dependent upon whether cells are normal, wild type p53 cancer cells, or mutant p53 cancer cells.

Figure 6:
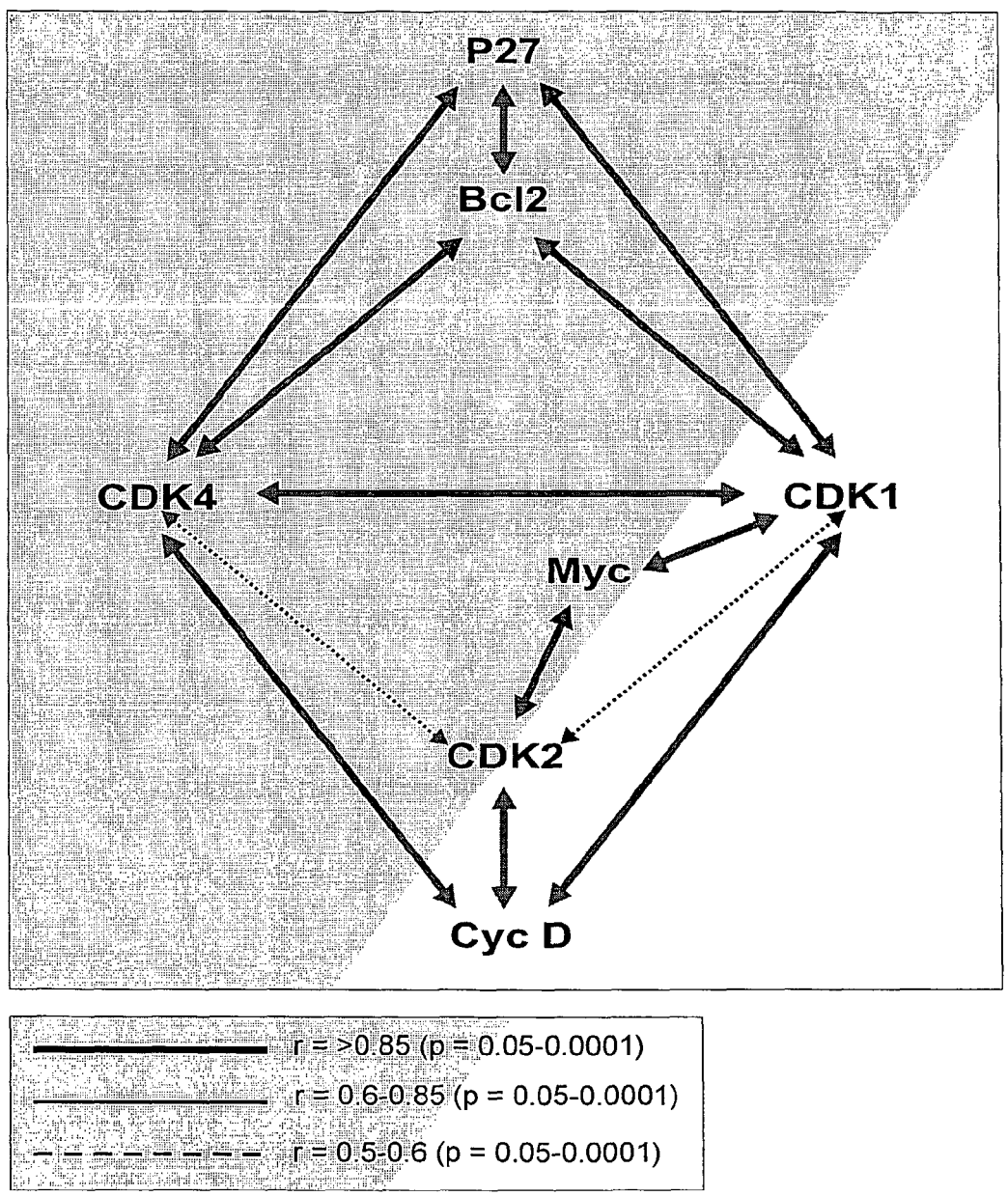
FIG. 6 is a schematic diagram representing the pattern of gene expression in p53 mutant human cancer cells.

The correlations observed between protein levels in cells can be represented graphically. FIG. 6 represents the pattern of gene expression in p53 mutant cancer cells. It shows that the level of CDK4 protein is correlated with the level of the CDK1, p27, Bcl2, CDK2 and cyclin D proteins.

Figure 7:
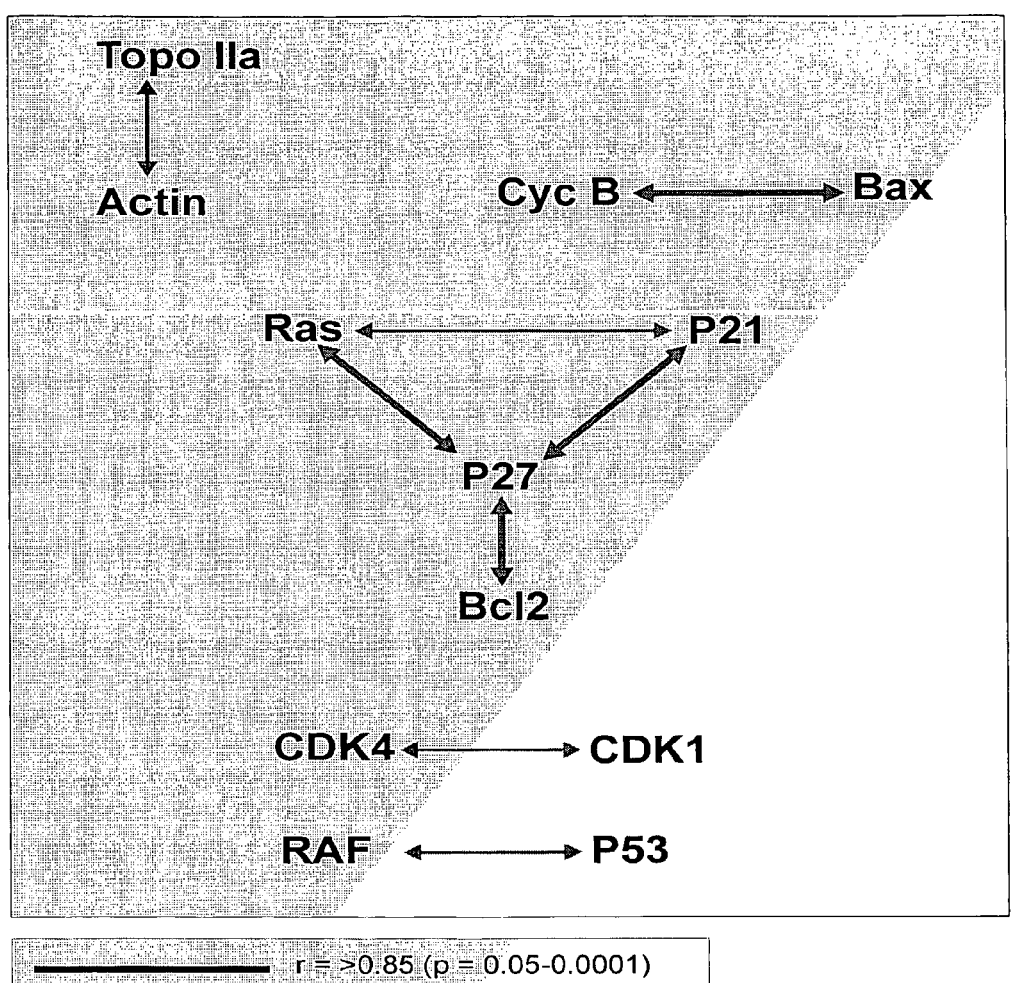
FIG. 7 is a schematic diagram representing the pattern of gene expression in p53 wild type human cancer cells.

FIG. 7 shows the pattern of gene expression in p53 wild type cancer cells. This shows that the level of CDK4 protein is correlated with the level of CDK1 protein. In addition, the level of the p27 protein is correlated with the levels of the Ras, p21 and Bcl2 proteins.

As discussed above, different cancers exhibit different patterns of gene expression. The inventor believes that each cancer has a unique pattern of gene expression that permits cell survival and proliferation.

The inventor also considers that the CDK4 protein plays a pivotal role in cancer cells by maintaining a pattern of gene expression that permits cell survival and proliferation. Accordingly, without being bound by theory, the inventor believes that the CDK4 peptides and peptide mimetics of the present invention interfere with this process, leading to a pattern of gene expression that does not permit cell survival and proliferation, and ultimately leading to cancer cell death.

Experiment 1 identifies a region on the human CDK4 protein that is absent in CDK2, CDK1 and CDK6. The region is distinct from the kinase region and the Rb and p16 binding sites in the N-terminal two thirds of CDK4. It is also partially hydrophobic despite being on the outside of CDK4. These properties suggest that it may form a protein binding site. A protein binding to this region may be directly or indirectly responsible for regulating the levels of other gene products. Accordingly, it is thought that the peptides and peptide mimetics of the invention act by binding this factor. This may lead to the factor being activated or inactivated, resulting in inappropriate regulation of the other gene products. Alternatively, this may prevent the factor from binding to CDK4, again leading to inappropriate regulation of the other gene products. In either event, the pattern of gene expression is disrupted, resulting in cancer cell death.

The region of the CDK4 protein identified in Experiment 1 also has homology with a region of the p27 protein. The peptides of the present invention may therefore act upon the p27 protein. FIG. 7 shows that this is an important protein in p53 wild type human cancer cells. This may help to disrupt the pattern of gene expression in p53 wild type human cancer cells.

FIGS. 4 and 5 show that the correlation between the levels of CDK1 and CDK4 is strongest in p53 mutant cells. This suggests that the role of CDK4 in regulating other gene products may be more important in p53 mutant cells. Accordingly, in p53 mutant cancer cells, the peptides of the present invention are advantageously administered together with a p53 inhibitor such as pifithrin-α.

The experiments which led the inventor to identify the anti-cancer activity of the peptides and peptide mimetics of the present invention are described below. Details of the experimental protocols used are not intended to be limiting.

EXPERIMENT 1

It is known that CDK4 protein plays an important role in cancer. However, drugs that inhibit the kinase activity of human CDK4 are ineffective at treating cancer. The inventor hypothesizes that this is because the CDK4 protein plays a role in cancer cells that is independent of its kinase activity. To verify this hypothesis, the inventor attempted to identify the region of CDK4 protein that mediates a role in cancer cells by looking for differences between the amino acid sequence of the CDK4 protein, and the amino acid sequences of the CDK6 and CDK2 proteins, which are highly homologous to the CDK4 protein but which do not mediate an important role in cancer cells.

Figure 8:
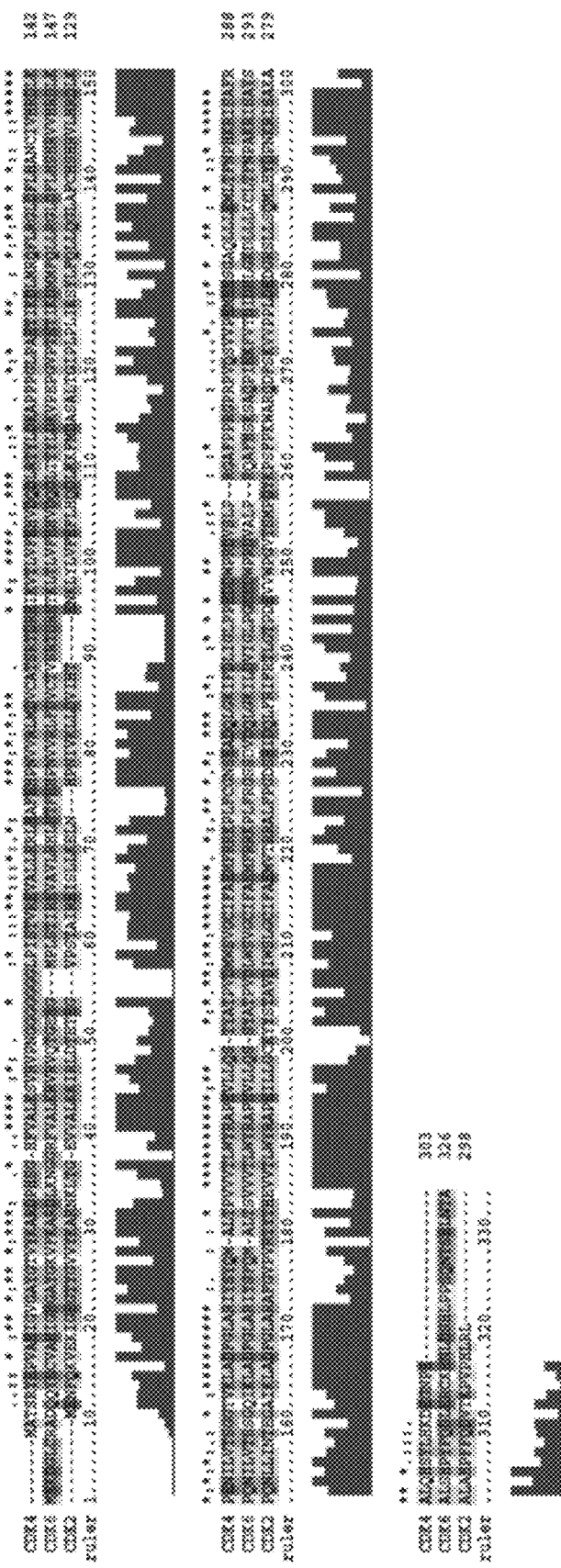
FIG. 8 shows a global multiple sequence alignment of the amino acid sequences of human CDK2 (SEQ ID NO:54), CDK4 (SEQ ID NO:55) and CDK6 (SEQ ID NO:56).

The sequences of human CDK4, CDK6 and CDK2 were obtained from the Swiss-Prot and TrEMBL databases, maintained by the Expasy molecular biology server (ca.expasy.org/). These sequences were aligned using the ClustalX 1.83 algorithm using the PAM 250 matrix, a gap opening penalty of 10, and a gap extending penalty of 0.2. FIG. 8 shows the results of the alignment. The N-terminal half of the human CDK4 sequence shows considerable homology to the human CDK6 and CDK2 sequences. Because of this, it was considered unlikely that this region mediates the function of the human CDK4 protein in cancer cells.

The C-terminal two thirds of the CDK4 protein is not homologous to the human CDK2 and CDK6 proteins. This region could therefore potentially mediate a role in cancer cells. To identify whether elements of this region are important, the inventor searched for sequences in the C-terminal two thirds of the CDK4 protein that are conserved between species.

The amino acid sequences of CDK4 proteins from various species were obtained from the Swiss-Prot and TrEMBL databases, maintained by the Expasy molecular biology server (ca.expasy.org/). These are listed in table 1. Table 1 also provides the database accession number of each sequence, and the percentage homology of each sequence with the human CDK4 amino acid sequence.

TABLE 1

List of CDK4 sequences. Sequence identity and similarity is measured to the *Homo sapiens* sequence.

| Swiss-Prot/ Trembl Identifier | Organism | % Sequence Identity | % Sequence Similarity |
|---|---|---|---|
| P11802 | *Homo Sapiens* | 100 | 100 |
| P79432 | *Sus Scrofa* (Pig) | 98 | 98 |
| P35426 | *Rattus norvegicus* (Rat) | 95 | 97 |
| P30285 | *Mus musculus* (Mouse) | 94 | 97 |
| Q9CYR7 | *Mus musculus* (Mouse) | 90 | 93 |
| Q91727 | *Xenopus laevis* (African clawed frog) | 77 | 85 |
| Q8WQU5 | *Lytechinus variegatus* (Sea urchin) | 59 | 74 |
| Q8WQU6 | *Strongylocentrotus purpuratus* (Purple sea urchin) | 59 | 74 |
| Q94877 | *Drosophila melanogaster* (Fruit fly) | 47 | 66 |

Figure 9:
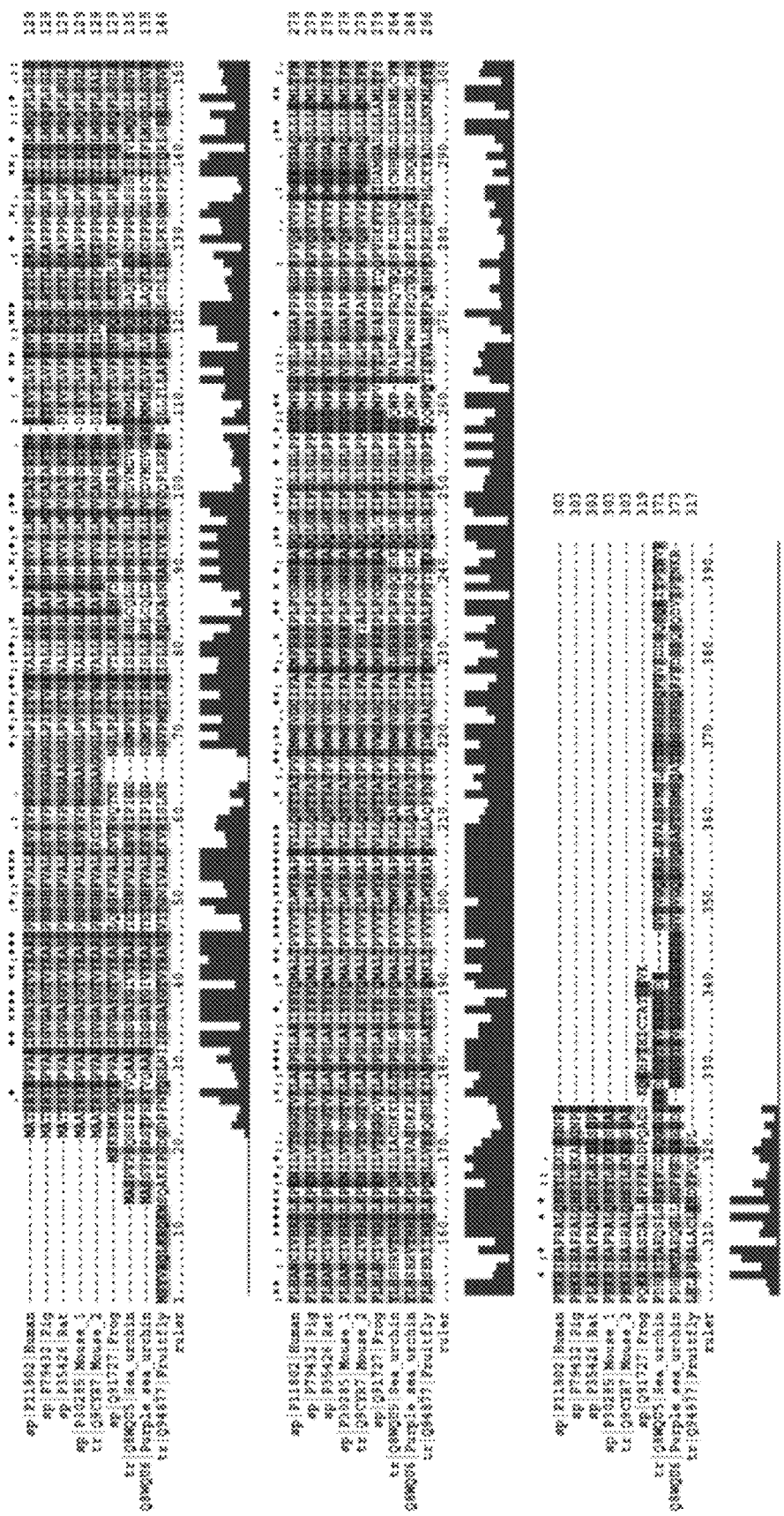
FIG. 9 shows a global multiple sequence alignment of the amino acid sequences of CDK4 proteins from various species (SEQ ID NO:55 and 57-64).

A global multiple sequence alignment was performed, using the program ClustalX (Jeanmougin et al. (1998) Trends Biochem. Sci. 23: 403-5). This is shown in FIG. 9. This shows that the N-terminal region of the protein is highly conserved. In addition, the C-terminal region of mammalian CDK4 sequences is also conserved. For example, FPPRGPRPVQ (SEQ ID NO:1), present in human CDK4 is highly conserved in other mammalian CDK4 proteins.

A three dimensional model of human CDK4 was prepared to determine the location of SEQ ID NO:1.

Potential templates for the model of CDK4 were obtained by performing a Blast search with default parameters on the protein database (PDB) for structures with similar sequences to human CDK4. The search retrieved several structures for human CDK6 and human CDK2, which proteins have 71% and 45% sequence identity with the human CDK4 protein respectively. Although CDK2 possesses a lower sequence identity with CDK4, the sequence similarity between CDK2 and CDK4 is 64% indicating that the structure of CDK2 may be a good model for the structure of human CDK4. The retrieved structures, together with their PDB identifier and crystallographic resolution, are listed in table 2.

TABLE 2

List of chosen template structures. CDK6 has 71% seq. id. and 81% seq. sim., CDK2 has 45% seq. id. and 64% seq. sim. Rmsd is measured from the C$_\alpha$s

| PDB Identifier | Resolution (in Å) | Additional molecules/comments | Rmsd. From 1BLX (in Å) |
|---|---|---|---|
| CDK6 Structures | | | |
| 1BLX | 1.9 | P19-INK4d | 0.00 |
| 1G3N | 2.9 | P18-INK4c, K-Cyclin | 0.82 |
| 1BI8 | 2.8 | P19-INK4d | 0.86 |
| 1BI7 | 3.4 | P16-INK4a | 1.11 |
| 1JOW | 3.1 | V-Cyclin | 1.01 |
| CDK2 Structures | | | |
| 1HCL | 1.8 | — | 1.17 |
| 1GII | 2.0 | ATP-binding region mutated to that of CDK4; small molecule inhibitor bound | 1.15 |

The structures were checked for errors and problems that might affect the structure building process. The structures were all processed by the WHAT-CHECK program (Hooft et al. (1996) Nature 381: 272). The overall quality is shown in table 3.

TABLE 3

Evaluation of the stereochemistry, amino acid distribution, and packing in the template structures using WHAT-CHECK. The modeller's quality scores indicate how reliable the structure is for modelling purposes. The crystallographer's quality scores indicate how the structure compares to other structures of a similar resolution. Structure Z-scores below −2.0 are poor, and below −4.0 are bad.

|  | MODEL | | | |
| --- | --- | --- | --- | --- |
|  | 1BLX | 1G3N | 1BI8 | 1BI7 |
| Resolution | 1.9 | 2.9 | 2.8 | 3.4 |
| MODELLER'S QUALITY | | | | |
| Structure Z-scores, positive is better than average | | | | |
| $2^{nd}$ generation packing quality[a] | −0.704 | −0.108 | −0.216 | 0.044 |
| Ramachandran plot appearance | −5.658 (bad) | −4.729 (bad) | −1.589 | −3.195 (poor) |
| $\chi$-1/$\chi$-2 rotamer quality | −4.32 (bad) | −3.896 (poor) | −1.489 | −2.09 |
| Backbone conformation | −7.733 (bad) | −5.705 | −4.496 (bad) | −4.093 (bad) |
| RMS Z-scores, should be close to 1 | | | | |
| Bond lengths | 0.559 (tight) | 0.717 | 0.829 | 0.553 (tight) |
| Bond angles | 0.909 | 0.984 | 1.627 (loose) | 0.845 |
| Omega angle restraints | 0.266 (tight) | 0.316 (tight) | 1.251 | 0.281 (tight) |
| Side chain planarity | 0.559 (tight) | 0.607 (tight) | 1.003 | 0.423 (tight) |
| Improper dihedral distribution | 0.884 | 1.011 | 1.524 (loose) | 0.505 |
| Inside/Outside distribution | 1.027 | 1.021 | 1.054 | 1.039 |
| CRYSTALLOGRAPHER'S QUALITY | | | | |
| Structure Z-scores, positive is better than average | | | | |
| $2^{nd}$ generation packing quality[a] | 1.2 | 1.5 | −0.4 | 1.5 |
| Ramachandran plot appearance | −2.5 | −2.2 | −1.4 | −0.8 |
| $\chi$-1/$\chi$-2 rotamer quality | −1.8 | −1.6 | −0.8 | −0.2 |
| Backbone conformation | −5.8 (bad) | −5.4 (bad) | −5.3 (bad) | −3.0 (poor) |
| RMS Z-scores, should be close to 1 | | | | |
| Bond lengths | 0.559 (tight) | 0.717 | 0.829 | 0.553 |
| Bond angles | 0.909 | 0.984 | 1.627 | 0.845 |
| Omega angle restraints | 0.266 (tight) | 0.316 (tight) | 1.251 | 0.281 (tight) |
| Side chain planarity | 0.559 (tight) | 0.607 (tight) | 1.003 | 0.423 (tight) |
| Improper dihedral distribution | 0.884 | 1.011 | 1.524 (loose) | 0.505 |
| Inside/Outside distribution | 1.027 | 1.021 | 1.054 | 1.039 |

[a] $2^{nd}$ generation packing score indicates how comfortable the sequence is in the structure. A positive score is good. A score below −2.0 is poor indicating a problem in the structure, and scores below −4.0 are bad indicating serious errors in the structure.

|  | MODEL | | |
| --- | --- | --- | --- |
|  | 1JOW | 1HCL | 1GII |
| Resolution | 3.1 | 1.8 | 2.0 |
| MODELLERS QUALITY | | | |
| Structure Z-scores, positive is better than average | | | |
| $2^{nd}$ generartion packing quality[a] | −2.046 | −1.170 | −1.363 |
| Ramachandran plot appearance | −5.911 (bad) | −0.681 | −0.816 |
| $\chi$-1/$\chi$-2 rotamer quality | −3.372 (poor) | −2.019 | −1.935 |
| Backbone conformation | −6.752 (bad) | −2.630 | −4.937 (bad) |
| RMS Z-scores, should be close to 1 | | | |
| Bond lengths | 0.396 (tight) | 0.511 (tight) | 0.680 |
| Bond angles | 0.68 | 0.778 | 0.901 |
| Omega angle restraints | 0.217 (tight) | 0.301 (tight) | 0.386 (tight) |
| Side chain planarity | 0.228 (tight) | 0.588 (tight) | 0.940 |
| Improper dihedral distribution | 0.429 | 0.753 | 1.105 |
| Inside/Outside distribution | 1.055 | 1.007 | 1.010 |
| CRYSTALLOGRAPHERS QUALITY | | | |
| Structure Z-scores, positive is better than average | | | |
| $2^{nd}$ generartion packing quality[a] | 0 | −1.1 | −0.9 |
| Ramachandran plot appearance | −3.1 | −0.6 | −0.2 |
| $\chi$-1/$\chi$-2 rotamer quality | −1.0 | −1.6 | −1.0 |
| Backbone conformation | −4.8 (bad) | −3.0 | −5.0 (bad) |
| RMS Z-scores, should be close to 1 | | | |
| Bond lengths | 0.396 | 0.511 (tight) | 0.680 |
| Bond angles | 0.68 | 0.778 | 0.901 |

TABLE 3-continued

| | | | |
|---|---|---|---|
| Omega angle restraints | 0.217 (tight) | 0.301 (tight) | 0.386 (tight) |
| Side chain planarity | 0.228 (tight) | 0.588 (tight) | 0.940 |
| Improper dihedral distribution | 0.429 | 0.753 | 1.105 |
| Inside/Outside distribution | 1.055 | 1.007 | 1.010 |

[a]$2^{nd}$ generation packing score indicates how comfortable the sequence is in the structure. A positive score is good. A score below −2.0 are poor indicating a problem in the structure, scores below −4.0 are bad indicating serious errors in the structures.

The quality scores of the initial structures are poor. This probably reflects the fact that most of the structures were deduced in the presence of bound proteins which gives rise to distortion of the structure. In view of these quality scores and the low resolution of the initial structures, models based on these structures may be expected to provide reliable information only on tertiary structure, the position of the amino-acid residues within the structure, and whether those residues are buried or solvent accessible. More detailed information such as the direction of internal hydrogen bonds, interactions of side chains, or the measurement of the solvent accessibility of the residues may not, however, be accurate.

Five models of the structure of human CDK4 were constructed using the program JACKAL 1.5 (Xiang, J. Z. University of Columbia (2002), described in Xiang et al. (2001) J. Mol. Biol. 311: 421-430 and Xiang et al. (2002) Proc. Natl. Acad. Sci., USA 99: 7432-7437). The known structures used as the starting point for these models are given in table 4.

TABLE 4

Templates used in the building of each model.

| Model No. | Templates |
|---|---|
| 1 | 1BLX (CDK6) |
| 2 | 1G3N (CDK6) |
| 3 | Base template = 1BLX, Variable regions differing by more than 2.0 Å rmsd modelled from 1G3N, 1BI8, 1BI7 and 1JOW (all CDK6) |
| 4 | Base template = 1BLX, Variable regions differing by more than 2.0 Å rmsd. modelled from 1HCL (CDK2) |
| 5 | Base template = 1BLX, Variable regions differing by more than 2.0 Å rmsd. modelled from 1GII (CDK2) |

The modeling process is outlined below:

1. Residues that were not conserved between the initial structure and human CDK4 were replaced in the model with the corresponding residue present in human CDK4. This step was carried out using Profix, a utility program distributed with JACKAL.

Essentially, Profix changes those residues in the starting structure that differ from those present in human CDK4, whilst retaining the original backbone conformation. The structure was then subjected to energy minimization to remove atom clashes. This is performed using the fast torsion angle minimiser function of JACKAL. This function employs the CHARMM22 all atom force field (MacKerell et al. (1998) J. Phys. Chem. B. 102: 3586-3616). Insertions and deletions were then made to complete the change in the starting sequence to that of human CDK4. The bonds were then closed using a random tweak method and the structure was again subjected to energy minimization to remove atom clashes, as described above.

2. The secondary structure was assigned using a DSSP-like routine as described in Kabsch and Sander (Biopolymers 22: 2577-2637 (1983)).

3. The loop regions were then predicted as follows. The original backbone segment was deleted and replaced by a new segment made by generating a large number of random backbone conformations, which were then closed using a random tweak method. The new backbones were then subjected to energy minimization to remove atom clashes as described above. The side chains were modeled using a large rotamer library of 3222 rotamers in 10° bins according to methods known in the art and the structure was again subjected to energy minimization. The structure having the lowest energy is retained and a further round of conformation sampling is performed using the new conformation. The resulting structure is subjected once again to energy minimization.

4. The secondary structure elements were refined again by sampling through a backbone rotamer library, but with the original rotamer retained in the sampling. In order to retain the hydrogen bonding network of the existing secondary structure, a large energy penalty is incurred in any conformation that breaks an existing hydrogen bond. The lowest energy conformation is retained. The side chains are then built in a similar way.

5. The final structure is then subjected to energy minimization using the torsion angle minimiser.

6. After construction of the model, the model is subjected to 500 steps of steepest descent full energy minimization using AMBER, with the parm96 force field (Case et al. (1995) J. Am. Chem. Soc. 117: 5179-5197). The polar hydrogens were added by WHATIF after optimizing the hydrogen bond network (Vriend (1990) J. Mol. Graph. 8:52-56; Hooft et al. (1996) Proteins 26: 363-376).

7. Steps 1-6 were repeated until no further improvement in the model was obtained.

At points it was also necessary to manually tweak the structures. This was performed through the Swiss-PDB viewer.

The quality of the produced models was assessed by the program WHAT-CHECK. Additionally, the threading score and molecular mechanics energy were calculated by Swiss PDB-viewer to assess how well the sequence fits the structure. The threading energy is based on the potential of mean force developed by Sippl et al. (J. Mol. Biol. (1990) 213: 859-883) and the molecular mechanics energy is calculated using the GROMOS96 force field (van Gunsteren et al. (1996) The GROMOS96 manual and user guide, Vdf Hochschulverlag ETHZ). The results are shown in table 5. This shows that the most reliable is model 1, although the best backbone conformation is given in model 2.

TABLE 5

Quality and accuracy scores for the built models. A high threading score indicates a better fit of the sequence in the structure. A low molecular mechanics energy indicates a more relaxed structure. Structural Z-scores less than −2.0 indicate problems in the model, scores less then −4.0 indicates serious errors. RMS Z-scores should be close to 1.0. ± 0.5 either side indicates either wide or tight distributions respectively.

|  | MODEL | | | | |
|---|---|---|---|---|---|
|  | Model 1 | Model 2 | Model 3 | Model4 | Model 5 |
| Threading score | 165.6 | 158.2 | 151.0 | 128.8 | 99.7 |
| Molecular mechanics energy (kJ mol$^{-1}$) | −12203.3 | −12526.1 | −12182.5 | −11900.3 | −11795.5 |
| RMS deviation from 1BLX (in Å) | 0.48 | 0.88 | 0.62 | 0.67 | 0.65 |
| Structure Z-scores, positive is better than average | | | | | |
| $2^{nd}$ generation packing quality | −1.093 | −0.868 | −0.964 | −1.090 | −1.228 |
| Ramachandran plot appearance | −2.573 | −3.374 | −2.837 | −2.965 | −3.104 |
| χ-1/χ-2 rotamer quality | −1.148 | −1.470 | −1.340 | −0.955 | −0.968 |
| Backbone conformation | −6.485 | −5.201 | −5.637 | −7.016 | −7.564 |
| RMS Z-scores, should be close to 1 | | | | | |
| Bond lengths | 0.655 | 0.645 | 0.652 | 0.657 | 0.668 |
| Bond angles | 1.187 | 1.176 | 1.183 | 1.168 | 1.181 |
| Omega angle restraints | 1.354 | 1.159 | 1.413 | 1.478 | 1.396 |
| Side chain planarity | 1.608 | 1.667 | 1.494 | 1.277 | 1.292 |
| Improper dihedral distribution | 0.883 | 0.882 | 0.907 | 0.879 | 0.865 |
| Inside/Outside distribution | 1.019 | 1.038 | 1.025 | 1.043 | 1.051 |

Figure 10:
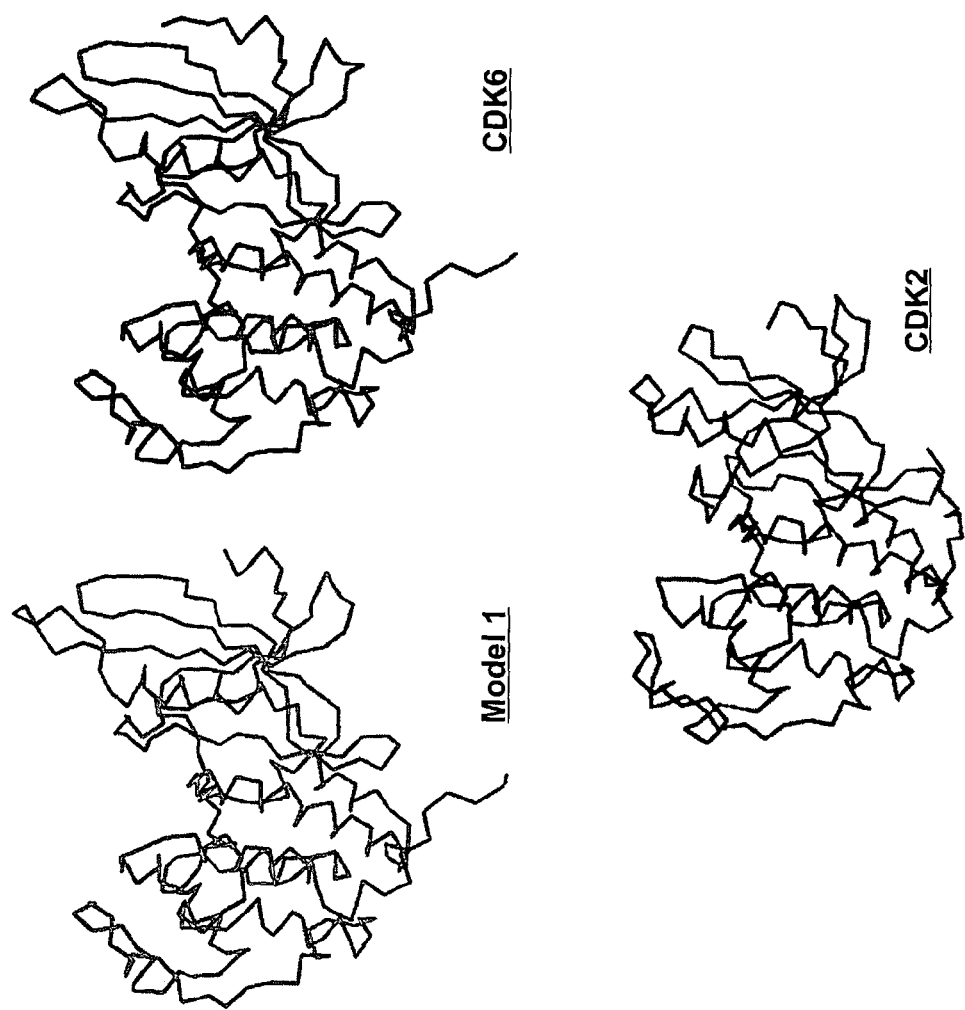
FIG. 10 shows the Cα trace (backbone) of human CDK6 and human CDK2. The modeled Cα trace of human CDK4 (model 1) is also shown.

FIG. 10 shows the Cα traces for model 1, CDK6 and CDK2. This shows that the structure of model 1 closely resembles the CDK6 structure, although CDK6 has longer C- and N-termini.

FIG. 10 also shows that the structure of human CDK4 is split into two domains. The first domain (domain 1) contains a mixture of α-helix and β-strand structural elements. By analogy with CDK6 and CDK2, this domain mediates kinase activity. The second domain (domain 2) is primarily α-helical in nature.

Figure 11:
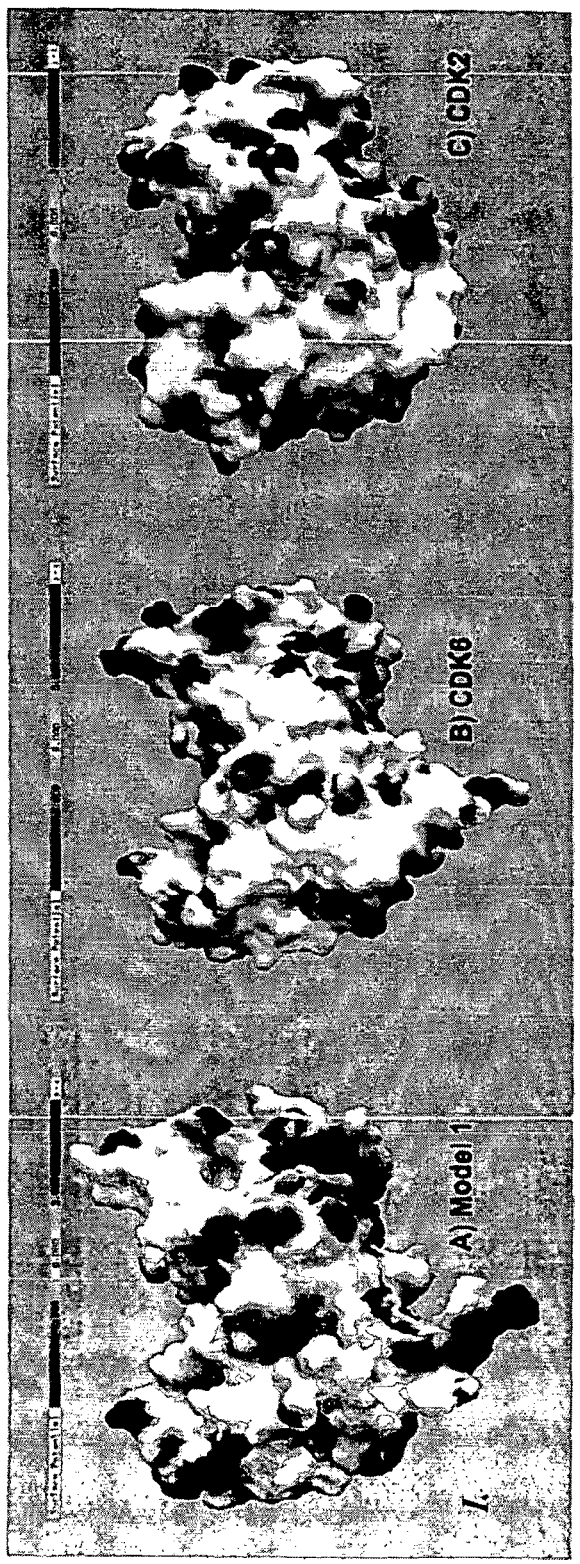
FIG. 11 shows electrostatic potential plots of human CDK4 (model 1), human CDK6 and human CDK2. I shows the view from the front. Domain I is to the right of the structures, domain II is to the left. II shows the view from the back. Domain I is to the left of the structures, domain II is to the right. III shows a view looking directly at the 12 mer fragment. The thick black arrow indicates the position of the fragment or the correspondingly aligned fragment in CDK6 and CDK2.
Figure 11:
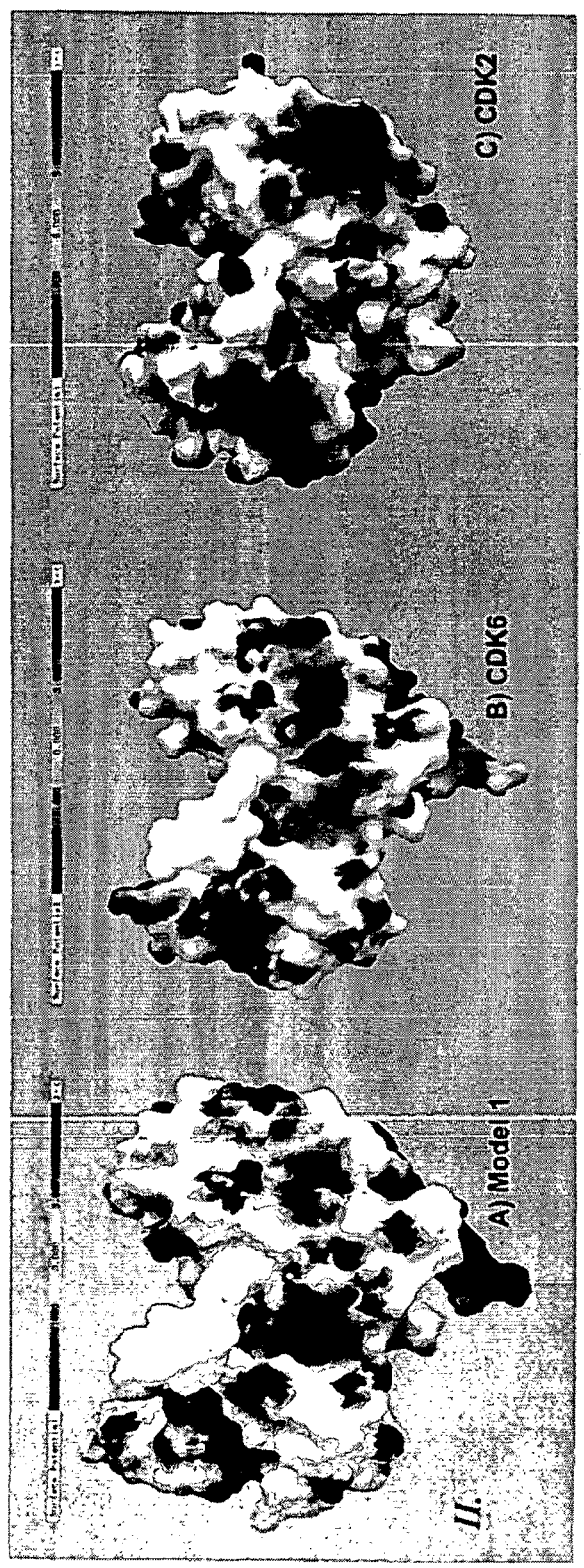
Figure 11:
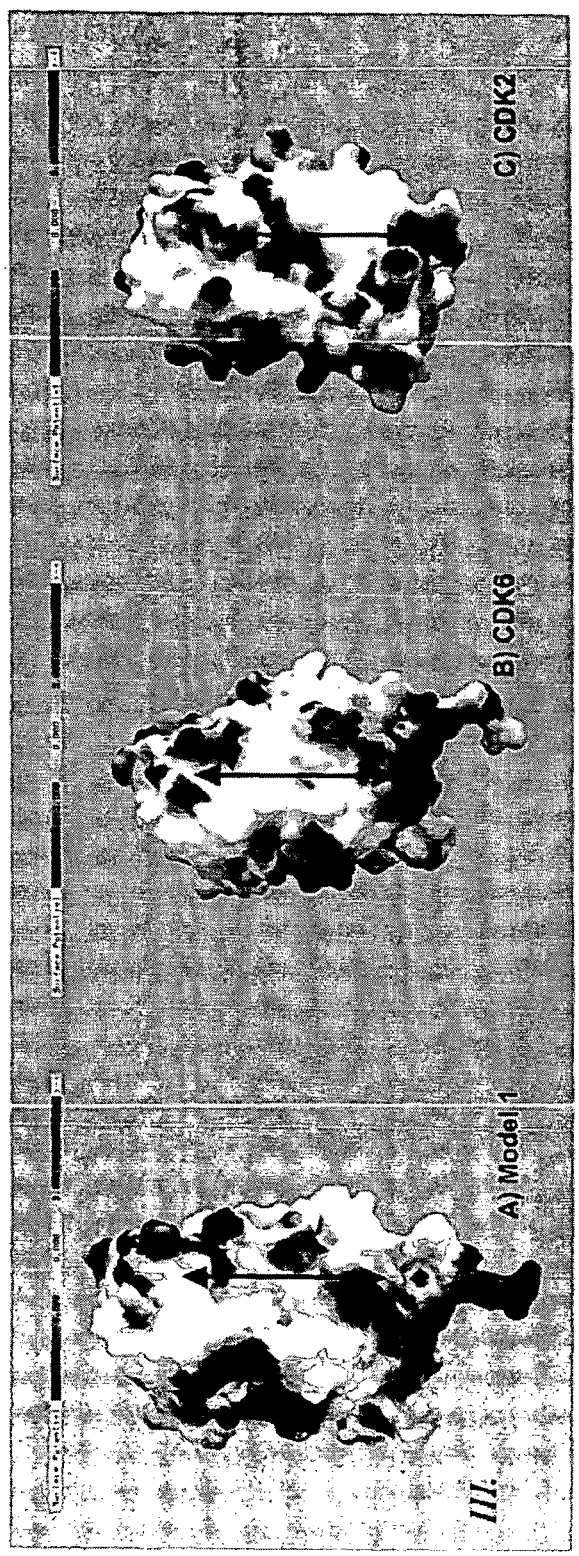

FIG. 11 shows electrostatic potential plots of model 1, CDK6 and CDK2. This shows that domain 1 of model 1 is less charged than either CDK6 or CDK2. In addition, domain 2 of model 1 contains a solvent accessible sequence from 248-259 that is not present in CDK6 or CDK2. This contains SEQ ID NO:1, the sequence identified in the alignment as being conserved in mammalian CDK4 proteins. This has a substantial hydrophobic component and also has a preponderance of small residues resulting in a flatter surface. A flatter surface results in a better contact for a protein partner. In view of these characteristics, the inventor hypothesizes that this sequence may form a protein binding site.

A search of the ProDom database showed that this sequence did not correspond to any recognized domain. However, a multiple alignment tool TCoffee did reveal that this sequence is homologous to a region of the p27 protein (FYYRPPRPPKGA) (SEQ ID NO:53).

EXPERIMENT 2

As discussed in Experiment 1, the inventor hypothesized that a region of the CDK4 protein that does not mediate the kinase activity of CDK4 could be responsible for maintaining neostasis in cancer cells. The model of human CDK4 produced in Experiment 1 reveals that the amino acid sequence 248-259 may form a binding site for an unknown protein. To determine whether this binding site is required for the maintenance of cancer cell survival and proliferation, experiments were conducted to determine the effect of interfering with protein binding to this site.

A peptide encoding amino acids 249-258 was synthesized (in the form of a chloride salt) by standard methods. The sequence of this peptide is given below as SEQ ID NO:1.

SEQ ID NO: 1:           FPPRGPRPVQ

A peptide having 80% sequence identity to the sequence of SEQ ID NO:1 was also synthesized as a chloride salt. The sequence of this peptide is given below as SEQ ID NO:2.

SEQ ID NO: 2:           FTPRGTRPVQ

These peptides mimic the putative binding site on the human CDK4 protein and could inhibit the binding of human CDK4 to its protein partner. If the binding site on the human CDK4 protein is involved in the maintenance of a gene expression pattern that allows cell survival and proliferation, it would be expected that these peptides would interfere with this process, possibly leading to cancer cell death.

Two control peptides were synthesized as chloride salts. The sequences of these peptides are given below as SEQ ID NO:3 and SEQ ID NO:4. SEQ ID NO:3 has 30% sequence identity with the sequence set out in SEQ ID NO:1. SEQ ID NO:4 contains the same amino acids as SEQ ID NO:1. However, the sequence of these amino acids differs and the peptide sequence has 0% homology with the sequence of SEQ ID NO:1. The control peptides do not resemble the putative binding site.

SEQ ID NO: 3:           ATTEGTETVQ

SEQ ID NO: 4:           PGPFRVPQPR

In a first experiment, MGHU-1 cells (a human bladder cancer cell line), were plated in 48 well tissue culture dishes in 0.2 ml complete Hams F12 tissue culture medium supplemented with 10% foetal calf serum. SKMEL-2 cells (a human malignant melanoma cell line), HX34 cells (a human malignant melanoma cell line) and H441 cells (a human lung cancer cell line) were plated under identical conditions. The cells were incubated at 37° C. in an atmosphere of 5% $CO_2$.

After 24 h, the culture medium was then removed from each well and replaced by Hams F12 complete tissue culture medium (without foetal calf serum). The culture medium added to each well was supplemented with a peptide having the sequence set out in SEQ ID NO:1, SEQ ID NO:2 or SEQ ID NO:3 at a concentration of either 0.5, 1.0 or 5.0 mM in such a way that each cell line was exposed to each peptide at each concentration.

Figure 12:
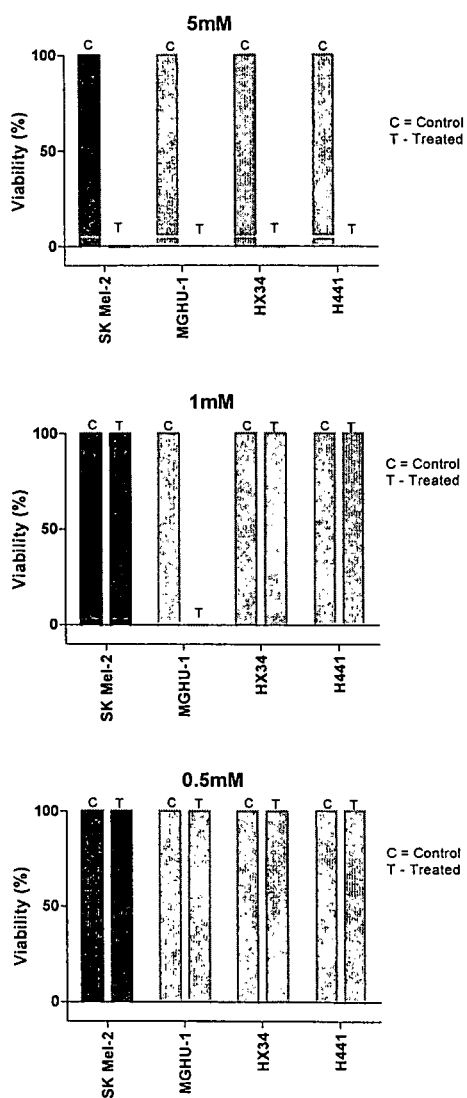
FIG. 12 shows the effect on the viability of the four human cancer cell lines of treatment with peptides having the amino acid sequences set out in SEQ ID NO:1 and SEQ ID NO:3 at concentrations of 0.5 mM, 1.0 mM and 5.0 mM.

The cells were then cultured for two days. Foetal calf serum was then added to a final concentration of 10%, and the cells were left for a further 5 days. The % viability of the cells in each well was calculated by visual observation under phase contrast microscopy. The effect of the peptides having the amino acid sequences set out in SEQ ID NO:1 and SEQ ID NO:3 on the viability of the SK MeI-2, MGHU-1, HX34 and H441 cell lines is shown in FIG. 12. FIG. 12 shows that each cell line cultured in the presence of 5.0 mM SEQ ID NO:1 was completely killed by day 7 of the experiment. Where the concentration of SEQ ID NO:1 was 1.0 mM, 100% of MGHU-1 cells were killed. The viability of the other cell lines was not affected. At a concentration of 0.5 mM SEQ ID NO:1, none of the cell lines appeared to be affected. By contrast, treatment of the cells lines with SEQ ID NO:3 at any concentration did not affect viability of any cell line.

Subsequent experiments testing cancerous and non-cancerous (fibroblasts) cell lines have shown that with the decapeptide SEQ ID NO:1 there is non specific killing between cancerous and non-cancerous cell lines within the first seven days of the experiment. Both cancerous cell lines and non cancerous cell lines (fibroblasts) then recovered and finally the specific killing of cancerous cells and not non-cancerous fibroblasts was seen between days 20 and 25.

The peptide having the amino acid sequence set out in SEQ ID NO:2 were also cytotoxic to the cancer cell lines. However, they were less cytotoxic than the peptide having the amino acid sequence set out in SEQ ID NO:1, as evidenced by visual observation of cell density and viability under phase contrast microscopy. This observation, coupled with an comparison of the sequences of SEQ ID NO:1 and SEQ ID NO:2, suggests that the prolines at positions 3 and 8 of SEQ ID NO:1 that were not substituted by threonines in SEQ ID NO:2 contribute to cytotoxicity. Cytotoxicity may also be dependent on the relationship of the prolines at positions 3 and 8 to arginine.

```
        1 2 3 4 5 6 7 8 9 10

F-P-P-R-G-P-R-P-V-Q  (SEQ ID NO: 1)
```

In a further experiment, using a different batch of synthesized peptide, RT112 cells (a human bladder cancer cell line), HT29 cells (a human colon cancer cell line) and MGHU cells (a human bladder cancer cell line) were plated as described above. In parallel, a short term primary culture of human fibroblasts was plated in 48 well plates. After 24 h, the tissue culture medium was removed from each well and replaced with Hams F12 complete tissue culture medium (without foetal calf serum) supplemented with either 2.5 mM SEQ ID NO:1 or 2.5 mM SEQ ID NO:4. After culturing for 2 days, foetal calf serum was added to a concentration of 10%. The cells were then cultured for a further 7 days and viewed under phase contrast microscopy.

FIG. 13 shows RT112 and HT29 cells following treatment with the peptide having the amino acid sequence set out in SEQ ID NO:1. Cells from each cell line that have been exposed to the SEQ ID NO:4 peptide are shown for comparison. In both cases, the differences between the control and treated cells are dramatic. The control cells are normal in appearance, whereas the treated cells are shriveled and appear to be senescent. This shows that cells treated with the peptide having the amino acid sequence set out in SEQ ID NO:1 are killed, as shown in FIG. 13a.

FIG. 14 shows MGHU-1 cells treated with peptides having the amino acid sequences set out in SEQ ID NOS: 1 and 4. The cells treated with SEQ ID NO:4 appear to be healthy, whilst all cells treated with SEQ ID NO:1 appear to be dead. FIG. 14 also shows primary human fibroblast short term cultures treated with peptides having the amino acid sequences set out in SEQ ID NOS: 1 and 4. The cells treated with both peptides appear to be healthy. These experiments show that peptides having the sequence set out in SEQ ID NO:1 or 2 are cytotoxic to cultured human cancer cells. These peptides are not cytotoxic to cultured primary cultures of normal human cells.

EXPERIMENT 3

Testing Further Analogues of SEQ ID NO: 1

Normal non-cancerous fibroblasts and cancer cells were exposed to the linear hexamer PRGPRP SEQ ID NO: 5 in 96 micro well plates using the same protocol as for SEQ. ID NO: 1 as previously described. The percent viability of the cells in each well was calculated by visual observation under phase contrast microscopy as previously described. In the case of the hexamer, at 7 days there appeared to be stimulation of fibroblast growth. No changes were observed in tumour cells until 21 days and beyond then there was almost total death of cells in the hexamer treated wells whereas the normal non-cancerous fibroblasts remained healthy.

EXPERIMENT 4

In order to define structure/function relationships different peptides were constructed SEQ ID NOS 5-16. Normal non-cancerous fibroblasts and cancer cells were exposed to 5 mM of these peptides in 96 well plates as previously described. The sequence of these peptides is listed below. Results were scored at 21 days.

```
        SEQ ID NO: 5:      PRGPRP      (Peptide A)

SEQ ID NO: 6:      PRGPR       (Peptide B)

SEQ ID NO: 7:      RGPRP       (Peptide C)

SEQ ID NO: 8:      RGPR        (Peptide D)
```

Proline to threonine substitutions were also tested in these shorter peptides viz:

```
        SEQ ID NO: 9:      TRGPRP      (Peptide E)

SEQ ID NO: 10:     TRGTRP      (Peptide F)

SEQ ID NO: 11:     TRGTRT      (Peptide G)

SEQ ID NO: 12:     PRGTRP      (Peptide H)

SEQ ID NO: 13:     PRGPRT      (Peptide I)

SEQ ID NO: 14:     PRGTRT      (Peptide J)
```

```
                    -continued
SEQ ID NO: 15:       TPPRGPRP          (Peptide K)

SEQ ID NO: 16:       PPRGPRP           (Peptide L)
```

Figure 15:
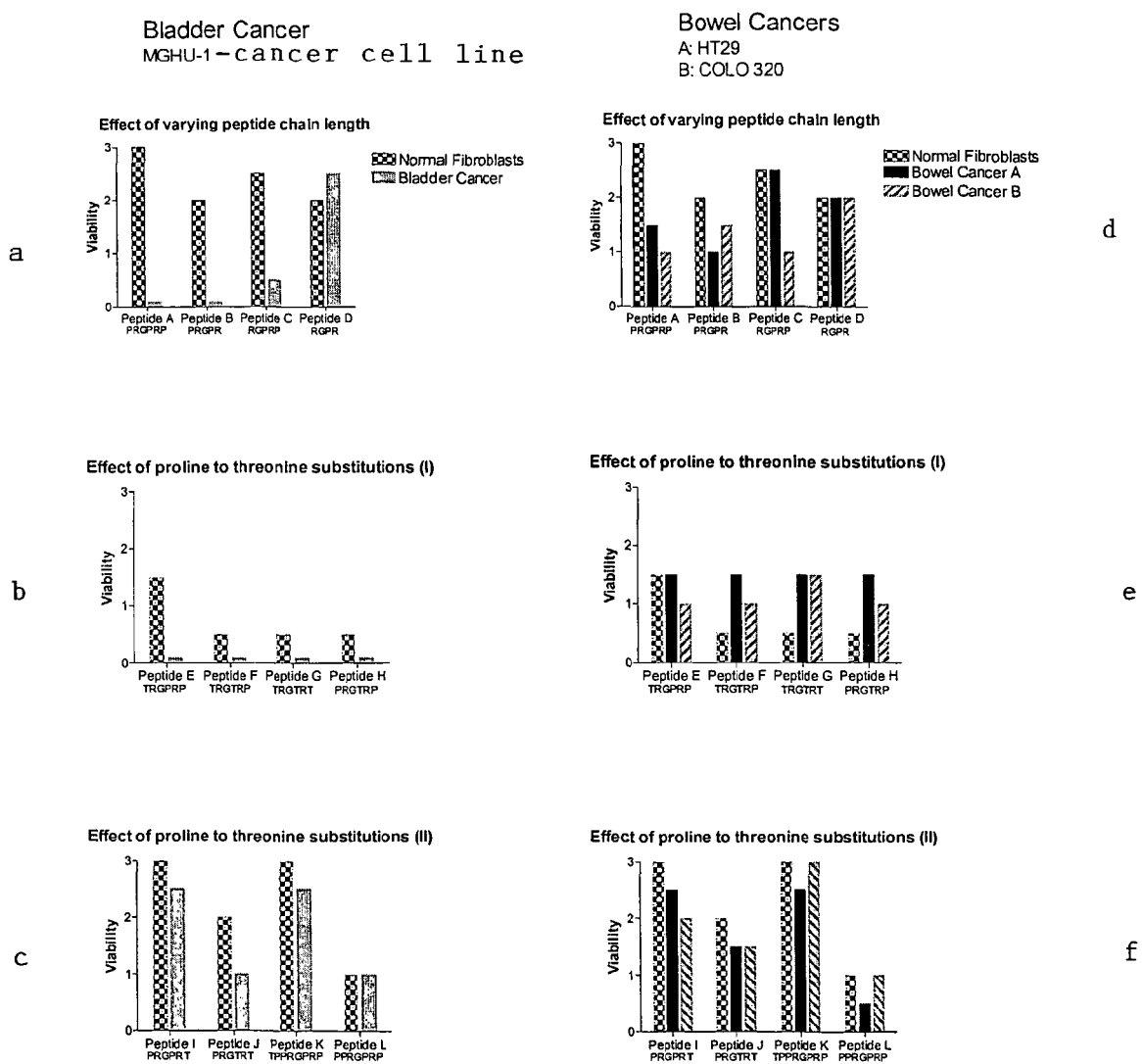
FIG. 15a shows the effect on the viability of RT112 bladder cancer MGHU-1 cell line and normal non-cancerous fibroblasts by treatment with peptide A having the amino acid sequence set out in SEQ ID NO:5, peptide B having the amino acid sequence set out in SEQ ID NO:6, peptide C having the amino acid sequence set out in SEQ ID NO:7 and peptide D having the amino acid sequence set out in SEQ ID NO:8, wherein peptides B to D have varying peptide chain lengths of SEQ ID NO:5.
FIGS. 15b and 15c show the effect on the viability or RT112 bladder cancer MGHU-1 cell line and normal non-cancerous fibroblasts by treatment with peptide E having the amino acid sequence set out in SEQ ID NO:9, peptide F having the amino acid sequence set out in SEQ ID NO:10, peptide G having the amino acid sequence set out in SEQ ID NO:11, peptide H having the amino acid sequence set out in SEQ ID NO:12, peptide I having the amino acid sequence set out in SEQ ID NO:13, peptide J having the amino acid sequence set out in SEQ ID NO:14, peptide K having the amino acid sequence set out in SEQ ID NO:15 and peptide L having the amino acid sequence set out in SEQ ID NO:16, wherein peptides E to L have varying substitutions of proline to threonine with respect to SEQ ID NO:5.
FIG. 15d shows the effect on the viability of Bowel Cancer HT29 cell line (Bowel Cancer A), Bowel Cancer COLO 320 (Bowel Cancer B) and normal non-cancerous fibroblasts by treatment with peptide A having the amino acid sequence set out in SEQ ID NO:5, peptide B having the amino acid sequence set out in SEQ ID NO:6, peptide C having the amino acid sequence set out in SEQ ID NO:7 and peptide D having the amino acid sequence set out in SEQ ID NO:8, wherein peptides B to D have varying peptide chain lengths of SEQ ID NO:5.
FIGS. 15e and f show the effect on the viability of Bowel Cancer HT29 cell line (Bowel Cancer A), Bowel Cancer COLO 320 (Bowel Cancer B) and normal non-cancerous fibroblasts by treatment with peptide E having the amino acid sequence set out in SEQ ID NO:9, peptide F having the amino acid sequence set out in SEQ ID NO:10, peptide G having the amino acid sequence set out in SEQ ID NO:11, peptide H having the amino acid sequence set out in SEQ ID NO:12, peptide I having the amino acid sequence set out in SEQ ID NO:13, peptide J having the amino acid sequence set out in SEQ ID NO:14, peptide K having the amino acid sequence set out in SEQ ID NO:15 and peptide L having the amino acid sequence set out in SEQ ID NO:16, wherein peptides E to L have varying substitutions of proline to threonine with respect to SEQ ID NO:5.

The results of these experiments are shown in FIG. 15

FIGS. 15a, b, c, d, e and f show the selective effect on normal non-cancerous fibroblasts and cancer cells of shorter peptide sequences including shorter sequences in which prolines have been substituted for threonines. These figures show clear relationships between the sequence of the peptide analogous of novel CDK4 C'-terminal partially hydrophobic region and the effect on the cell lines tested.

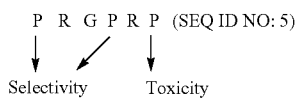

Without being bound by theory it is believed that the presence of proline at amino acid positions 1 and/or 4 (PRGPRP) (SEQ ID NO:5) resulted in improved selectivity of the peptide for the cancer cell lines and higher viability of normal fibroblasts. The presence of proline at amino acid position 6 (PRGPRP) (SEQ ID NO:5) resulted in improved toxicity of the peptide on the cancer cell lines. It is clear that the linear hexamer PRGPRP (SEQ ID NO: 5) shows the greatest selectivity between cancer cell killing and normal cell sparing at 21 days after exposure to 5.0 mM. In addition, normal non-cancerous fibroblasts exposed to PRGPRP (SEQ ID NO:5) grew better than control fibroblasts which were not exposed to any peptide.

EXPERIMENT 5

Clonogenic assay to obtain quantitative data on cancer cell killing by the linear hexamer PRGPRP SEQ ID NO: 5. Clonogenic cell survival assay have already been reported (Warenius H M, Jones M, Gorman T, McLeish R, Seabra L, Barraclough R and Rudland P. Br J Cancer (2000) 83(8), 1084-1095). A single cell suspension of 100 cells of RT112 bladder cancer cells was plated in 2 mls of Hams F12 medium supplemented with 10% fetal calf serum. The Hams F12 medium contained no peptide (control) or the linear hexamer PRG-PRP SEQ ID NO: 5 concentration of 1.0 mM to 5.0 mM. It is conventional to examine clonogenic assays at 10 to 14 days during which time cells have gone through a minimum of 5-7 doublings producing a colony in the site where each single cell has adhered to the tissue culture dish. Because cancer cell death in 96 micro well plate experiments with this peptide was not apparent until 21 days, dishes were incubated for 15, 20 and 25 days. At the end of the incubation period, the medium was removed, colonies fixed in 70% ethanol and stained with giemsa. Colonies of greater than 100 cells were scored as positive. The results shown in FIG. 16 indicate that no cancer cell death is obvious at 15 days but becomes more obvious between 20 and 25 days. In addition the dose response curve is very steep showing a threshold effect as was also observed in 96 well dishes.

Figure 16:
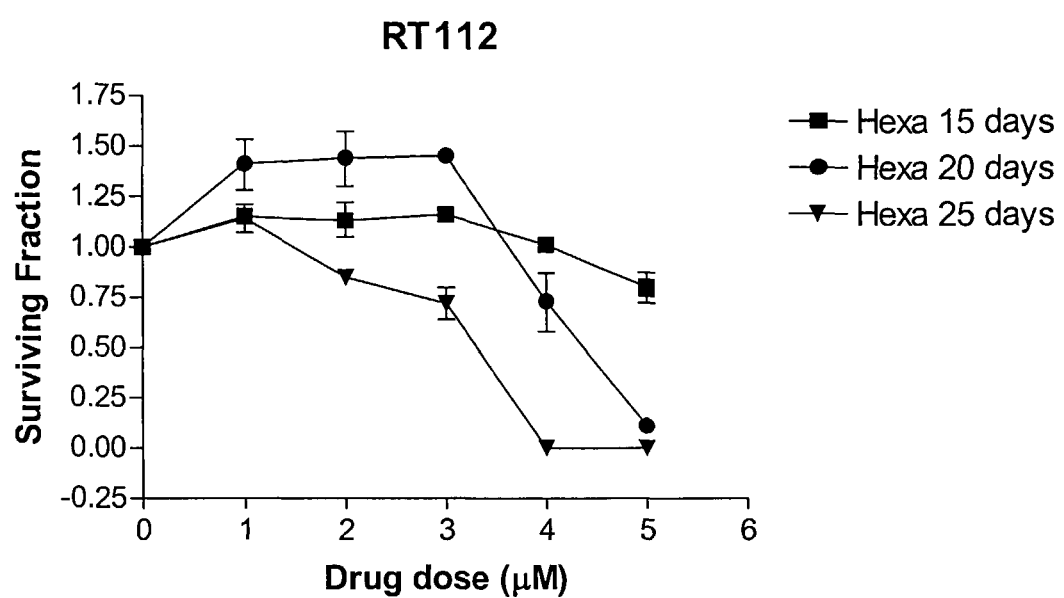
FIG. 16 shows the effect on the surviving fraction of RT112 bladder cancer cells exposed to 1.0 to 5.0 mM of the Hexamer PRGPRP (SEQ ID NO: 5) scored at 15, 20 and 25 days after treatment.

FIG. 16 shows clonogenic assays for RT112 bladder cancer cells exposed to 1.0 to 5.0 mM of the hexamer PRGPRP (SEQ ID NO: 5). Clonogenic assays were scored at 15, 20 and 25 days after treatment. It is shown that with treatment with the hexamer PRGPRP (SEQ ID NO: 5) there was no early killing of the cancerous cells only specific cancer cell killing between days 20 and 25. It is shown in FIG. 16 that early exposure of RT112 bladder cancer cells over 15 days had virtually no effect on cancer cell killing. Visual observation during these 15 days showed that non-cancerous fibroblasts grew well and possibly even better than controls which received no PRGPRP (SEQ ID NO: 5).

EXPERIMENT 6

Cancer cells and non-cancerous fibroblasts were separately seeded at $10^2$ to $10^4$ cells in 200 µl of Hams F12 tissue culture medium plus 10% fetal calf serum in 96 well plates and exposed to varying concentrations of a peptide having an amino acid sequence set out in SEQ ID NO: 17 ranging from 5.0 µM to 100 µM. Cell growth was studied by daily phase-contrast microscopy over 25 days.

Marked stimulation of normal non cancerous fibroblasts was noted between 5 and 10 days after exposure to SEQ ID NO: 17 (see FIG. 18 photographed after 10 days exposure to SEQ ID NO: 17 at a concentration of 10 µM).

This shows that the peptide having the amino acids sequence set out in SEQ ID NO:17 stimulates the growth of normal non-cancerous fibroblasts. Although it does not show complete detachment of dead cells from the plastic surface of the tissue culture vessel, it does cause loss of clear cell morphology which indicates that the cancerous cells are no longer capable of dividing as cancer cells.

Taken in conjunction with the observation by Morris et al (2002 Oncogene 21: 4277) that normal CDK4 has been shown to prolong the proliferative life span of normal non-cancerous human fibroblasts by a mechanism that did not involve the known normal kinase activity of CDK4, without being bound by theory it is believed that peptide analogues of the novel region of CDK4 of the present invention can stimulate the growth of normal cells and therefore have a role in promoting normal cell growth such as in wound healing or in the use of stem cells to repopulate pathologically damaged cells in human degenerative disorders. Such compounds may also directly extend the proliferative life span of diseased cells in human degenerative disorders thus alleviating symptoms and prolonging life.

Figure 17:
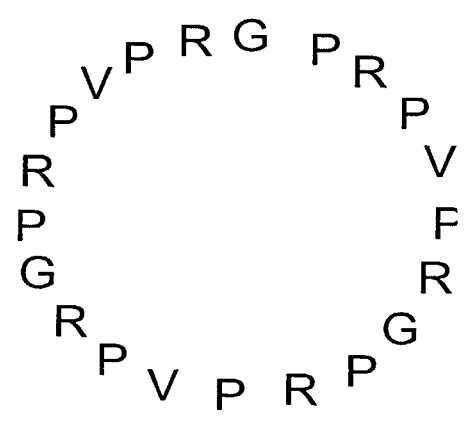

FIG. 17 shows the structure of a cyclic heptamer

```
SEQ ID NO: 17:    cyclo-[PRGPRPVPRGPRPVPRGPRPV]
```

FIG. 18 shows that following 10 days exposure to SEQ ID NO: 17 at a concentration of 10 µM there is marked non-cancerous fibroblast stimulation.

FIG. 19 shows, after 20 days exposure of MGHU-1 bladder cancer cells to SEQ ID NO 17, marked loss of normal cell morphology with very indistinct cell edges and no obvious nuclei. These changes may reflect a senescence. It can be seen from FIG. 19 that the control MGHU-1 bladder cancer cells have clear cell surface and nuclear membranes whereas the treated MGHU-1 bladder cancer cells have the appearance of 'ghost' cells with no clear nuclear demarcation and very indistinct cell borders.

The experiments performed on cultured cells reflect the situation in vivo. This is because in the majority of human cancers, cells are nutrient deprived and non-dividing/quiescent. The experiments described above reflect this situation, since cells in these in vitro experiments are confluent and the majority of cells are non-dividing due to nutrient depletion occurring over the long time of exposure of cells to the peptides during the experiment. Also, the experiments were performed in 96 well plates which results in over-crowded plateau phase cultures occurring over the 25 days of observation. Such experimental conditions are helpful because they reflect the situation of human cancer in vivo.

The invention claimed is:

1. A peptide comprising an amino acid sequence that is:
a) part of the amino acid sequence of CDK4 protein; or
b) homologous to part of the amino acid sequence of CDK4 protein;
which peptide is cytotoxic to, and/or inhibiting to the growth of, a cancer cell and/or stimulating to the growth of a non-cancerous cell and/or a control cell, and wherein said peptide is non-inhibitory to a non-cancerous cell and/or a control cell, and which peptide comprises n amino acid sequences having the general formula (ZRGXRZ)V (SEQ ID NO:40), wherein R is arginine, G is glycine, Z may be present or absent and at least one Z is present, X and Z are independently proline or threonine and at least one of X and/or Z is proline, V is valine and may be present or absent and n is an integer from 2-10; and m further amino acid sequences, each further sequence independently having z amino acids, wherein m is an integer from 0-10 and z is an integer from 1-20, and wherein the peptide further comprises an amino acid sequence facilitating cellular uptake of the peptide; wherein said peptide is more cytotoxic to, or more inhibiting to, the growth of a cancer cell than a control cell and/or a non-cancerous cell.

2. A peptide according to claim 1, wherein n is an integer selected from 2, 3, 4, or 5.

3. A peptide according to claim 2, wherein n is 3.

4. A peptide according to claim 3, which comprises the amino acid sequence PRGPRPVPRGPRPVPRGPRPV (SEQ ID NO:17).

5. A peptide according to claim 1, wherein said peptide is cyclic.

6. A peptide according to claim 1, wherein said CDK4 protein is human CDK4 protein.

7. A peptide according to claim 1 which comprises the amino acid sequence set out in SEQ ID NO:1, or the amino acid sequence set out in SEQ ID NO:2.

8. A peptide consisting of the amino acid sequence set out in SEQ ID NO:1 or the amino acid sequence set out in SEQ ID NO:2.

9. A pharmaceutical composition comprising the peptide of claim 1 or 8, and a pharmaceutical carrier, diluent or excipient.

10. A pharmaceutical composition according to claim 9, further comprising a p53 inhibitor.

11. A pharmaceutical composition according to claim 10, wherein said p53 inhibitor is pifithrin-α.

12. A method of manufacturing a pharmaceutical composition of claim 9, comprising:
   a) providing a peptide;
   b) optionally providing a p53 inhibitor;
   c) manufacturing a pharmaceutical composition comprising said peptide and optionally, said p53 inhibitor.

13. A peptide according to claim 1 or 8 for use in medicine.

14. A peptide according to claim 1 or 8, and a p53 inhibitor as a combined preparation for simultaneous, separate or sequential use in medicine.

15. A method of treating a patient having cancer, comprising treating the patient with a pharmaceutical composition of claim 9.

16. A method according to claim 15, wherein if the cancer contains cells that express wild type p53, the patient is treated with a pharmaceutical composition further comprising a p53 inhibitor.

17. A method according to claim 15, wherein the cancer is breast cancer, prostate cancer, colorectal cancer, bladder cancer, ovarian cancer, endometrial cancer, cervical cancer, head and neck cancer, stomach cancer, pancreatic cancer, oesophagus cancer, small cell lung cancer, non-small cell lung cancer, malignant melanoma, neuroblastoma, leukaemia, lymphoma, sarcoma or glioma.

18. A pharmaceutical composition according to claim 9, further comprising stem cells.

19. A peptide according to claim 1 and stem cells for simultaneous, separate or sequential use in medicine.

* * * * *

SEQUENCE LISTING

<160> NUMBER OF SEQ ID NOS: 64

<210> SEQ ID NO 1
<211> LENGTH: 10
<212> TYPE: PRT
<213> ORGANISM: Artificial Sequence
<220> FEATURE:
<223> OTHER INFORMATION: Peptide fragment of human CDK4

<400> SEQUENCE: 1

Phe Pro Pro Arg Gly Pro Arg Pro Val Gln
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthesized peptide

<400> SEQUENCE: 2

Phe Thr Pro Arg Gly Thr Arg Pro Val Gln
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthesized Peptide

<400> SEQUENCE: 3

Ala Thr Thr Glu Gly Thr Glu Thr Val Gln
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthesized Peptide

<400> SEQUENCE: 4

Pro Gly Pro Phe Arg Val Pro Gln Pro Arg
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 5

Pro Arg Gly Pro Arg Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Synthesized Peptide

<400> SEQUENCE: 6

Pro Arg Gly Pro Arg

-continued

```
<210> SEQ ID NO 7
<211> LENGTH: 5
<212> TYPE: PRT
<213> ORGANISM: Artificial Sequence
<220> FEATURE:
<223> OTHER INFORMATION: Synthesized Peptide

<400> SEQUENCE: 7

Arg Gly Pro Arg Pro
1               5

<210> SEQ ID NO 8
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 8

Arg Gly Pro Arg
1

<210> SEQ ID NO 9
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 9

Thr Arg Gly Pro Arg Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 10

Thr Arg Gly Thr Arg Pro
1               5

<210> SEQ ID NO 11
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 11

Thr Arg Gly Thr Arg Thr
1               5

<210> SEQ ID NO 12
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 12

Pro Arg Gly Thr Arg Pro
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 13

Pro Arg Gly Pro Arg Thr
1               5

<210> SEQ ID NO 14
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 14

Pro Arg Gly Thr Arg Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthesized Peptide

<400> SEQUENCE: 15

Thr Pro Pro Arg Gly Pro Arg Pro
1               5

<210> SEQ ID NO 16
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 16

Pro Pro Arg Gly Pro Arg Pro
1               5

<210> SEQ ID NO 17
<211> LENGTH: 21
<212> TYPE: PRT
<213> ORGANISM: Artificial Sequence
<220> FEATURE:
<223> OTHER INFORMATION: Synthesized Peptide

<400> SEQUENCE: 17

Pro Arg Gly Pro Arg Pro Val Pro Arg Gly Pro Arg Pro Val Pro Arg
1               5                   10                  15

Gly Pro Arg Pro Val
            20

<210> SEQ ID NO 18
<211> LENGTH: 17
<212> TYPE: PRT
<213> ORGANISM: Artificial Sequence
<220> FEATURE:
<223> OTHER INFORMATION: Synthesized Peptide

<400> SEQUENCE: 18

Gly Gly Gly Gly Pro Arg Gly Pro Arg Pro Gly Gly Gly Gly Ala Ala
1               5                   10                  15
```

Ala

<210> SEQ ID NO 19
<211> LENGTH: 28
<212> TYPE: PRT
<213> ORGANISM: Artificial Sequence
<220> FEATURE:
<223> OTHER INFORMATION: Synthesized Peptide

<400> SEQUENCE: 19

Gly Gly Gly Gly Pro Arg Gly Pro Arg Pro Gly Gly Gly Pro Arg
1               5                   10                  15

Gly Pro Arg Pro Val Pro Arg Gly Pro Arg Pro Val
            20                  25

<210> SEQ ID NO 20
<211> LENGTH: 30
<212> TYPE: PRT
<213> ORGANISM: Artificial Sequence
<220> FEATURE:
<223> OTHER INFORMATION: Synthesized Peptide

<400> SEQUENCE: 20

Phe Pro Pro Arg Gly Pro Arg Pro Val Gln Phe Pro Pro Arg Gly Pro
1               5                   10                  15

Arg Pro Val Gln Phe Pro Pro Arg Gly Pro Arg Pro Val Gln
            20                  25                  30

<210> SEQ ID NO 21
<211> LENGTH: 16
<212> TYPE: PRT
<213> ORGANISM: Artificial Sequence
<220> FEATURE:
<223> OTHER INFORMATION: Synthesized Peptide

<400> SEQUENCE: 21

Ala Ala Ala Gly Gly Pro Arg Gly Pro Arg Pro Gly Gly Ala Ala Ala
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthesized Peptide

<400> SEQUENCE: 22

Ala Ala Gly Gly Gly Pro Arg Gly Pro Arg Pro Gly Gly Gly Ala Ala
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 23

Ala Ala Ala Gly Gly Gly Pro Arg Gly Pro Arg Pro Gly Gly Gly Ala
1               5                   10                  15

Ala Ala

<210> SEQ ID NO 24
<211> LENGTH: 18
<212> TYPE: PRT

-continued

<213> ORGANISM: Artificial Sequence
<220> FEATURE:
<223> OTHER INFORMATION: Synthesized Peptide

<400> SEQUENCE: 24

Ala Val Ala Gly Gly Gly Pro Arg Gly Pro Arg Pro Gly Gly Gly Ala
1               5                   10                  15

Val Ala

<210> SEQ ID NO 25
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 25

Gly Gly Gly Gly Gly Gly Pro Arg Gly Pro Arg Pro Gly Gly Gly Gly
1               5                   10                  15

Gly Gly

<210> SEQ ID NO 26
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 26

Ala Ala Ala Ala Ala Ala Pro Arg Gly Pro Arg Pro Ala Ala Ala Ala
1               5                   10                  15

Ala Ala

<210> SEQ ID NO 27
<211> LENGTH: 17
<212> TYPE: PRT
<213> ORGANISM: Artificial Sequence
<220> FEATURE:
<223> OTHER INFORMATION: Synthesized Peptide

<400> SEQUENCE: 27

Ala Ala Ala Ala Pro Arg Gly Pro Arg Pro Ala Ala Ala Ala Val Trp
1               5                   10                  15

Val

<210> SEQ ID NO 28
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 28

Ala Ala Gly Pro Gly Pro Gly Pro Arg Gly Pro Arg Pro Gly Pro Gly
1               5                   10                  15

Ala Ala

<210> SEQ ID NO 29
<211> LENGTH: 18
<212> TYPE: PRT
<213> ORGANISM: Artificial Sequence
<220> FEATURE:
<223> OTHER INFORMATION: Synthesized Peptide

<400> SEQUENCE: 29

```
Ala Ala Gly Pro Gly Gly Pro Arg Gly Pro Arg Pro Gly Pro Gly
1               5                   10                  15

Ala Ala

<210> SEQ ID NO 30
<211> LENGTH: 20
<212> TYPE: PRT
<213> ORGANISM: Artificial Sequence
<220> FEATURE:
<223> OTHER INFORMATION: Synthesized Peptide

<400> SEQUENCE: 30

Ala Ala Val Pro Gly Gly Pro Arg Gly Pro Arg Pro Gly Gly Pro Gly
1               5                   10                  15

Val Ala Ala Val
            20

<210> SEQ ID NO 31
<211> LENGTH: 24
<212> TYPE: PRT
<213> ORGANISM: Artificial Sequence
<220> FEATURE:
<223> OTHER INFORMATION: Synthesized Peptide

<400> SEQUENCE: 31

Gly Gly Pro Arg Gly Pro Arg Pro Gly Gly Pro Arg Gly Pro Arg Pro
1               5                   10                  15

Gly Gly Pro Arg Gly Pro Arg Pro
            20

<210> SEQ ID NO 32
<211> LENGTH: 6
<212> TYPE: PRT
<213> ORGANISM: Artificial Sequence
<220> FEATURE:
<223> OTHER INFORMATION: Peptide Consensus Sequence
<220> FEATURE:
<221> NAME/KEY: MISC_FEATURE
<222> LOCATION: (1)..(1)
<223> OTHER INFORMATION: Xaa may be present or absent and is selected
      from the group consisting of proline or threonine; wherein if Xaa
      is present the Xaa at position 6 may be absent or present; wherein
      if Xaa at position 1 is absent then Xaa at position 6 is present;
<220> FEATURE:
<221> NAME/KEY: MISC_FEATURE
<222> LOCATION: (1)..(1)
<223> OTHER INFORMATION: at least one Xaa at position 1, 4 or 6 is
      proline
<220> FEATURE:
<221> NAME/KEY: misc_feature
<222> LOCATION: (4)..(4)
<223> OTHER INFORMATION: Xaa is proline or threonine; wherein at least
      one Xaa at position 1, 4 or 6 is proline
<220> FEATURE:
<221> NAME/KEY: MISC_FEATURE
<222> LOCATION: (6)..(6)
<223> OTHER INFORMATION: Xaa may be present or absent and is selected
      from the group consisting of proline or threonine; wherein if Xaa
      is present the Xaa at position 1 may be absent or present; wherein
      if Xaa at position 6 is absent then Xaa at position 1 is present
<220> FEATURE:
<221> NAME/KEY: MISC_FEATURE
<222> LOCATION: (6)..(6)
<223> OTHER INFORMATION: At least one Xaa at position 1, 4 or 6 is
      proline

<400> SEQUENCE: 32

Xaa Arg Gly Xaa Arg Xaa
1               5
```

```
<210> SEQ ID NO 33
<211> LENGTH: 6
<212> TYPE: PRT
<213> ORGANISM: Artificial Sequence
<220> FEATURE:
<223> OTHER INFORMATION: Peptide Consensus Sequence
<220> FEATURE:
<221> NAME/KEY: MISC_FEATURE
<222> LOCATION: (3)..(4)
<223> OTHER INFORMATION: Xaa is any amino acid

<400> SEQUENCE: 33

Pro Arg Xaa Xaa Arg Pro
1               5

<210> SEQ ID NO 34
<211> LENGTH: 7
<212> TYPE: PRT
<213> ORGANISM: Artificial Sequence
<220> FEATURE:
<223> OTHER INFORMATION: Peptide Consensus Sequence
<220> FEATURE:
<221> NAME/KEY: MISC_FEATURE
<222> LOCATION: (4)..(4)
<223> OTHER INFORMATION: Xaa is any amino acid

<400> SEQUENCE: 34

Pro Pro Arg Xaa Pro Arg Pro
1               5

<210> SEQ ID NO 35
<211> LENGTH: 6
<212> TYPE: PRT
<213> ORGANISM: Artificial Sequence
<220> FEATURE:
<223> OTHER INFORMATION: Peptide Consensus Sequence
<220> FEATURE:
<221> NAME/KEY: MISC_FEATURE
<222> LOCATION: (3)..(3)
<223> OTHER INFORMATION: Xaa is any amino acid

<400> SEQUENCE: 35

Pro Arg Xaa Pro Arg Pro
1               5

<210> SEQ ID NO 36
<211> LENGTH: 7
<212> TYPE: PRT
<213> ORGANISM: Artificial Sequence
<220> FEATURE:
<223> OTHER INFORMATION: Peptide Consensus Sequence
<220> FEATURE:
<221> NAME/KEY: MISC_FEATURE
<222> LOCATION: (5)..(5)
<223> OTHER INFORMATION: Xaa is any amino acid

<400> SEQUENCE: 36

Pro Pro Arg Gly Xaa Arg Pro
1               5

<210> SEQ ID NO 37
<211> LENGTH: 7
<212> TYPE: PRT
<213> ORGANISM: Artificial Sequence
<220> FEATURE:
<223> OTHER INFORMATION: Peptide Consensus Sequence
<220> FEATURE:
<221> NAME/KEY: MISC_FEATURE
<222> LOCATION: (4)..(4)
<223> OTHER INFORMATION: Xaa is any amino acid
```

-continued

```
<400> SEQUENCE: 37

Pro Arg Gly Xaa Pro Arg Pro
1               5

<210> SEQ ID NO 38
<211> LENGTH: 7
<212> TYPE: PRT
<213> ORGANISM: Artificial Sequence
<220> FEATURE:
<223> OTHER INFORMATION: Peptide Consensus Sequence
<220> FEATURE:
<221> NAME/KEY: MISC_FEATURE
<222> LOCATION: (4)..(5)
<223> OTHER INFORMATION: Xaa is any amino acid

<400> SEQUENCE: 38

Pro Pro Arg Xaa Xaa Arg Pro
1               5

<210> SEQ ID NO 39
<211> LENGTH: 6
<212> TYPE: PRT
<213> ORGANISM: Artificial Sequence
<220> FEATURE:
<223> OTHER INFORMATION: Peptide Consensus Sequence
<220> FEATURE:
<221> NAME/KEY: MISC_FEATURE
<222> LOCATION: (3)..(4)
<223> OTHER INFORMATION: Xaa is any amino acid

<400> SEQUENCE: 39

Pro Arg Xaa Xaa Arg Pro
1               5

<210> SEQ ID NO 40
<211> LENGTH: 7
<212> TYPE: PRT
<213> ORGANISM: Artificial Sequence
<220> FEATURE:
<223> OTHER INFORMATION: Peptide Consensus Sequence
<220> FEATURE:
<221> NAME/KEY: MISC_FEATURE
<222> LOCATION: (1)..(1)
<223> OTHER INFORMATION: Xaa may be present or absent and is selected
      from the group consisting of proline or threonine; wherein if Xaa
      is present the Xaa at position 6 may be absent or present; wherein
      if Xaa at position 1 is absent then Xaa at position 6 is present
<220> FEATURE:
<221> NAME/KEY: MISC_FEATURE
<222> LOCATION: (1)..(1)
<223> OTHER INFORMATION: wherein at least one Xaa at position 1, 4 or 6
      is proline
<220> FEATURE:
<221> NAME/KEY: REPEAT
<222> LOCATION: (1)..(7)
<220> FEATURE:
<221> NAME/KEY: MISC_FEATURE
<222> LOCATION: (4)..(4)
<223> OTHER INFORMATION: Xaa is Proline or threonine; wherein at least
      one Xaa at position 1, 4 or 6 is proline
<220> FEATURE:
<221> NAME/KEY: MISC_FEATURE
<222> LOCATION: (6)..(6)
<223> OTHER INFORMATION: Xaa may be present or absent and is selected
      from the group consisting of proline or threonine; wherein if Xaa
      is present the Xaa at position 1 may be absent or present; wherein
      if Xaa at position 6 is absent then Xaa at position 1 is present
<220> FEATURE:
<221> NAME/KEY: MISC_FEATURE
<222> LOCATION: (6)..(6)
<223> OTHER INFORMATION: wherein at least one Xaa at position 1, 4 or 6
      is proline
<220> FEATURE:
<221> NAME/KEY: MISC_FEATURE
```

```
<222> LOCATION: (7)..(7)
<223> OTHER INFORMATION: Xaa is valine and may be absent or present

<400> SEQUENCE: 40

Xaa Arg Gly Xaa Arg Xaa Xaa
1               5

<210> SEQ ID NO 41
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 41

Gly Gly Gly Gly
1

<210> SEQ ID NO 42
<211> LENGTH: 5
<212> TYPE: PRT
<213> ORGANISM: Artificial Sequence
<220> FEATURE:
<223> OTHER INFORMATION: Synthesized Peptide

<400> SEQUENCE: 42

Gly Gly Gly Gly Gly
1               5

<210> SEQ ID NO 43
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 43

Gly Gly Gly Gly Gly Gly
1               5

<210> SEQ ID NO 44
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 44

Ala Ala Ala Ala
1

<210> SEQ ID NO 45
<211> LENGTH: 5
<212> TYPE: PRT
<213> ORGANISM: Artificial Sequence
<220> FEATURE:
<223> OTHER INFORMATION: Synthesized Peptide

<400> SEQUENCE: 45

Ala Ala Ala Ala Ala
1               5

<210> SEQ ID NO 46
<211> LENGTH: 6
<212> TYPE: PRT
<213> ORGANISM: Artificial Sequence
<220> FEATURE:
<223> OTHER INFORMATION: Synthesized Peptide
```

<400> SEQUENCE: 46

Ala Ala Ala Ala Ala Ala
1               5

<210> SEQ ID NO 47
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 47

Val Val Val Val
1

<210> SEQ ID NO 48
<211> LENGTH: 5
<212> TYPE: PRT
<213> ORGANISM: Artificial Sequence
<220> FEATURE:
<223> OTHER INFORMATION: Synthesized Peptide

<400> SEQUENCE: 48

Val Val Val Val Val
1               5

<210> SEQ ID NO 49
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 49

Val Val Val Val Val Val
1               5

<210> SEQ ID NO 50
<211> LENGTH: 16
<212> TYPE: PRT
<213> ORGANISM: Artificial Sequence
<220> FEATURE:
<223> OTHER INFORMATION: Synthesized Peptide

<400> SEQUENCE: 50

Arg Gln Ile Lys Ile Trp Phe Gln Asn Arg Arg Met Lys Trp Lys Lys
1               5                   10                  15

<210> SEQ ID NO 51
<211> LENGTH: 17
<212> TYPE: PRT
<213> ORGANISM: Artificial Sequence
<220> FEATURE:
<223> OTHER INFORMATION: Synthesized Peptide

<400> SEQUENCE: 51

Lys Lys Trp Lys Met Arg Arg Asn Gln Phe Trp Val Lys Val Gln Arg
1               5                   10                  15

Gly

<210> SEQ ID NO 52
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 52

Leu Thr Val Ser Pro Trp Tyr
1               5

<210> SEQ ID NO 53
<211> LENGTH: 12
<212> TYPE: PRT
<213> ORGANISM: Artificial Sequence
<220> FEATURE:
<223> OTHER INFORMATION: Peptide Fragment of p27 protein

<400> SEQUENCE: 53

Phe Tyr Tyr Arg Pro Pro Arg Pro Pro Lys Gly Ala
1               5                   10

<210> SEQ ID NO 54
<211> LENGTH: 298
<212> TYPE: PRT
<213> ORGANISM: Homo sapiens

<400> SEQUENCE: 54

Met Glu Asn Phe Gln Lys Val Glu Lys Ile Gly Glu Gly Thr Tyr Gly
1               5                   10                  15

Val Val Tyr Lys Ala Arg Asn Lys Leu Thr Gly Glu Val Val Ala Leu
                20                  25                  30

Lys Lys Ile Arg Leu Asp Thr Glu Thr Glu Gly Val Pro Ser Thr Ala
            35                  40                  45

Ile Arg Glu Ile Ser Leu Leu Lys Glu Leu Asn His Pro Asn Ile Val
50                  55                  60

Lys Leu Leu Asp Val Ile His Thr Glu Asn Lys Leu Tyr Leu Val Phe
65                  70                  75                  80

Glu Phe Leu His Gln Asp Leu Lys Lys Phe Met Asp Ala Ser Ala Leu
                85                  90                  95

Thr Gly Ile Pro Leu Pro Leu Ile Lys Ser Tyr Leu Phe Gln Leu Leu
            100                 105                 110

Gln Gly Leu Ala Phe Cys His Ser His Arg Val Leu His Arg Asp Leu
        115                 120                 125

Lys Pro Gln Asn Leu Leu Ile Asn Thr Glu Gly Ala Ile Lys Leu Ala
130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Ser Lys Tyr Tyr Ser Thr Ala Val Asp Ile Trp Ser Leu Gly Cys Ile
            180                 185                 190

Phe Ala Glu Met Val Thr Arg Arg Ala Leu Phe Pro Gly Asp Ser Glu
        195                 200                 205

Ile Asp Gln Leu Phe Arg Ile Phe Arg Thr Leu Gly Thr Pro Asp Glu
210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
            260                 265                 270

Lys Arg Ile Ser Ala Lys Ala Ala Leu Ala His Pro Phe Phe Gln Asp
        275                 280                 285

```
Val Thr Lys Pro Val Pro His Leu Arg Leu
    290                 295
```

<210> SEQ ID NO 55
<211> LENGTH: 303
<212> TYPE: PRT
<213> ORGANISM: Homo sapiens

<400> SEQUENCE: 55

```
Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Gly Gly Gly Gly Gly Gly
        35                  40                  45

Leu Pro Ile Ser Thr Val Arg Glu Val Ala Leu Leu Arg Arg Leu Glu
    50                  55                  60

Ala Phe Glu His Pro Asn Val Val Arg Leu Met Asp Val Cys Ala Thr
65              70                  75                  80

Ser Arg Thr Asp Arg Glu Ile Lys Val Thr Leu Val Phe Glu His Val
            85                  90                  95

Asp Gln Asp Leu Arg Thr Tyr Leu Asp Lys Ala Pro Pro Pro Gly Leu
            100                 105                 110

Pro Ala Glu Thr Ile Lys Asp Leu Met Arg Gln Phe Leu Arg Gly Leu
        115                 120                 125

Asp Phe Leu His Ala Asn Cys Ile Val His Arg Asp Leu Lys Pro Glu
    130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205

Arg Arg Lys Pro Leu Phe Cys Gly Asn Ser Glu Ala Asp Gln Leu Gly
    210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
        275                 280                 285

Ala Leu Gln His Ser Tyr Leu His Lys Asp Glu Gly Asn Pro Glu
    290                 295                 300
```

<210> SEQ ID NO 56
<211> LENGTH: 326
<212> TYPE: PRT
<213> ORGANISM: Homo sapiens

<400> SEQUENCE: 56

```
Met Glu Lys Asp Gly Leu Cys Arg Ala Asp Gln Gln Tyr Glu Cys Val
1               5                   10                  15
```

```
Ala Glu Ile Gly Glu Gly Ala Tyr Gly Lys Val Phe Lys Ala Arg Asp
             20                  25                  30

Leu Lys Asn Gly Gly Arg Phe Val Ala Leu Lys Arg Val Arg Val Gln
         35                  40                  45

Thr Gly Glu Glu Gly Met Pro Leu Ser Thr Ile Arg Glu Val Ala Val
     50                  55                  60

Leu Arg His Leu Glu Thr Phe Glu His Pro Asn Val Val Arg Leu Phe
 65                  70                  75                  80

Asp Val Cys Thr Val Ser Arg Thr Asp Arg Glu Thr Lys Leu Thr Leu
                 85                  90                  95

Val Phe Glu His Val Asp Gln Asp Leu Thr Thr Tyr Leu Asp Lys Val
             100                 105                 110

Pro Glu Pro Gly Val Pro Thr Glu Thr Ile Lys Asp Met Met Phe Gln
         115                 120                 125

Leu Leu Arg Gly Leu Asp Phe Leu His Ser His Arg Val Val His Arg
     130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
        195                 200                 205

Phe Ala Glu Met Phe Arg Arg Lys Pro Leu Phe Arg Gly Ser Ser Asp
    210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
        275                 280                 285

Ile Ser Ala Tyr Ser Ala Leu Ser His Pro Tyr Phe Gln Asp Leu Glu
    290                 295                 300

Arg Cys Lys Glu Asn Leu Asp Ser His Leu Pro Pro Ser Gln Asn Thr
305                 310                 315                 320

Ser Glu Leu Asn Thr Ala
                325

<210> SEQ ID NO 57
<211> LENGTH: 303
<212> TYPE: PRT
<213> ORGANISM: Sus scrofa

<400> SEQUENCE: 57

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Gly Gly Ala Gly Gly Gly
        35                  40                  45

Leu Pro Ile Ser Thr Val Arg Glu Val Ala Leu Leu Arg Arg Leu Glu
    50                  55                  60
```

```
Ala Phe Glu His Pro Asn Val Val Arg Leu Met Asp Val Cys Ala Thr
 65                  70                  75                  80

Ala Arg Thr Asp Arg Glu Thr Lys Val Thr Leu Val Phe Glu His Val
                 85                  90                  95

Asp Gln Asp Leu Arg Thr Tyr Leu Asp Lys Ala Pro Pro Gly Leu
            100                 105                 110

Pro Val Glu Thr Ile Lys Asp Leu Met Arg Gln Phe Leu Arg Gly Leu
            115                 120                 125

Asp Phe Leu His Ala Asn Cys Ile Val His Arg Asp Leu Lys Pro Glu
            130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
                180                 185                 190

Thr Pro Val Asp Met Trp Ser Val Gly Cys Ile Phe Ala Glu Met Phe
            195                 200                 205

Arg Arg Lys Pro Leu Phe Cys Gly Asn Ser Glu Ala Asp Gln Leu Gly
210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Ser Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
            275                 280                 285

Ala Leu Gln His Ser Tyr Leu His Lys Ala Glu Gly Asn Pro Glu
            290                 295                 300

<210> SEQ ID NO 58
<211> LENGTH: 303
<212> TYPE: PRT
<213> ORGANISM: Rattus norvegicus

<400> SEQUENCE: 58

Met Ala Thr Thr Arg Tyr Glu Pro Val Ala Glu Ile Gly Val Gly Ala
  1               5                  10                  15

Tyr Gly Thr Val Tyr Lys Ala Arg Asp Pro His Ser Gly His Phe Val
                 20                  25                  30

Ala Leu Lys Ser Val Arg Val Pro Asn Gly Ala Ala Gly Gly Gly Gly
             35                  40                  45

Leu Pro Val Ser Thr Val Arg Glu Val Ala Leu Leu Arg Arg Leu Glu
 50                  55                  60

Ala Phe Glu His Pro Asn Val Val Arg Leu Met Asp Val Cys Ala Thr
 65                  70                  75                  80

Ser Arg Thr Asp Arg Asp Ile Lys Val Thr Leu Val Phe Glu His Ile
                 85                  90                  95

Asp Gln Asp Leu Arg Thr Tyr Leu Asp Lys Ala Pro Pro Gly Leu
            100                 105                 110

Pro Val Glu Thr Ile Lys Asp Leu Met Arg Gln Phe Leu Ser Gly Leu
            115                 120                 125

Asp Phe Leu His Ala Asn Cys Ile Val His Arg Asp Leu Lys Pro Glu
            130                 135                 140
```

```
Asn Ile Leu Val Thr Ser Asn Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205

Arg Arg Lys Pro Leu Phe Cys Gly Asn Ser Glu Ala Asp Gln Leu Gly
    210                 215                 220

Lys Ile Phe Asp Leu Ile Gly Leu Pro Pro Glu Asp Asp Trp Pro Arg
225                 230                 235                 240

Glu Val Ser Leu Pro Arg Gly Ala Phe Ser Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro Leu Lys Arg Ile Ser Ala Phe Arg
        275                 280                 285

Ala Leu Gln His Ser Tyr Leu His Lys Glu Ser Asp Pro Glu
    290                 295                 300

<210> SEQ ID NO 59
<211> LENGTH: 303
<212> TYPE: PRT
<213> ORGANISM: Mus musculus

<400> SEQUENCE: 59

Met Ala Ala Thr Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Gly Ala Ala Gly Gly Gly
            35                  40                  45

Leu Pro Val Ser Thr Val Arg Glu Val Ala Leu Leu Arg Arg Leu Glu
50                  55                  60

Ala Phe Glu His Pro Asn Val Val Arg Leu Met Asp Val Cys Ala Thr
65                  70                  75                  80

Ser Arg Thr Asp Arg Asp Ile Lys Val Thr Leu Val Phe Glu His Ile
                85                  90                  95

Asp Gln Asp Leu Arg Thr Tyr Leu Asp Lys Ala Pro Pro Pro Gly Leu
            100                 105                 110

Pro Val Glu Thr Ile Lys Asp Leu Met Arg Gln Phe Leu Ser Gly Leu
        115                 120                 125

Asp Phe Leu His Ala Asn Cys Ile Val His Arg Asp Leu Lys Pro Glu
    130                 135                 140

Asn Ile Leu Val Thr Ser Asn Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205

Arg Arg Lys Pro Leu Phe Cys Gly Asn Ser Glu Ala Asp Gln Leu Gly
    210                 215                 220
```

```
Lys Ile Phe Asp Leu Ile Gly Leu Pro Pro Glu Asp Trp Pro Arg
225                 230                 235                 240

Glu Val Ser Leu Pro Arg Gly Ala Phe Ala Pro Arg Gly Pro Arg Pro
            245                 250                 255

Val Gln Ser Val Val Pro Glu Met Glu Glu Ser Gly Ala Gln Leu Leu
        260                 265                 270

Leu Glu Met Leu Thr Phe Asn Pro His Lys Arg Ile Ser Ala Phe Arg
            275                 280                 285

Ala Leu Gln His Ser Tyr Leu His Lys Glu Glu Ser Asp Ala Glu
        290                 295                 300
```

<210> SEQ ID NO 60
<211> LENGTH: 319
<212> TYPE: PRT
<213> ORGANISM: Xenopus laevis

<400> SEQUENCE: 60

```
Met Ser Lys Glu Met Lys Gly Gln Tyr Glu Pro Val Ala Glu Ile Gly
1               5                   10                  15

Val Gly Ala Tyr Gly Thr Val Tyr Lys Ala Arg Asp Leu Gln Ser Gly
            20                  25                  30

Lys Phe Val Ala Leu Lys Asn Val Arg Val Gln Thr Asn Glu Asn Gly
        35                  40                  45

Leu Pro Leu Ser Thr Val Arg Glu Val Thr Leu Leu Lys Arg Leu Glu
    50                  55                  60

His Phe Asp His Pro Asn Ile Val Lys Leu Met Asp Val Cys Ala Ser
65                  70                  75                  80

Ala Arg Thr Asp Arg Glu Thr Lys Val Thr Leu Val Phe Glu His Val
                85                  90                  95

Asp Gln Asp Leu Lys Thr Tyr Leu Ser Lys Val Pro Pro Gly Leu
            100                 105                 110

Pro Leu Glu Thr Ile Lys Asp Leu Met Lys Gln Phe Leu Ser Gly Leu
        115                 120                 125

Glu Phe Leu His Leu Asn Cys Ile Val His Arg Asp Leu Lys Pro Glu
130                 135                 140

Asn Ile Leu Val Thr Ser Gly Gly Gln Val Lys Leu Ala Asp Phe Gly
145                 150                 155                 160

Leu Ala Arg Ile Tyr Ser Cys Gln Met Ala Leu Thr Pro Val Val Val
                165                 170                 175

Thr Leu Trp Tyr Arg Ala Pro Gly Val Leu Leu Gln Ser Thr Tyr Ala
            180                 185                 190

Thr Pro Val Asp Val Trp Ser Ala Gly Cys Ile Phe Ala Glu Met Phe
        195                 200                 205

Lys Arg Lys Pro Leu Phe Cys Gly Asn Ser Glu Ala Asp Gln Leu Cys
210                 215                 220

Lys Ile Phe Asp Ile Ile Gly Leu Pro Ser Glu Glu Trp Pro Val
225                 230                 235                 240

Asp Val Thr Leu Pro Arg Ser Ala Phe Ser Pro Arg Thr Gln Gln Pro
            245                 250                 255

Val Asp Lys Phe Val Pro Glu Ile Asp Ala Met Gly Ala Asp Leu Leu
        260                 265                 270

Leu Ala Met Leu Thr Phe Ser Pro Gln Lys Arg Ile Ser Ala Ser Asp
            275                 280                 285

Ala Leu Leu His Pro Phe Phe Ala Asp Asp Pro Gln Ala Cys Ser Lys
        290                 295                 300
```

```
Gln Glu His Phe Thr His Ile Cys Thr Ala Thr Asp Glu Val Lys
305                 310                 315
```

<210> SEQ ID NO 61
<211> LENGTH: 303
<212> TYPE: PRT
<213> ORGANISM: Mus musculus

<400> SEQUENCE: 61

```
Met Ala Ala Thr Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Arg Cys Glu Val Pro Asn Gly Gly Ala Gly Gly Gly Gly
        35                  40                  45

Leu Pro Val Ser Thr Val Arg Glu Val Ala Leu Leu Arg Arg Leu Glu
    50                  55                  60

Ala Phe Glu His Pro Asn Val Val Arg Leu Met Asp Val Cys Ala Asn
65                  70                  75                  80

Ser Arg Thr Asp Arg Asp Ile Lys Val Thr Leu Met Phe Glu His Ile
                85                  90                  95

Asn Gln Asp Leu Arg Thr Tyr Pro Asp Lys Thr Pro Pro Pro Gly Leu
            100                 105                 110

Pro Val Glu Thr Ile Lys Asp Leu Met Arg Gln Phe Leu Ser Ala Leu
        115                 120                 125

Asp Phe Leu His Ala Asn Cys Ile Val His Arg Asp Leu Lys Pro Glu
    130                 135                 140

Asn Ile Leu Val Thr Ser Asn Gly Thr Val Lys Leu Ala Asp Phe Gly
145                 150                 155                 160

Leu Ala Lys Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205

Arg Arg Thr Ala Leu Phe Cys Gly Asn Ser Glu Ala Asp Gln Leu Gly
    210                 215                 220

Lys Ile Phe Asp Leu Ile Gly Leu Pro Pro Glu Asp Asp Trp Pro Arg
225                 230                 235                 240

Glu Val Ser Leu Pro Arg Gly Ala Phe Ala Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Ser Arg
        275                 280                 285

Ala Leu Gln His Ser Tyr Leu His Lys Glu Glu Ser Asp Ala Glu
    290                 295                 300
```

<210> SEQ ID NO 62
<211> LENGTH: 317
<212> TYPE: PRT
<213> ORGANISM: Drosophila melanogaster

<400> SEQUENCE: 62

```
Met Ser Tyr Val Arg Gln Leu Lys Arg Gln Lys Met Ser Gln Ala Lys
1               5                   10                  15

Lys Phe Gly Asp Gly Asp Pro Phe Asn Tyr Gln Glu Leu Asn Ile Ile
```

```
                    20                  25                  30
Gly Glu Gly Ala Tyr Gly Thr Val Tyr Arg Ala Arg Asp Val Ile Thr
            35                  40                  45

Gly Asn Ile Val Ala Leu Lys Lys Val Arg Ile Ser Leu Asn Glu Asn
        50                  55                  60

Gly Val Pro Met Ser Thr Leu Arg Glu Ile Ser Leu Leu Lys Gln Leu
65                  70                  75                  80

Asn Ala Ser Asn His Ala Asn Ile Val Lys Leu Tyr Glu Val Cys Gln
                85                  90                  95

Phe Leu Glu Arg Asp Gly Gln Leu Leu Ile Leu Leu Ala Phe Glu His
            100                 105                 110

Val Glu Gln Asp Leu Ser Asp Leu Ile Asp Arg Leu Pro Lys Ser Gly
        115                 120                 125

Met Ser Pro Pro Thr Ile Gln Arg Leu Ser Arg Glu Leu Leu Thr Gly
130                 135                 140

Val Asp Phe Leu His Ser His Arg Ile Ile His Arg Asp Leu Lys Pro
145                 150                 155                 160

Gln Asn Leu Leu Val Ser Ser Gln Gly His Leu Lys Ile Ala Asp Phe
                165                 170                 175

Gly Leu Ala Lys Thr Tyr Gly Ser Glu Met Lys Leu Thr Ser Val Val
            180                 185                 190

Val Thr Leu Trp Tyr Arg Ala Pro Glu Val Leu Leu Ala Gln Pro Tyr
        195                 200                 205

Asn Ser Thr Val Asp Ile Trp Ser Ala Ala Cys Ile Ile Phe Glu Met
210                 215                 220

Phe Asn Arg Arg Ala Leu Phe Pro Gly Thr Ser Glu Lys Asn Gln Leu
225                 230                 235                 240

Asp Arg Ile Phe Glu Leu Thr Gly Arg Pro Thr Glu Gln Gln Trp Pro
                245                 250                 255

Gln Thr Ile Ser Val Ala Leu Glu His Phe Pro Gln Arg His Pro Lys
            260                 265                 270

Arg Pro Lys Asp Phe Cys Pro His Leu Cys Lys Tyr Ala Asp Asp Leu
        275                 280                 285

Leu Asn Lys Met Leu Ser Tyr Asp Leu His Leu Arg Pro Ser Ala Leu
290                 295                 300

Ala Cys Leu Glu His Asp Tyr Phe Gln Gln Pro Leu
305                 310                 315

<210> SEQ ID NO 63
<211> LENGTH: 371
<212> TYPE: PRT
<213> ORGANISM: Lytechinus veriegatus

<400> SEQUENCE: 63

Met Ala Ser Pro Val Pro Ser Gln Ser Ser Pro Glu Arg Tyr Val Gln
1               5                   10                  15

Ala Ala Glu Ile Gly Ser Gly Ala Tyr Gly Ile Val Tyr Lys Ala Arg
            20                  25                  30

Asp Thr Glu Thr Gly His Phe Val Ala Leu Lys Ser Val Arg Ile Pro
        35                  40                  45

Ile Gly Glu Glu Gly Met Pro Val Ser Thr Ile Arg Glu Ile Ser Leu
    50                  55                  60

Leu Arg His Leu Cys Gln Leu Asp His Pro Asn Ile Val Lys Leu Leu
65                  70                  75                  80

Asp Val Cys Asp Val Met Asp Val Gly Arg Ser Glu Met Met Leu Thr
```

Leu Val Phe Glu Leu Val Asp Gln Asp Leu Ala Gln Tyr Leu Glu Arg
            85                  90                  95

Cys Pro Pro Pro Gly Leu Ser Ser Thr Ile Lys Val Leu Met Gln
        100                 105                 110

Gln Leu Leu Ser Gly Val Glu Tyr Leu His Ser His Arg Val Thr His
    115                 120                 125

Arg Asp Leu Lys Pro Gln Asn Ile Leu Ile Ala Cys Asp Lys Lys Leu
145                 150                 155                 160

Lys Leu Thr Asp Phe Gly Leu Ser Arg Val Tyr Ser Phe Gln Met Ala
                165                 170                 175

Leu Thr Pro Val Val Thr Met Trp Tyr Arg Ala Pro Glu Val Leu
            180                 185                 190

Leu Gln Ala Ser Tyr Ala Thr Pro Val Asp Met Trp Ser Val Gly Cys
        195                 200                 205

Ile Phe Ala Glu Leu His Arg Arg Pro Leu Phe Arg Gly Gln Ser
    210                 215                 220

Asp Lys Asp Gln Leu His Lys Ile Phe Glu Val Ile Gly Leu Pro Pro
225                 230                 235                 240

Glu Asp Gln Trp Pro Asp Val Ala Leu Pro Trp Ser Phe Arg Gln
                245                 250                 255

Thr Gly Gln Arg Ser Phe Leu Asp Leu Val Gln Glu Ile Cys Asn His
            260                 265                 270

Gly Leu Asp Leu Leu Glu Arg Met Leu Cys Phe Asn Pro Asp His Arg
        275                 280                 285

Ile Thr Ala Glu Gln Ser Leu Ser His Ser Tyr Phe Asp Asp Glu Gln
    290                 295                 300

Gly Asp Glu Glu Glu Glu Asp Asp Asp Thr Glu Val Glu Glu Glu
305                 310                 315                 320

Asp Asp Asp Glu Gly Val Asp Val Gly Gln Glu Arg Ser Leu Ser Val
                325                 330                 335

Ala Ser Ser Arg Met Ser Leu Ser Thr Asp Asp Ser Gly Ser His Ser
            340                 345                 350

Gln Phe Gly Val Ser Asp Asp Ser Gln Ser Gln Glu Ile Thr Pro Thr
        355                 360                 365

Asn Val Arg
    370

<210> SEQ ID NO 64
<211> LENGTH: 373
<212> TYPE: PRT
<213> ORGANISM: Strongylocentrotus purpuratus

<400> SEQUENCE: 64

Met Ala Ser Ser Val Pro Ser Arg Ser Thr Pro Glu Arg Tyr Val Gln
1               5                   10                  15

Ala Ala Glu Ile Gly Ser Gly Ala Tyr Gly Ile Val Tyr Lys Ala Arg
            20                  25                  30

Asp Thr Glu Thr Gly His Phe Val Ala Leu Lys Ser Val Arg Ile Pro
        35                  40                  45

Ile Gly Glu Glu Gly Met Pro Val Ser Thr Ile Arg Glu Ile Ser Leu
    50                  55                  60

Leu Arg His Leu Cys Gln Leu Asp His Pro Asn Ile Val Lys Leu Leu
65                  70                  75                  80

Asp Val Cys Asp Val Met Asp Val Gly Arg Ser Glu Met Met Leu Thr

```
                    85                  90                  95
Leu Val Phe Glu Leu Val Asp Gln Asp Leu Ala Gln Tyr Leu Glu Lys
                100                 105                 110

Cys Pro Pro Pro Gly Leu Ser Ser Cys Thr Ile Lys Phe Leu Met His
            115                 120                 125

Gln Leu Leu Ser Gly Val Glu Tyr Leu His Ser His Arg Val Thr His
        130                 135                 140

Arg Asp Leu Lys Pro Gln Asn Ile Leu Val Ala Ser Asp Lys Lys Leu
145                 150                 155                 160

Lys Leu Thr Asp Phe Gly Leu Ser Arg Val Tyr Ser Phe Gln Met Ala
                165                 170                 175

Leu Thr Pro Val Val Val Thr Met Trp Tyr Arg Ala Pro Glu Val Leu
                180                 185                 190

Leu Gln Ala Ser Tyr Ala Thr Pro Val Asp Met Trp Ser Val Gly Cys
            195                 200                 205

Ile Phe Ala Glu Leu Tyr Arg Arg Arg Pro Leu Phe Arg Gly Gln Ser
        210                 215                 220

Asp Lys Asp Gln Leu His Lys Ile Phe Glu Val Ile Gly Leu Pro Pro
225                 230                 235                 240

Glu Asp Gln Trp Pro Asp Val Ala Leu Pro Trp Ser Ser Phe Arg Gln
                245                 250                 255

Thr Gly Gln Arg Ser Phe Leu Asp Leu Val Gln Glu Ile Cys Asn Gln
                260                 265                 270

Gly Leu Asp Leu Leu Glu Arg Met Leu Cys Phe Asn Pro Asp His Arg
            275                 280                 285

Met Thr Ala Glu Gln Gly Leu Leu His Gly Phe Phe Gly Asp Glu Glu
        290                 295                 300

Glu Asp Asp Glu Glu Asp Asp Asp Thr Glu Val Glu Asp Asp Asp Asp
305                 310                 315                 320

Glu Glu Asp Glu Asp Asp Glu Gly Val Asp Val Gly Gln Glu Arg Ser
                325                 330                 335

Gln Ser Ala Ser Thr Ser Ser Met Ser Gln Ala Thr Asp Asp Ser Gly
            340                 345                 350

Ser His Ser Gln Phe Phe Ser Asp Ser Ser Gln Ser Gln Asp Val Thr
        355                 360                 365

Pro Thr Asn Lys Arg
        370
```